United States Patent
Müller et al.

(10) Patent No.: US 11,259,934 B2
(45) Date of Patent: Mar. 1, 2022

(54) SPINE STABILIZATION DEVICE, AND METHOD AND KIT FOR ITS IMPLANTATION

(71) Applicant: SpineWelding AG, Schlieren (CH)

(72) Inventors: Andrea Müller, Winterthur (CH); Milica Berra, Schlieren (CH); Marcel Aeschlimann, Ligerz (CH); Mario Lehmann, Les Pommerats (CH); Urs Weber, Evilard (CH); Jörg Mayer, Niederlenz (CH); Stephen Hochschuler, Plano, TX (US); Hansen Yuan, Naples, FL (US); Frank M. Phillips, Chicago, IL (US); Stephanie Mehl, Zug (CH); Elmar Mock, Biel/Bienne (CH); Andreas Wenger, Muri b. Bern (CH); Philipp Seiler, Niederdorf (CH); Ulrich Berlemann, Bern (CH)

(73) Assignee: SPINEWELDING AG, Schlieren (CH)

(*) Notice: Subject to any disclaimer, the term of this patent is extended or adjusted under 35 U.S.C. 154(b) by 11 days.

(21) Appl. No.: 16/234,810

(22) Filed: Dec. 28, 2018

(65) Prior Publication Data
US 2019/0133777 A1    May 9, 2019

Related U.S. Application Data

(60) Division of application No. 14/955,314, filed on Dec. 1, 2015, now Pat. No. 10,195,045, which is a
(Continued)

(51) Int. Cl.
*A61F 2/44*  (2006.01)
*A61B 17/70* (2006.01)
(Continued)

(52) U.S. Cl.
CPC .......... *A61F 2/442* (2013.01); *A61B 17/7059* (2013.01); *A61B 17/7098* (2013.01);
(Continued)

(58) Field of Classification Search
CPC ...... A61F 2/4455; A61F 2/446; A61F 2/4465; A61F 2/447; A61F 2/44; A61F 2/442
See application file for complete search history.

(56) References Cited

U.S. PATENT DOCUMENTS

| | | |
|---|---|---|
| 1,487,290 A | 3/1924 | Tomkinson |
| 3,916,907 A | 11/1975 | Peterson |

(Continued)

FOREIGN PATENT DOCUMENTS

| | | |
|---|---|---|
| DE | 8807485 | 8/1989 |
| DE | 29511146 U1 | 11/1995 |

(Continued)

*Primary Examiner* — Si Ming Ku
(74) *Attorney, Agent, or Firm* — Rankin, Hill & Clark LLP

(57) ABSTRACT

A spine stabilization device having an interbody spacer shaped to be inserted between a vertebral body of an upper vertebra and a vertebral body of a lower vertebra. The device further includes a fixation device to be inserted after placement of the interbody spacer, the fixation device having a support portion securing the interbody spacer against escaping from between the vertebral bodies into a ventral direction. The support portion rests against a portion of an anterior surface of the interbody spacer, and includes an anchor. The anchor has an anchoring material portion that is inserted, in a liquid state, into cancellous bone tissue of at least one of the vertebral bodies of the upper and lower vertebra, to thereby infiltrate the cancellous bone tissue, and to harden thereafter so as to fix the support portion to the vertebral body.

18 Claims, 24 Drawing Sheets

Related U.S. Application Data continuation of application No. 12/711,842, filed on Feb. 24, 2010, now Pat. No. 9,220,609.

(60) Provisional application No. 61/155,241, filed on Feb. 25, 2009, provisional application No. 61/242,071, filed on Sep. 14, 2009, provisional application No. 61/302,608, filed on Feb. 9, 2010.

(51) Int. Cl.
  *A61B 17/86* (2006.01)
  *A61B 17/88* (2006.01)
  *A61F 2/28* (2006.01)
  *A61F 2/30* (2006.01)
  *A61F 2/46* (2006.01)

(52) U.S. Cl.
  CPC ........ *A61B 17/864* (2013.01); *A61B 17/8822* (2013.01); *A61B 17/8836* (2013.01); *A61F 2/447* (2013.01); *A61F 2/4601* (2013.01); *A61F 2002/2835* (2013.01); *A61F 2002/30387* (2013.01); *A61F 2002/30401* (2013.01); *A61F 2002/30578* (2013.01); *A61F 2002/30593* (2013.01); *A61F 2002/30594* (2013.01); *A61F 2002/30736* (2013.01); *A61F 2002/30785* (2013.01); *A61F 2002/30904* (2013.01); *A61F 2002/4627* (2013.01); *A61F 2002/4628* (2013.01); *A61F 2002/4629* (2013.01); *A61F 2220/0008* (2013.01); *A61F 2220/0025* (2013.01); *A61F 2310/00023* (2013.01); *A61F 2310/00179* (2013.01); *A61F 2310/00796* (2013.01)

(56) References Cited

U.S. PATENT DOCUMENTS

| | | |
|---|---|---|
| 4,401,112 A | 8/1983 | Rezaian |
| 4,573,458 A | 3/1986 | Lower |
| 4,599,086 A | 7/1986 | Doty |
| 4,904,261 A | 2/1990 | Dove |
| 5,010,247 A | 4/1991 | Smith |
| D364,462 S | 11/1995 | Michelson |
| 5,534,031 A | 7/1996 | Matsuzaki |
| D377,527 S | 1/1997 | Michelson |
| 5,772,661 A | 6/1998 | Michelson |
| 5,782,919 A | 7/1998 | Zdeblick |
| 5,941,901 A | 8/1999 | Egan |
| D425,989 S | 5/2000 | Michelson |
| 6,056,751 A | 5/2000 | Fenton |
| 6,066,175 A | 5/2000 | Henderson |
| 6,080,161 A | 6/2000 | Eaves |
| 6,231,610 B1 | 5/2001 | Geisler |
| 6,235,059 B1 | 5/2001 | Benezech |
| 6,432,106 B1 | 8/2002 | Fraser |
| 6,605,090 B1 | 8/2003 | Trieu |
| 6,793,658 B2 | 9/2004 | LeHuec et al. |
| 6,921,264 B2 | 7/2005 | Mayer |
| 7,060,097 B2 | 6/2006 | Fraser et al. |
| 7,077,864 B2 | 7/2006 | Byrd, III et al. |
| 7,175,624 B2 | 2/2007 | Konieczinsky |
| 7,192,447 B2 | 3/2007 | Rhoda |
| 7,232,464 B2 | 6/2007 | Mathiew et al. |
| 7,255,698 B2 | 8/2007 | Michelson |
| 7,335,205 B2 | 2/2008 | Aeschlimann |
| D580,057 S | 11/2008 | Ramadani |
| 7,452,369 B2 | 11/2008 | Barry |
| 7,819,903 B2* | 10/2010 | Fraser ............. A61B 17/86 606/286 |
| 7,887,595 B1 | 2/2011 | Pimenta |
| 7,963,982 B2 | 6/2011 | Kirschman |
| 8,172,885 B2 | 5/2012 | Songer et al. |
| 8,216,312 B2* | 7/2012 | Gray ............. A61F 2/4455 623/17.11 |
| 8,282,675 B2 | 10/2012 | Maguire |
| 8,403,938 B2 | 3/2013 | Aeschlimann et al. |
| 8,556,947 B2 | 10/2013 | Dorawa et al. |
| 2002/0029082 A1 | 3/2002 | Muhanna |
| 2004/0030341 A1* | 2/2004 | Aeschlimann ........ B29C 66/727 606/232 |
| 2004/0034353 A1 | 2/2004 | Michelson |
| 2004/0053196 A1* | 3/2004 | Mayer ............. A61C 8/0016 433/173 |
| 2004/0210314 A1 | 10/2004 | Michelson |
| 2005/0055098 A1 | 3/2005 | Zdeblick et al. |
| 2005/0159819 A1 | 7/2005 | McCormack et al. |
| 2006/0029907 A1 | 2/2006 | Linder |
| 2006/0085071 A1 | 4/2006 | Lechmann |
| 2006/0105295 A1 | 5/2006 | Mayer |
| 2006/0122703 A1 | 6/2006 | Aebi |
| 2006/0206208 A1 | 9/2006 | Michelson |
| 2006/0276900 A1 | 12/2006 | Carpenter |
| 2007/0016213 A1 | 1/2007 | Robie |
| 2007/0016217 A1 | 1/2007 | Dinville |
| 2007/0106388 A1 | 5/2007 | Michelson |
| 2007/0123989 A1 | 5/2007 | Gfeller |
| 2007/0173938 A1 | 7/2007 | Sweeney |
| 2007/0219635 A1 | 9/2007 | Mathieu et al. |
| 2007/0225695 A1 | 9/2007 | Mayer et al. |
| 2007/0239278 A1 | 10/2007 | Heinz |
| 2007/0276377 A1 | 11/2007 | Yundt |
| 2008/0039845 A1 | 2/2008 | Bonutti |
| 2008/0051890 A1 | 2/2008 | Waugh et al. |
| 2008/0109080 A1 | 5/2008 | Aeschlimann |
| 2008/0269649 A1 | 10/2008 | Dorawa |
| 2008/0300634 A1 | 12/2008 | Gray |
| 2008/0312742 A1 | 12/2008 | Abernathie |
| 2009/0018471 A1 | 1/2009 | Dorawa et al. |
| 2009/0024132 A1 | 1/2009 | Blain et al. |
| 2009/0131947 A1 | 5/2009 | Aeschlimann |
| 2010/0049179 A1 | 2/2010 | Kanaoka et al. |
| 2010/0204737 A1 | 8/2010 | Bae et al. |
| 2010/0312346 A1 | 12/2010 | Kueenzi et al. |
| 2012/0316649 A1 | 12/2012 | Johnston et al. |
| 2012/0323330 A1 | 12/2012 | Kueenzi et al. |
| 2013/0138217 A1 | 5/2013 | Laurence et al. |

FOREIGN PATENT DOCUMENTS

| | | |
|---|---|---|
| EP | 0179695 | 4/1986 |
| EP | 0599766 | 6/1994 |
| EP | 0951879 | 10/1999 |
| JP | 2006-43453 | 2/2006 |
| JP | 2006-503668 | 2/2006 |
| JP | 2007-522827 | 8/2007 |
| WO | 95/26164 | 10/1995 |
| WO | 9720526 | 6/1997 |
| WO | 02/069817 | 9/2002 |
| WO | 02/078574 | 10/2002 |
| WO | 2004/017857 | 3/2004 |
| WO | 2005/025431 | 3/2005 |
| WO | 2005/079696 | 9/2005 |
| WO | 2007098288 | 8/2007 |
| WO | 2008/034277 | 3/2008 |
| WO | 2008034276 | 3/2008 |
| WO | 2008/095327 | 8/2008 |
| WO | 2008128367 | 10/2008 |
| WO | 2009/055952 | 5/2009 |
| WO | 2009/064644 | 5/2009 |
| WO | 2009109057 | 9/2009 |
| WO | 2009132472 | 11/2009 |
| WO | 2010/045751 | 4/2010 |

* cited by examiner

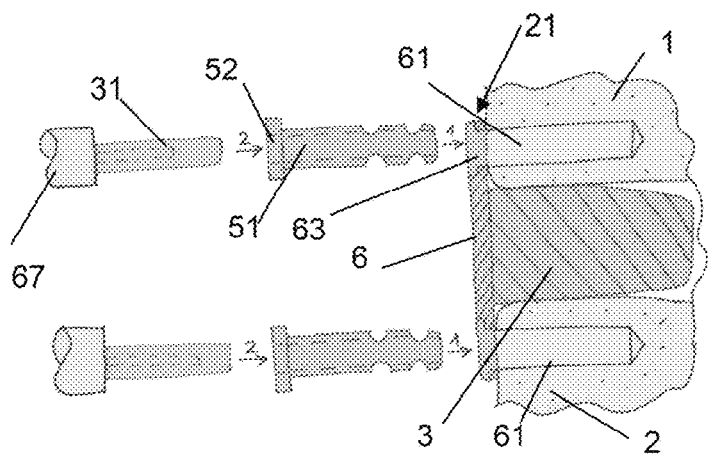
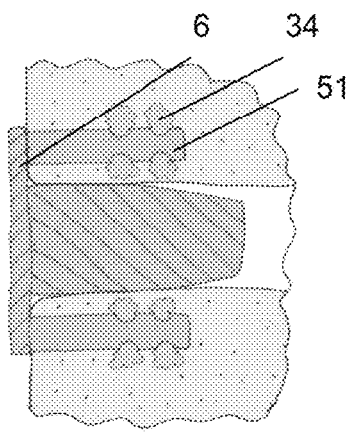
Fig. 16a Fig. 16b
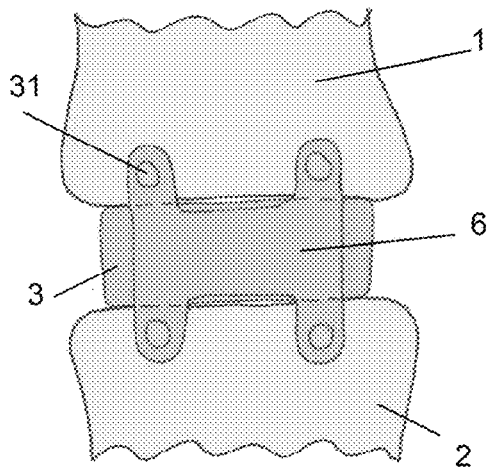
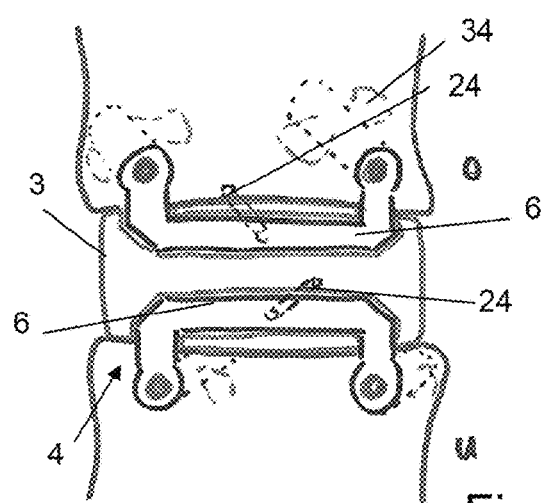
Fig. 17 Fig. 18
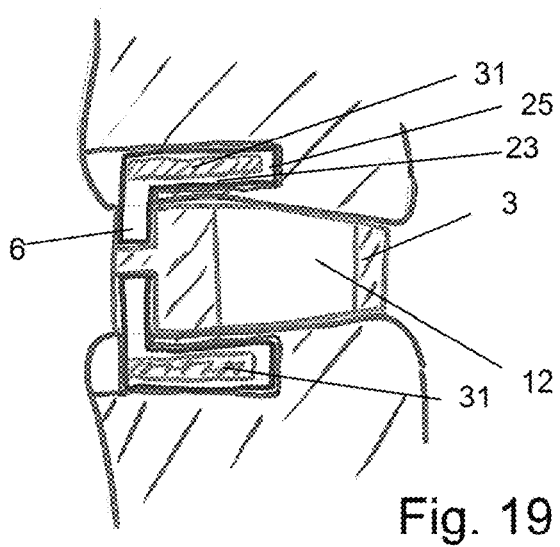
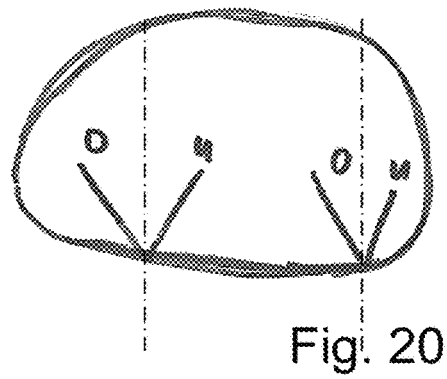
Fig. 19 Fig. 20

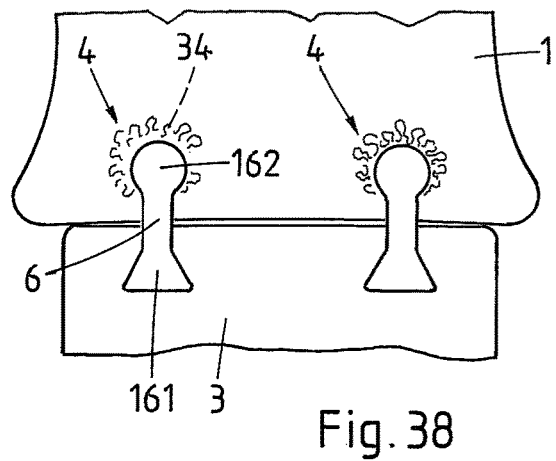
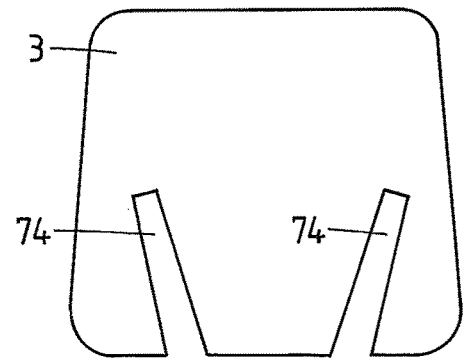
Fig. 38     Fig. 39
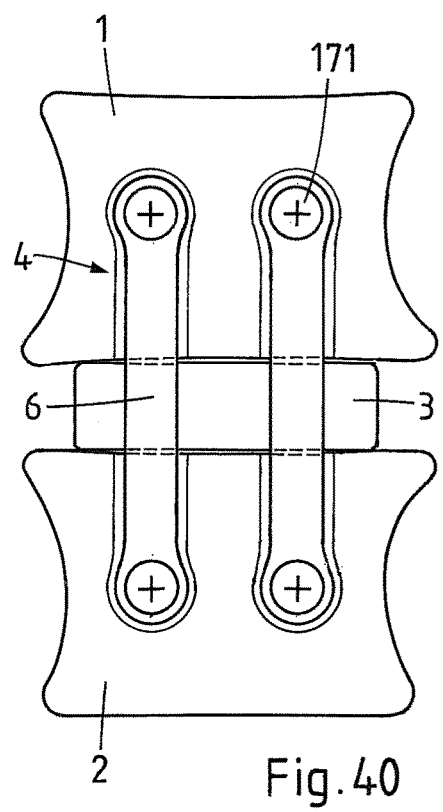
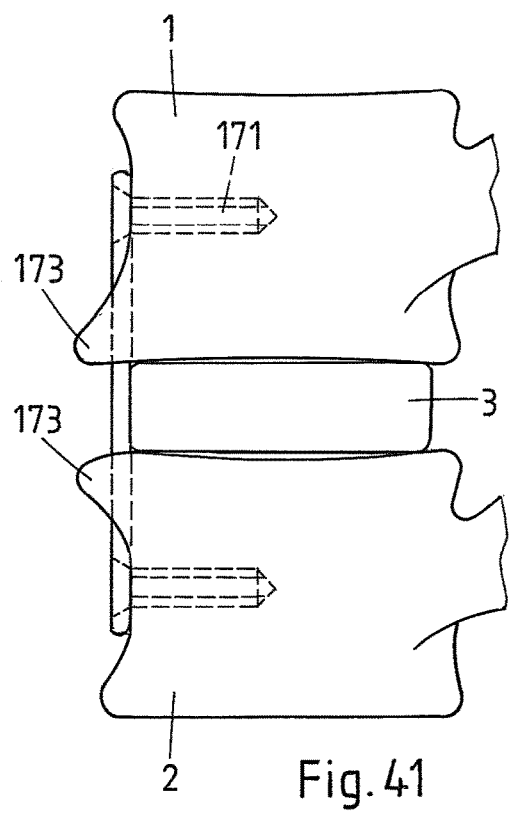
Fig. 40     Fig. 41

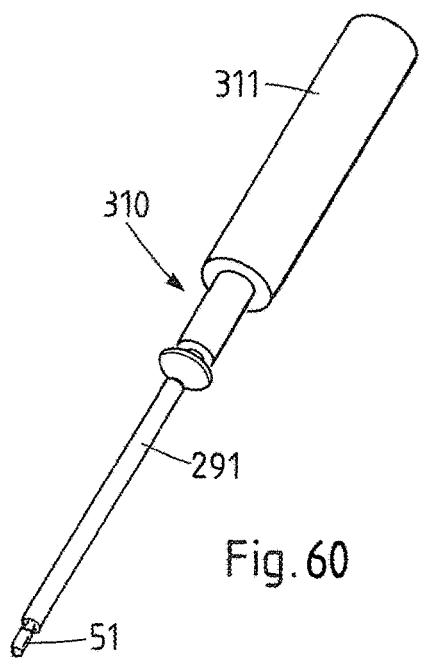
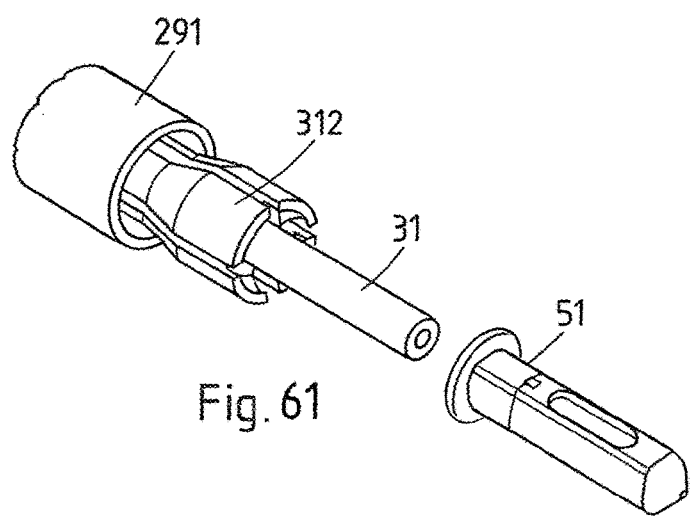
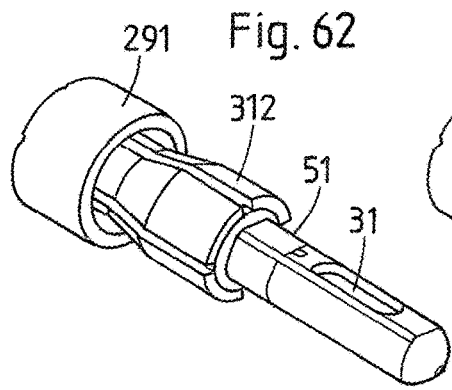
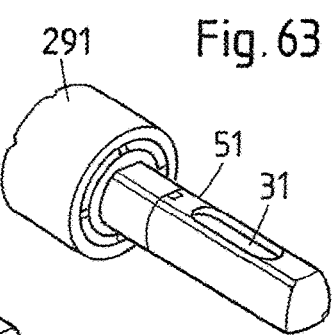
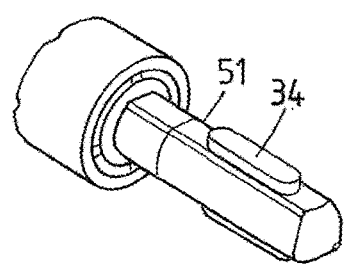
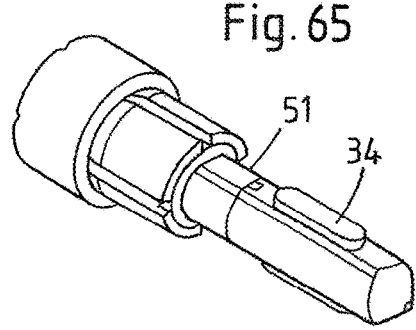
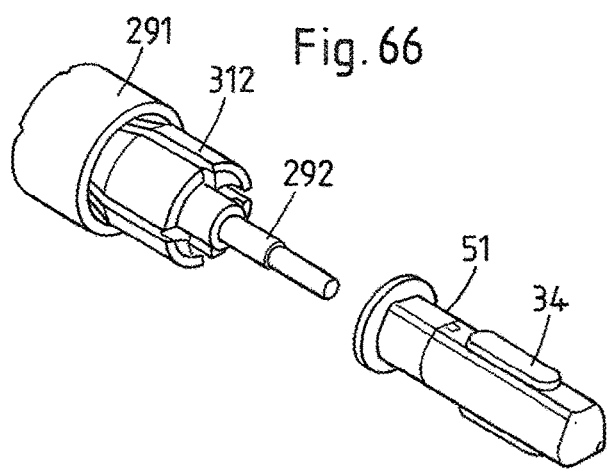

SPINE STABILIZATION DEVICE, AND METHOD AND KIT FOR ITS IMPLANTATION

FIELD OF THE INVENTION

The invention relates to a spine stabilization device used in spinal surgery as a spacer in place of a degenerated or injured intervertebral disc between two adjacent vertebral bodies for permanent fusion of two vertebrae. The invention further relates to kits of instruments for implantation of the spine stabilization device, and to methods of implanting the device.

BACKGROUND OF THE INVENTION

In the prior art, such implant systems which function as spacers between adjacent vertebral bodies to be fused and replace injured or degenerated intervertebral discs are known:

U.S. Pat. No. 7,077,864 describes an example of a vertebral interbody cage that can be implanted from an anterior, posterior, anterolateral or lateral position. A cage is an example of a vertebral interbody spacer and spine stabilizer. The cage is filled with bone graft or bone growth promoting material, which promotes the fusion of the vertebrae for long term stability. Advantageously, three screws are used for fixation of the cage, wherein one screw projects at one angle up or down and the other two screws are angled so as to splay in opposite directions. Preferably, the screws are to be inserted through the anterior wall of the cage and through the endplates of hard cortical bone into the softer, more cancellous portion of the bone of the adjacent upper and lower vertebral body to fix the relative position of the cage and vertebral bodies. Furthermore, precautions are necessary to fix the screws in the anterior wall of the spacer or cage in such a way that the screw heads do not protrude outwards of the anterior wall of the cage and that the screws cannot loosen to avoid damaging the major blood vessels that run along the anterior portion of the spine.

Similarly, U.S. Pat. No. 7,232,464 teaches an intervertebral spacer implant with a three-dimensional structure with several boreholes designed to receive screws or other elongate affixation means which can be rigidly connected to the intervertebral implant and are anchored in the adjacent vertebral bodies through penetration of either the inferior or the superior or both of the endplates. The affixation means are typically guided at an angle deviating more than 25°, preferably 35°-55° from the median plane. Such an arrangement of the affixation means ensures anchoring in the compact cortical bone of the endplates of the adjacent vertebral bodies. Again special measures are taken such that the affixation means neither loosen nor protrude, in order to avoid damaging of the major blood vessels.

The fixation of these and other interbody spacers to the vertebral bodies relies on the penetration of the cortical bone of the endplate. Thus the exact placement and angular guiding of the screws is critical. Driving the fixation means through the endplates may weaken the cortical bone of the endplates, compromising the stability of the vertebral bodies. This may be problematic if the bone quality is already weakened by degenerative osteoporosis or traumatic injury or if multiple attempts for the fixation are required during the surgical procedure. Furthermore, during spine surgery access to apply instruments is often limited and it may be difficult to drive affixation means into the vertebral bodies at such pronounced angles required to drive the fixation means from the frontal or a lateral side wall of the intervertebral spacer implant through the endplates of the vertebral bodies.

U.S. Pat. No. 7,255,698 discloses devices for stabilizing vertebral bodies, which devices include an interbody spinal fusion implant and spinal fixation devices secured by a screw to the interbody spinal fusion implant so that loosening of the device is prevented. The spinal fixation devices have a length exceeding the distance between the two adjacent vertebral bodies and are engaged in both vertebral bodies by means of screws or ratchet like structures.

Also in this system, measures have to be taken so that the screw heads do not protrude outwards of the anterior wall of the cage and that the screws cannot loosen to avoid damaging the major blood vessels that run along the anterior portion of the spine. A further potential problem lies in the engagement between the spinal fixation devices and the vertebral bodies. Especially in the case of already weakened bone the fastening primarily relies on a mechanic engagement between a screw or staple with ratcheted structures on the one hand and a relatively thin layer of anterior cortical bone on the other hand. Constant mechanical wear may damage the bone tissue in a vicinity of the screw or staple projection, and this may result in a loosening of the screw or staple.

SUMMARY OF THE INVENTION

It is the objective of the invention to overcome the disadvantages of intervertebral implants according to the state of the art.

According to a first aspect of the invention, a spine stabilization device is provided, the spine stabilization device comprising an interbody spacer shaped to be inserted between a vertebral body of an upper vertebra and a vertebral body of a lower vertebra, and comprising a top surface oriented towards the lower endplate of the vertebral body of the upper vertebra and a bottom surface oriented towards the upper endplate of the vertebral body of the lower vertebra; and a fixation device (preferably to be inserted after placement of the interbody spacer), the fixation device comprising a support portion securing the interbody spacer against escaping from between the vertebral bodies of the upper and lower vertebra to the side at which the fixation devices are arranged (being the ventral direction in many embodiments), the support portion shaped to rest against a portion of a surface (such as the anterior surface) of the interbody spacer, and further comprising an anchor, the anchor comprising an anchoring material portion that is configured to be inserted, in a liquid state, into for example cancellous bone tissue of the vertebral body (the more dense sub-cortical bone tissue is considered to be cancellous bone tissue in the context of the present application) of the upper vertebra and/or of the vertebral body of the lower vertebra, to thereby infiltrate the cancellous bone tissue, and to harden thereafter so as to fix the support portion to the vertebral body.

In this, and in all aspects of the invention, the upper and lower vertebra may be neighboring vertebra. Then, the interbody spacer may replace the intervertebral disc and may serve as spinal fusion implant or may serve as intervertabral disc prosthesis restoring the function of an intervertebral disc. The concepts of the aspects of the invention are also suited for multi-segment fusion, i.e. the replacement of a plurality of intervertebral discs. Most embodiments of the invention feature the advantage of a small constructional height, and this makes them especially suited for multi-segment fusion.

Alternatively, a vertebra may be at least partially removed, together with the adjacent intervertebral discs. Then, the interbody spacer replaces the vertebral body of the at least partially removed vertebra as well as the removed intervertebral discs, and the upper and lower vertebra are not initially neighboring vertebra but vertebra neighboring the removed vertebra.

Also, in all aspects of the invention, the fixation device for the interbody spacer (or the anchoring devices) may be the only fixation device(s) or may be adjuvant fixation devices used in addition to other fixation devices, for example according to the state of the art. Such other fixation devices may for example be pedicle screws to be introduced from a posterior side.

This concept according to the first aspect of the invention brings about a major advantage compared to prior art approaches that rely on anchoring by a screw or a fastener with ratcheted structures or the like. Namely, prior art fasteners of this kind have a very limited surface. Especially in cancellous bone, only few trabeculae can participate in absorbing forces, and the main fraction of any force will have to be absorbed by the relatively thin layers of cortical bone tissue, that in addition are weakened by the penetration by the fasteners. In contrast thereto, the approach according to the first aspect of the invention brings about a strengthening of the bone bed and the according mount, because spaces between trabeculae in the cancellous bone are filled by anchoring material, local weaknesses are evened out and the force is distributed to a large fraction of the bone tissue. Because of this, the anchoring is not only stronger but also more lasting, since a wear of the bone tissue is prevented. A possible residual elasticity of the anchoring material may further enhance this effect because minor movements relative may then be absorbed by the anchoring material.

In this text, often the dorsal and ventral directions are referred to as posterior and anterior directions following the convention that is applicable for humans; this does not exclude the application of the devices and methods taught herein also for veterinary purposes; in this case "anterior" is generally to be replaced by "ventral", "posterior" by "dorsal". Also, terms like "upper", "lower", "above", "below", "top", "bottom" are used in this text, and this does not exclude the application of the devices and methods for spine segments that are, in a normal position, not vertical. Generally, "upper" and "above" etc. refer to more cranial positions, "below" or "lower" to more caudal positions.

The interbody spacer is a three dimensional body with a top surface to be oriented towards—and for example contacting—the lower endplate of the vertebral body above and with a bottom surface to be oriented towards—and for example contacting—the upper endplate of the vertebral body below the spacer, and with a circumferential surface that may comprise a front, back and side walls in anterior, posterior and lateral orientations to the spinal column. The top and the bottom surface of the spacer may be essentially parallel. In other embodiments, they are tilted slightly towards each other such that the dorsal portion of the circumferential surface is less high than the ventral wall portion of the circumferential surface, and the spacer forms a flat wedge imitating the anatomical form of an intervertebral disc (or of a vertebral body with intervertebral discs).

While in most embodiments, especially for anterior or anteriolateral or lateral implantation, the interbody spacer is of one piece, it may in special embodiments also comprise a plurality of pieces, especially for implantation from a dorsal side.

The median plane of the implanted intervertebral spacer runs approximately (not accounting for the optional slight taper) parallel to the adjacent endplates of the vertebral bodies above and below. In the context of this application the orientation of the median plane is sometimes referred to as "horizontal" while "vertical" always refers to an orientation essentially parallel with respect to the longitudinal (craniocaudal) extension of the spine in the region of the spine where two vertebral bodies need to be fused in a particular case.

For example, the interbody spacer is made from a plastic material such as PEEK (Polyetheretherketone) or of Titanium, but other biocompatible materials are possible also, including other plastics, other metals, and ceramics. In some embodiments a surface coating of Hydroxilapatite (HA) is applied enhancing the osseointegrative properties of the interbody spacer and therefore promote longterm stability.

The interbody spacer may furthermore be shaped to comprise further structural elements such as recesses, bores, indentations, bulges and other three dimensional structures, which modify the properties of the spacer and/or which accommodate corresponding structures of the at least one fixation device or anchoring device. Furthermore the material of the interbody spacer does not have to be uniform: it may be composed of more than one material components, and/or it may contain filler materials like stabilizing fibers etc.

Turning to the fixation device(s), the support portion of the fixation device defines an interface with the interbody spacer, where the interbody spacer—possibly depending on its exact position—may rest against the fixation device, thereby being secured against movements in a ventral direction. The support portion preferably is made of a material different from the anchoring material; preferably the material—or material composite or material system—that constitutes the support portion is more solid than the anchoring material, for example metallic, of a hard plastics like PEEK or of a ceramic material.

The anchor may comprise a solid anchoring structure, the solid anchoring structure defining an elongate cavity that opens towards a material introduction side at a first end, the anchoring structure further comprising a base delimiting the elongate cavity towards a second end opposite the first end, and at least one lateral opening where the cavity opens towards a bone side, wherein the anchoring material is adapted to be inserted at least partially into the cavity from the material introduction side at the first end and to exit the cavity, in a liquid state, at least partially into cancellous bone tissue through the at least one lateral opening.

In this, the solid anchoring structure may for example be formed by a fixation device body of the fixation device, which fixation device body also comprises the support portion. As an alternative, the anchoring structure may be constituted by elements that are initially separate from the support portions. Such separate elements may be tube (or sheath or sleeve) elements with at least one lateral opening for liquefied material to be pressed out and into structures of the tissue in which anchoring is desired. This principle of pressing liquefied material out of a tube or sleeve element with for example lateral openings is for example described in U.S. Pat. Nos. 7,335,205, 6,921,264, US 2009/0 131 947, WO 2009/132 472, and U.S. application Ser. No. 61/259, 383, all of which being incorporated herein by reference. In such embodiments, the anchoring material may be mounted to the fixation device body or pre-assembled with the fixation device body. As yet another alternative, the anchor may be formed by an anchoring device comprising thermoplastic surface portions liquefiable by mechanical vibrations, as described in U.S. Pat. Nos. 7,335,205, 6,921,264, US 2006/0 105 295 (and thus comprise self-reaming structures), US 2008/0 109 080 or US 2009/0 131 947. All documents cited in this paragraph are incorporated herein by reference in their entirety.

A fixation device body may be made of titanium or other biocompatible material of sufficient mechanical strength, including plastic material such as PEEK, for example with a roughened surface and/or with an appropriate coating for better bone ongrowth resulting in longterm stability.

The interbody spacer for example comprises at least one indentation, such as a recess to accommodate the support portion. Then, the support portion does not protrude in an anterior direction above the circumferential surface of the interbody spacer or only to an extent that is less than the support portion's thickness. The at least partial arrangement of the support portion in a countersunk fashion may prevent tissue irritation and thus advance the healing process.

The anchoring material may according to a first, especially preferred group of embodiments be provided as a thermoplastic material liquefiable by mechanical movement, especially mechanical oscillation. The anchoring material may then for example be present as separate (but potentially pre-assembled) anchoring material element, or as thermoplastic portion of an anchor element. The anchoring process may include coupling mechanical oscillations into the initially solid anchoring material while subjecting it to a pressing force pressing it against a counter element and/or against bone tissue so that absorbed mechanical energy at a desired place effects a partial or full liquefaction of the anchoring material. The liquefied material penetrates into structures such as open pores etc. of the bone tissue into which it is pressed. This process is sometimes also referred to as 'infiltration'. Upon re-solidification, the anchoring material forms a positive-fit connection between the bone and the anchoring element of the retention element.

In this first group of embodiments, the anchoring material may according to a first alternative be resorbable. Then, in the time following implantation, the anchoring material is slowly replaced by bone ongrowth. Then, as an option, the anchoring location may comprise surface regions not of the anchoring material but provided with structures suitable for osseointegration, as for example described in U.S. Pat. No. 6,921,264, incorporated herein by reference. According to a second alternative, the anchoring material may be a non-resorbable material for permanent fixation.

According to a second group of embodiments, the anchoring material is a cement or thermosetting resin or the like that in the anchoring is irreversibly brought from a liquid state into a solid state.

In some embodiments, the anchoring structures are arranged and shaped so that the anchoring material elements (or the entire anchoring devices including the anchoring structure) are introduced essentially parallel to each other with regards to the up-down direction, with the projection of introduction axes onto the sagittal plane for example not differing by more than 20°. For example, the direction of introduction does not deviate by more than 10° from a median plane of the interbody spacer's top and bottom surfaces. In other embodiments, the angle between the superior and posterior anchoring material introduction axes, in a projection onto the sagittal plane may be larger, so that the anchors protrude into a core of the vertebral bodies.

Also, in some embodiments the left and right anchors in a projection onto the median plane are not parallel to each other but are for example oriented in an outward or possibly inward direction.

In a category of embodiments of the invention, fixation device(s) comprise at least two anchoring locations for forming an anchor, wherein the anchoring locations are arranged such as to be form anchors inserted from the circumferential surface of the vertebral body/bodies, such as to leave the end plates intact (except for a potential anterior recess for accommodating a part of the support portion). Anchoring for example may be effected in the anterior, lateral or anteriolateral (or also posterolateral or posterior) wall of the vertebral body above and/or below the interbody spacer. In some of these embodiments, the anchoring locations of a given fixation device are arranged so as to form anchors in the upper and the lower vertebral body, respectively, so that the fixation device spans across the space between the vertebral body and has a longitudinal extension exceeding the longitudinal extension of the interbody spacer. The support portion then may be elongate and plate- or rod-like and be approximately parallel to the longitudinal spine axis or at an angle thereto. In other ones of these embodiments the anchoring locations of a given fixation device are arranged to form anchors in a same vertebral body, so that the support portion is a bow (or bridge) vertically spaced from the anchoring location.

In either case, the interbody spacer may comprise anterior indentations such as channel-like recesses to accommodate the support portion so that the support portion, in the implanted state of the spine stabilization device, does not anteriorly protrude from the interbody spacer or protrudes less than its thickness. Instead of such a recess or in addition thereto, the device may comprise means for adapting a depth position of the interbody spacer relative to the support portion (and thus also relative to the vertebral bodies). In particular, the support portion may comprise at least one protrusion to keep the interbody spacer at a distance from the support portion, which distance is defined by the protrusion. Such a protrusion may additionally or as an alternative also be provided on or the interbody spacer. In addition or as an alternative to such a protrusion, the device may comprise at least one separate connection element that has a certain thickness (and the surgeon may for example choose between different connection elements of different thicknesses to adapt the interbody spacer depth position to the needs) and that is shaped to be inserted and held between the support portion and the interbody spacer.

Such a means for adapting the depth may also be advantageous in view of a size reduction of the interbody spacer that may be desired depending on the situation.

In some embodiments, the fixation device has a fixation device body that includes two solid anchoring structures in physical continuity with the support portion. The anchoring structures may partially enclose an elongate cavity for the anchoring material and thus themselves be elongate and at an angle to the support portion.

The fixation device body—in any embodiment including a support portion—may additionally comprise at least one guiding portion which protrudes from the support portion and into a corresponding indentation of the interbody spacer for further dimensional stability of the arrangement after implantation. Thus a fixation device body comprising the support portion and two anchoring structures each connected an end of the support portion may have an overall staple-like shape, and with an additional, centrally located guiding portion it may be "E" shaped. Other arrangements of the portions of the fixation device body are possible.

A further category of embodiments, which is an alternative to the category of embodiments where anchors are inserted from the circumferential surface of the vertebral body/bodies, such as to leave the end plates intact, again avoids penetration of the endplates by screws or other pin-shaped fixation elements. Instead of leaving the endplates entirely intact, however, a small portion of the surface of endplate oriented towards the spacer is replaced by an anchoring portion of the fixation device body with a portion protruding above (and below) the space between the vertebral bodies (and thus above and below the top surface and the bottom surface, respectively, of the interbody spacer) and that may have a surface dome-shaped in cross-section and parallel to the proximodistal insertion axis. In this case forces that are normally supported by the endplate are partially transmitted to the fixation device. Thus, although the endplates are not left intact, their stability providing capability is not overly weakened by the surgical operation, but there may even result strengthening. Further, in a preferred embodiment, the portion of the endplate that is removed is a central portion (with respect to the sagittal plane), thus the stronger lateral portions are left intact. This preferred embodiment also features the advantage that the removal of the cortical portions of the upper and lower vertebral bodies may be done in a single step, as described in more detail further below.

The fixation device body of embodiments of this category of embodiments may generally be made of as a single piece, for example of titanium with a roughened surface for better osseointegrative properties, or of a suitable ceramics or plastic material such as PEEK. The support portion connects the anchoring portions, runs along the anterior circumferential wall portion of the interbody spacer and may be of a ring shape or oval or elliptic shape with thus two bow portions or plate-like. The anchoring portions fit into a corresponding recess, which has been cut into the cortical layer of the endplates of the vertebral bodies above and below the intervertebral spacer. The anchoring portions each encompass at least one elongate cavity open to the anterior side and comprising at least one outward facing opening for releasing anchoring material into the cancellous bone of the vertebral bodies where the endplates have been partially removed.

The upper and lower anchoring portions may be essentially orthogonal to a plane defined by the support portion. The retention element may additionally comprise at least one guiding element that is also connected with the support element in essentially orthogonal orientation to plane defined by the support portion. Also in this category of embodiments, the interbody spacer may comprise recess structures for accommodating the support portion so that the latter does not protrude or protrudes only to a reduced extent over the anterior end wall of the interbody spacer. According recesses may also be provided in the bone tissue between the anchoring locations (for example defined by pre-drilled holes) and the interbody space, so that the whole spine stabilization device may for example be free of parts protruding from an anterior (or anteriolateral or lateral) end face of defined by the vertebral bodies. This prevents the damaging or irritation of vessels or other organs in vicinity of the vertebrae.

Methods of implanting the spine stabilization device according to the invention may include preparing pre-drilled holes in the bone tissue at a suitable location, preferably using a drill guide. "Drilling" or "drilled" etc. in the context of the present application include making non-circular holes by for example punching-like approaches. An example of a method of making holes of not necessarily circular cross section in bone is disclosed in US 2008/0269649, and the skilled person is referred to the teaching of this document. The approach of the invention is especially suited for anchoring in recesses of any cross section, because not circular movement is required during the anchoring process.

In addition or as an alternative, the anchoring structures (or also separate anchoring (such as tube elements)) may have self-cutting and/or self-reaming properties.

According to a second aspect of the invention, that is especially suited for embodiments of the first category of the first aspect, a spine stabilization device is provided, the spine stabilization device comprising:

An interbody spacer shaped to be inserted between a vertebral body of an upper vertebra and a vertebral body of a lower vertebra, and comprising a top surface oriented towards the lower endplate of the vertebral body of the upper vertebra and a bottom surface oriented towards the upper endplate of the vertebral body of the lower vertebra; and At least a first fixation device and a second fixation device to be inserted after placement of the interbody spacer, and preferably anteriorly thereof, the first and second fixation devices each comprising a support portion for securing the interbody spacer against escaping from between the vertebral bodies of the upper and lower vertebra into a direction towards the fixation devices (for example into a ventral direction), the support portions shaped to rest against a portion of a (for example anterior) surface of the interbody spacer, and further comprising a fastener for securing the first and second fixation devices to one of the vertebral bodies or to both vertebral bodies, the first and second fixation devices further each comprising at least one (first) guiding portion, and the interbody spacer comprising a corresponding number of indentations (second guiding portions) accommodating the first guiding portions, where an axis of an indentation accommodating a guiding portion of the first fixation device and an axis of an indentation accommodating a guiding portion of the second fixation device are non parallel.

It would also be possible to reverse the arrangement of the guiding portions for all or some of the guiding portions and to for example shape at least one guiding portion of the fixation devices as indentation(s), and at least one corresponding second guiding portion as corresponding protrusion(s) of the interbody spacer, with two second guiding portions having non-parallel axes.

Preferably, the axes for the guiding portion(s) of the first and of the second guiding portion accommodating indentations diverge or converge in the transverse plane, i.e. the projections of the axes onto the transverse plane are non-parallel.

By this, the interbody spacer, without the need for coupling means such as a screw, is secured not only against movements into an anterior direction (by the support portions) but also against movements into a posterior direction, because for geometrical reasons once both guiding portions are inserted from anterior direction, the fixation devices' positions being fixed relative to the vertebral column, a relative movement of the interbody spacer is not possible any more.

The fasteners may, according to a first variant, be configured as anchors according to the above-discussed first aspect of the invention and comprise anchoring material that during interpenetration of bone tissue is in a liquid state. In other embodiments, fasteners may comprise a screw, a pin with barb-like structures, a self-spreading anchoring pin, a shape memory spreading pin, or any other suitable surgical fastener as known in the state of the art.

The fasteners, whether or not they are provided as anchors according to the first aspect of the invention, in many embodiments comprise at least one elongate portion for being inserted in a corresponding opening in the bone tissue, which opening may be pre-drilled. In embodiments in which the elongate portion is rigidly connected to the support portion, and for example a solid anchoring structure of a fixation device body, or alternatively a solid arm of a staple-like rigid fixation device, the pre-drilled hole in the bone tissue for the elongate portion should be parallel to the respective axis of the guiding portion.

A kit of parts for preparing a spine for implantation of a spine stabilization device according to the second aspect of the invention may therefore comprise a drill guide for defining the drilling axis of a plurality of bores in the vertebral bodies, the bores for the first fixation device and the bores for the second fixation device having non-parallel axes. According to a third aspect of the invention a spine stabilization device is provided, the spine stabilization device comprising:

An interbody spacer shaped to be inserted between a vertebral body of an upper vertebra and a vertebral body of a lower vertebra, and comprising a top surface oriented towards the lower endplate of the vertebral body of the upper vertebra and a bottom surface oriented towards the upper endplate of the vertebral body of the lower vertebra, the interbody spacer comprising at least one channel-like recess reaching to an anterior end in the top surface and at least one channel-like recess reaching to an anterior end in the bottom surface, and comprising, in a region of these recesses a structure that includes an undercut and is suitable for making a positive-fit connection together with re-solidified liquid material flown into the structure; and For every channel-like recess an anchoring device, the anchoring devices comprising a proximal end and a distal end, a first securing portion, a second securing portion and a bridge portion between the first and second securing portions, wherein each of the first and second securing portions protrudes, on the distal side further than the bridge portion, and wherein the first and second securing portions comprise material liquefiable by thermal energy (e.g. friction heat created by mechanical oscillation or absorption heat created by absorption of electromagnetic radiation preferably of the visible or infrared frequency range), so that the first securing portion is equipped for being anchored in bone tissue with the aid of e.g. mechanical oscillation or electromagnetic radiation, and the second securing portion is equipped for being anchored in the same manner in the structures.

The device according to the third aspect of the invention is an improvement over the device shown in FIGS. 26-29 of WO 2008/034 276. More concretely, the first and second securing portions each function as an anchor anchored in the bone tissue and in the interbody spacer, respectively. The anchoring in these two elements takes place simultaneously by the joint action of e.g. mechanical vibration or electromagnetic radiation coupled into the anchoring device and a pressing force pressing it towards the distal direction (corresponding to the posterior direction). Due to the bridge portion, the anchoring device then forms a solid connection between the bone tissue and the interbody spacer.

Preferably, a total of four anchoring devices are provided, two for the top surface and two for the bottom surface.

The fourth aspect of the invention is especially suited for vertebrae the vertebral bodies of which comprise, towards the lower respectively upper endplates, bulges towards the ventral side. Such bulges are for example encountered in patients that have suffered from problems with the intervertebral disc for a long time. According to the fourth aspect of the invention, a spine stabilization device comprises:

An interbody spacer shaped to be inserted between a vertebral body of an upper vertebra and a vertebral body of a lower vertebra, and comprising a top surface oriented towards the lower endplate of the vertebral body of the upper vertebra and a bottom surface oriented towards the upper endplate of the vertebral body of the lower vertebra; and At least one fixation device comprising a support portion for securing the interbody spacer against escaping from between the vertebral bodies of the upper and lower vertebra into a direction towards the fixation device, the support portion shaped to rest against a portion of a surface of the interbody spacer, and further comprising a first fastener for securing the fixation device to the upper vertebral body and a second fastener for securing the fixation device to the lower vertebral body, wherein a length of the fixation device with respect to a longitudinal spine axis is such that the fasteners are arranged in a central part (with respect to the longitudinal, craniocaudal direction) of the respective vertebral body.

An according method of implanting a spine stabilization device according to the fourth aspect includes the step of anteriorly removing cortical bone of the vertebral body in the region of the bulge to provide a countersink for the support portion but to leave the cortical bone intact in a central region of the anterior wall of the respective vertebral body. The fastening is then achieved in the central region (for example position along the spine axis is in the middle two quarters or in the middle third of the vertebral body extension). This features the advantage that the fixation devices are countersunk so as not to harm vessels and other organs arranged ventrally of the vertebral bodies, and nevertheless anchoring is at least partially in the cortical bone.

The concept according to the fourth aspect may be combined with the first aspect and/or the second aspect.

According to a fifth aspect of the invention, a spine stabilization device is provided, comprising An interbody spacer shaped to be inserted between a vertebral body of an upper vertebra and a vertebral body of a lower vertebra, and comprising a top surface oriented towards the lower endplate of the vertebral body of the upper vertebra and a bottom surface oriented towards the upper endplate of the vertebral body of the lower vertebra; and A fixation installation, the fixation installation comprising one fixation device or two fixation devices, the fixation device or each fixation device, respectively, comprising a support portion for securing the interbody spacer against escaping from between the vertebral bodies of the upper and lower vertebra into a direction towards the fixation device, the support portion shaped to rest against a portion of a surface of the interbody spacer, the fixation installation comprising two first fasteners for securing the fixation device or fixation devices to the upper vertebral body and two second fasteners for securing the fixation device to the lower vertebral body, the fixation device or fixation devices, respectively, further comprising, for each fastener, a fastener receiving opening shaped to guide one of the fasteners in a guiding direction, wherein the guiding directions of the first fasteners and the guiding directions of the second fasteners are, in a projection onto the sagittal plane, at an angle with respect to each other, and wherein the guiding directions and the positions of the fastener receiving openings are such that the first and second fasteners traverse the cortical bone of the upper and lower vertebral bodies, respectively, at a place different from the lower and upper endplates.

The fasteners are thus not introduced parallel to each other (and to a median plane) as in prior art approaches, but at an angle thereto, preferably outwardly (i.e. the angle between the fasteners opens towards the distal side; the fasteners are inserted in a diverging manner). Nevertheless, in contrast to other prior art approaches the fasteners do not traverse the endplates and thus do not weaken this important bone tissue.

In this, the fasteners may be conventional fasteners such as surgical screws or other fastening pins with retention structure. As alternatives, other fasteners according to the state of the art could be used. As yet further alternatives, the fasteners could be configured in accordance with the anchors of embodiments of the first aspect of the invention that are based on the principle of causing anchoring material in a liquefied state to flow into structures of the bone tissue and to then liquefy.

It has been found that by the approach according to the fifth aspect of the invention, a good, reliable anchoring may be achieved. Moreover, the angle in projection onto the sagittal plane (in the following termed "the sagittal angle") may be comparably small. Nonzero angles less than 40°, less than 30° or even less than 20° to the median plane are possible, for example between 4° and 30° or between 4° and 18° to the median plane, or between 6° and 16° to the median plane; preferably the sagittal angle of the upper and lower fasteners, with respect to each other is between 8° and 36°, where also an asymmetric arrangement (for example with the angle of the lower fasteners to the median plane being 0° and the angle of the upper fasteners to the median plane being 8° or more) is possible.

This features the advantage that a straight approach to the implantation site while without any momentum or energy deviating means is possible; especially there is no need for a Cardan joint if the fastener is a surgical screw or an other device that has to be rotated is required.

By the approach according to the fifth aspect of the invention, fusion of vertebrae that so far were not easy to fuse becomes possible. For example for the fusion of L5 with S1—that so far was difficult to achieve because of the position of these two vertebrae in the body—the sagittal angle of the upper (more cranial) fasteners with respect to the median plane may be around 0°, whereas the sagittal angle of the lower (more caudal) fasteners are substantially higher than 0°. More in general, the approach according to this aspect of the invention provides flexibility regarding the fusion of different vertebrae; the angles may be adapted to each vertebral fusion operation, and even to different patients.

In a preferred embodiment, the fastener receiving openings are arranged immediately adjacent an upper and lower edge, respectively, of the interbody spacer. Cortical bone tissue to be removed or penetrated for implantation is therefore at the edge between the anterior surface and the top or bottom plate, respectively.

In embodiments of the invention, the fixation installation comprises a single fixation device with the four fastener receiving openings. The fastener receiving openings are located in loops or other protrusions that protrude from a plate-like fixation device support portion towards the cranial and caudal sides, respectively.

Preferably, the dimensions of the interbody spacer and of the fixation device(s) are shaped and adapted to the anatomy of the patient so that the loops or other protrusions that incorporate the fastener receiving openings are counter-sunk in the vertebral body to at least some extent, preferably so that their anterior surface is approximately flush with the vertebral body's anterior surface. Also, preferably the interbody spacer has a structure that allows the fixation device to be countersunk in the interbody spacer, too.

In embodiments of the invention, the first aspect is combined with the fifth aspect.

According to a sixth aspect of the invention, a spine stabilization device is provided, the device, comprising:

An interbody spacer shaped to be inserted between a vertebral body of an upper vertebra and a vertebral body of a lower vertebra, and comprising a top surface oriented towards the lower endplate of the vertebral body of the upper vertebra and a bottom surface oriented towards the upper endplate of the vertebral body of the lower vertebra; and A fixation device comprising a support portion for securing the interbody spacer against escaping from between the vertebral bodies of the upper and lower vertebra into a direction towards the fixation device, the support portion shaped to rest against a portion of a surface of the interbody spacer, the fixation device comprising two first fastener receiving openings, each for receiving a fastener for fastening the fixation device to the upper vertebral body and two second fastener receiving openings, each for receiving a fastener for fastening the fixation device to the lower vertebral body, wherein the first fastener receiving openings are at a first distance with respect to each other, and wherein the second fastener receiving openings are at a second distance with respect to each other, the second distance being different from the first distance.

For this reason, the fasteners of two spine stabilization devices affixed above and below to a certain vertebral body will not interfere with each other, even if the fasteners are comparably long and/or if the sagittal angles are substantial.

To this end, to be on the safe side, the difference between the first and second distances preferably corresponds at least to a diameter of a fastener receiving opening. If the fastener receiving openings have unequal diameters, the condition will be that the difference at least corresponds to the arithmetic mean of the two diameters.

In embodiments of the invention, the sixth aspect is combined with the fifth aspect and/or with the first aspect.

In embodiments of the first, fifth, and/or sixth aspect, and also in embodiments of the fourth aspect, a special group of embodiments concerns spine stabilization devices that comprise a fixation device with a fixation device body that has a plurality of receiving openings and a plurality of fasteners (anchors) that comprise material—for example thermoplastic material—that is liquefiable by the impact of energy, such as mechanical energy (mechanical vibrations or other energy such as the mechanisms disclosed in U.S. patent application 61/175,947 incorporated herein by reference, or radiation energy etc. The fasteners may be introduced through the receiving openings and anchored in the bone tissue of the respective vertebral body.

In a first group of embodiments, the fasteners comprise tube elements, each suitable for being inserted into one of the receiving openings and for constituting, together with an anchoring material element, one of the anchors. The anchoring material element is at least partially liquefied while energy impinges and while it is pressed towards the distal side, so that liquefied anchoring material is pressed out through the opening(s) and into bone tissue. Thereafter, the anchoring material liquefies and thereby anchors the tube element in the bone tissue.

Each of the tube elements defines a cavity open towards a proximal material introduction side, and at least one opening where the cavity opens towards a bone side. Lateral openings or openings that may be radial or that may be at an angle to a radial direction (for example towards the distal side) are possible. Lateral openings that are at an angle to the radial direction (which angle may for example be greater than 0° and up to 60°, especially around 45°) feature the advantage that an axial load on the tube element—to which the anchor may be subject often—does not cause a pure shear force on the anchoring material, whereby the stability may be superior. The tube elements may be closed off towards the distal side, or may comprise a distal opening (being the opening or, in addition to lateral openings, one of the openings) through which material portions may penetrated into the bone tissue, which distal opening, however, is substantially smaller than the proximal material receiving opening. Further features and advantages of configurations with tube elements can be found in U.S. patent application 61/259,383 incorporated herein by reference. Also a distal opening, through which anchoring material is pressed out, may improve the stability with respect to axial forces acting on the tube element.

Like in other embodiments not comprising the tube elements, the anchoring material may be provided in the form of an initially solid, liquefiable element, especially a thermoplastic element. The liquefaction may take place by energy impinging from a proximal side onto the liquefiable element, such as by mechanical vibration, or possibly a rotational movement, or irradiation by electromagnetic energy, etc.

The tube elements may have one, two, three four or more lateral openings that may be equally distributed along the circumference of the tube element, or may be arranged at non-equal distances.

Optionally, the tube elements may have a distal self-reaming structure, as for example taught in WO 2005/079 696. For example, the tube elements may have a blade-like feature that may be distally of at least one of the openings through which the anchoring material exits. Often, the bone tissue in vertebral bodies—when a fastener is introduced from the ventral side—is increasingly softer towards the distal side.

In such situations—or also if no self-reaming structure is present, a sub-cortical or even cortical anchoring may be advantageous, i.e. the openings are arranged in vicinity to the cortical bone and preferably slightly distally thereof. By this, the anchoring material after exiting through the openings and re-solidifying is firstly anchored in more dense and thus more stable bone tissue and secondly, together with the cortical bone, forms a blind rivet like anchoring feature that is very stable against pulling forces. However, due to the reduced depth of the anchoring location, the lever for resisting pivoting movements is reduced. The combination with a structure that protrudes distally more into the bone tissue provides additional stability against such movements.

Generally, a sub-cortical anchoring may for example be obtained if a distance between an outer surface of the bone tissue and the proximal end of an opening through which the anchoring material exits from the elongate cavity is for example between 2 mm and 7 mm, especially between 3.5 mm and 5.5 mm (this being quantities that hold for grown-up persons). Accordingly, a distance between a distal end face of an implant portion resting against the bone tissue (such as a fixation device body of a spine stabilization device) and the proximal onset of the opening can be chosen to be of the same order, i.e. between 2 mm and 7 mm, especially between 3.5 mm and 5.5 mm.

A length (proximodistal extension) of the opening(s) through which the anchoring material exits may be between 1 mm and 6 mm, especially between 2.5 mm and 5 mm. Experiments with sub-cortical anchoring (in vertebral body bone tissue) have shown that for a plurality (for example four) holes equally distributed in the circumferential dimension an anchoring material ring of a proximodistal extension corresponding to the according extension of the openings and of a diameter of 10 mm surrounding a tube element of 4 mm diameter could be obtained.

In embodiments that deal with spine stabilization devices having an intervertebral spacer and in relation to a lateral extension of the vertebral body, sub-cortical anchoring is achieved if the depth at which the anchoring material exits is between about 5% and 20% of the extension of the vertebral body.

Further, it may be advantageous to make such a structure less stiff and more flexible than the often very stiff tube shape, for example by making it blade-shaped. A too high stiffness can be problematic in situations where it is not desired to fully transmit every momentum acting on the fastener onto the bone trabeculae but to absorb some by a some elasticity of the fastener. A blade shape may by more flexible than a tube shape. Also, a blade shape, for which no opening in the bone tissue has to be pre-made during surgical insertion is less of an exposure of the bone tissue than a tube shape reaching further distally would be.

When the tube elements comprise a plurality of lateral openings, they may in accordance with a further option comprise a directing structure structured angularly with respect to a longitudinal axis of the cavity to direct different portions of the liquefiable material to different ones of the lateral openings. The directing structure may include a directing structure body terminating the cavity distally and a separating portion protruding proximally from the directing structure body. Such a separating portion may comprise at least one wall protruding proximally from the directing structure body. A wall of this kind may extend from between the holes or two of the holes to a center of the longitudinal opening.

As an alternative to the fasteners each comprising a tube element and an anchoring material element, in an second group of embodiments, the fasteners may be fasteners of the kind disclosed in WO 02/069 817 or WO 2004/017 857. For example, the fasteners may consist of a thermoplastic fastener element that has a pin-shaped portion, and at least portions of which are liquefiable by the impact of energy, for example mechanical vibrations. In this, the thermoplastic material of the fastener element may be resorbable or non-resorbable. As an other example, the fasteners may comprise a non-liquefiable core and peripheral liquefiable material portions. Such peripheral liquefiable material portions may be resorbable or non-resorbable. Surface portions not covered by the liquefiable material portions may comprise a surface that advances osseointegration.

Also fasteners of this second group of embodiments may comprise self-reaming structures, as for example taught in WO 2005/079 696.

As still further alternatives the fasteners may be of the kind disclosed in WO 2008/034 277, WO 2009/055 952, WO 2009/132 472, or WO 2009/109057, all incorporated herein by reference in their entirety. Especially, in embodiments, elements may be used that are, while energy impinges to liquefy the anchoring material, pulled or pressed towards the proximal side while a counter force acts towards the distal side. Such embodiments may—like embodiments comprising the tube elements—be advantageous in situations where the bone tissue is not to be subject to mechanical load during implantation.

In addition, in all embodiments an opening in the bone tissue of the vertebral body may be subject to an augmentation treatment prior to the insertion of the fastener. Such an augmentation treatment may comprise augmenting the tissue by pressing thermoplastic material, in a liquid state, into pores of a wall of the opening of the bone tissue to strengthen the bone tissue. Especially, a method and devices as taught in PCT/CH 2009/000339 or U.S. patent application 61/259,383, both incorporated herein by reference in their entirety, may be used. As an alternative to the methods taught in PCT/CH 2009/000339, a thermoplastic augmentation element during the augmentation treatment may also be pressed, by a vibrating ring sonotrode, towards the distal side and against a distal end of the opening in the bone tissue.

In all embodiments, the fixation device body may for example be essentially plate-shaped with lugs that may protrude, in the superior and inferior direction, respectively, from an essentially rectangular basic shape of the fixation device body and that also protrude above and below the intervertebral spacer (interbody spacer). The lugs form the receiving openings for the anchors (fasteners). For example, four lugs may be present, two protruding above the intervertebral spacer and two protruding below (2+2 configuration). As an alternative (in embodiments with or without the lugs), 2+1, 1+2 (for example for cervical applications) or 1+1 (for example XLIF, TLIF) configurations are possible, as well as configurations with more than 2 upper and/or lower receiving openings. The lugs may be in a plane defined by the fixation device body's plate-shaped portion, or they may be angled with respect to that plane, for example away from the interbody spacer and the vertebral bodies.

The fixation device body (or the plate-like, flat portion thereof) may have a curvature. For example the fixation device body may be concave, flat or convex; combined (for example saddle-like) curvatures are not excluded. Especially, for example, in a section with the median plane, the fixation device body may be concave so that a the lateral portions of the fixation device body are more proximal—which is for example advantageous in cases where it is desired not to remove too much tissue of the vertebral bodies but to nevertheless have the entire device countersunk in the intervertebral space as much as possible. Also flat configurations (in section with the median plane) or even convex configurations may be used.

The receiving openings may have a guiding function for the tube elements or other fasteners. In this, they may, in addition to providing support against a backout movement (a movement of the support portion away from the vertebral body) also a definition and stabilization of the angle of the fastener with respect to the support portion. For example, the receiving openings may cooperate with the fastener (especially, with a proximal shaft portion thereof) to form an angle defining fit. Especially, if the fastener comprises a tube element or possibly a counter element and an anchoring material element liquefiable by impinging energy, such as mechanical oscillation, the tube element (or counter element) may be introduced in the receiving opening by a non-rotational movement (such as a pushing movement).

The tube element (or counter element) may comprise a cylindrical shaft portion, and the receiving opening may define a cylindrical guiding portion, wherein the shaft portion and the guiding portion together define a transition fit or an interference fit or a friction fit or a tight clearance fit such as an h-H tolerance pairing (sometimes the term line-to-line fit is used). An example for a fit between the cylindrical guiding portion and the shaft portion are +0.006/0 (H6) for the opening and 0/−0.006 (h6) for the shaft portion. An other example is +0.006/0 for the receiving opening and +/−0.004 for the shaft portion. Especially preferred are h-H pairings and transition fits.

The angle defining fit is advantageous in combination with fasteners that are—in contrast to screws—not subject to a rotational movement when inserted. The concept of anchoring a fastener in tissue by means of liquefying material, pressing at least portions of it into the tissue and then letting the material re-solidify—especially in accordance with the first aspect of the invention—is especially suited in combination with the angle definition/stabilization by means of a fit of the above-discussed kind.

In embodiments with an angle defining fit, the fixation device body that comprises the support portion and the receiving openings may further comprise a collar portion that protrudes proximally and/or distally from the receiving openings and ensures that the guiding portion is longer than the thickness of the plate or other shape that forms the support portion or the receiving openings. For example, such a collar portion may protrude distally towards the vertebral body. When embodiments with a collar portion protruding distally are surgically inserted, the vertebral body tissue may be locally removed—for example it may be 'opened' by a local cortical bone tissue removal—to make room for the collar portion, and/or the collar portion may be pressed into the tissue.

In addition to being suitable of defining a very precise fit, the cylindrical shaft and guiding portions also co-operate to provide a self-cleaning connection.

Instead of cylindrical shaft and guiding portions, an angle defining fit may also be also be caused by conical shaft and guiding portions, for example having the shapes of Morse tapers.

In addition to the angle defining fit, the device according to aspects of the invention may also comprise other angle stabilization and fixation means such as angle stabilization and fixation means according to the state of the art.

It is further (as an alternative to the angle defining fit or in addition thereto) possible to provide the receiving openings with a joining location that comprises structures, for example undercut structures. The fasteners may then have a matched joining location with thermoplastic material, for example the anchoring material. After energy has impinged on the respective fastener, the joining location and the matched joining location together form a connection, as for example taught in WO 2008/034 276 incorporated herein by reference. It would according to yet another alternative be possible to provide a thermoplastic coating of the receiving openings' guiding surfaces that welds to thermoplastic material of the fasteners and/or that interpenetrates non-liquefiable structures of the anchoring material to form a matched joining location as taught in WO 2008/034 276.

As discussed referring to the fifth aspect of the invention, the receiving openings may be adapted to guide the tube elements at a nonzero angle to the sagittal plane and/or at a nonzero angle to a median plane (in the latter case, the superior and inferior tube elements are, in a projection onto the sagittal plane, non-parallel with respect to each other). Such zero or non-zero angles may be present also in embodiments with less than four fasteners (such as 1+1 or 2+1 configurations) or with more than four fasteners. For example, the angle to the median plane may be between 10° and 40°, especially between 15° and 35° or between 20° and 30°.

While in embodiments of the fifth aspect of the invention as well as in embodiments of other aspects of the invention, the fasteners penetrate the cortical bone of the vertebral bodies at their circumferential surface leaving the endplates intact, it is also possible to introduce fasteners through the endplates. While, depending on the actual configuration, a damaging of the endplates may be disadvantageous, and the introduction angle may be unfavorable such anchoring through the endplates may also be beneficial in certain situations. Especially, subcortical anchoring through the endplates may provide strong stability against pulling forces. A method of implanting a spine stabilization device according to the fifth aspect and/or of the sixth aspect of the invention may comprise positioning an interbody spacer template or an interbody spacer between the vertebral bodies, with a cutter guiding tool in a defined position relative to the interbody spacer template or interbody spacer, of using a punching device for punching out a portion of the cortical bone of the vertebral body from an anterior side thereof, the punching tool guided by the cutter guiding tool.

The method may comprise, after positioning of the interbody spacer and the fixation device's support portion, the further step of inserting the fastener by means of a positioning and/or implanting device, which implanting device is guided at two points at an axial distance from each other, a first point being defined by the fastener receiving openings, and a second point being defined by an aiming tool arranged proximally of the support portion and at a distance thereto.

Such a two point guiding principle—the two point may be at a substantial distance of up to several centimeters from each other—makes a precise definition of insertion angles of the fasteners possible, it is often more precise than using a gauge with a cylindrical guiding portion as in state-of-the art approaches.

Further, the method may comprise, after the punching out and, as the case may be, prior to the insertion of the fastener, the step of preparing an opening for the fastener by a guided awl device.

Preferred embodiments of the methods of the invention further comprise inserting the fastener by impinging a momentum and/or energy upon the fastener by means of a tool that is shielded by a guiding tube and/or does not comprise any momentum and/or energy deflecting means.

The invention concerns also a first kit of parts for preparing an implantation of a spine stabilization device, and a second kit of parts comprising a spine stabilization device and a first kit of parts.

Generally, a kit of parts for preparing and/or carrying a surgical operation with a spine stabilization device according to any aspect of the invention may comprise a fastening instrument and/or instrumentation for preparing the spine for operation (including, for example, a cutting/punching tool for removing a flake of cortical bone tissue). In all embodiments, the parts may be present in one or more sterile packages.

A special aspect of the invention deals with at least partially automated anchoring of a spinal implant or other implant in a surgical operation. In accordance with this special aspect, a kit of parts for preparing and/or carrying a surgical operation comprises, possibly in addition to the implant itself:

an automated insertion apparatus or handpiece, comprising a housing, an ultrasonic converter operable to generate mechanical vibrations the converter being mounted inside the casing to be displaceable in a longitudinal (proximodistal) direction relative to the housing, a sonotrode couplable (and for example coupled) to the converter, a mechanism for pushing the converter and the sonotrode to the distal direction, a guiding tube (or shaft) that may be coupled to the housing and within which the sonotrode and/or an anchoring material element may be guided so that any tissue that might come into contact with the arrangement is protected from the vibrations generated by the converter and transmitted via the sonotrode, and an aiming device to which the guiding tube may be coupled so as to define a guiding tube direction with respect to the implant.

If the fastener by which the implant is anchored is of the kind comprising a tube element (for example of any kind described in this text), then the kit may further comprise one or more of the tube elements. A distal end of the guiding tube may either be couplable to the tube element (if present) or may be couplable to a guiding portion (such as a fixation device body receiving opening) of the implant.

Depending on the depth of the tube element cavity (or other elongate cavity from which the anchoring material exits into the tissue), it may be preferable to insert the anchoring material element only after the tube element (or other elongate cavity) is coupled to the guiding tube. For these embodiments—and optionally also for other embodiments—it may be advantageous to provide a quick connector between the handpiece and the guiding tube so that optionally the anchoring material element may be introduced into the elongate cavity through the guiding tube after the guiding tube has been mounted to the tube element or other element comprising the elongate cavity. Thereafter, the sonotrode may be introduced through the guiding tube, the sonotrode either being pre-assembled with the handpiece or being assembled with the handpiece after it is inserted in the guiding tube. The quick connector is then used to couple the guiding tube to the handpiece. Such a quick connector may optionally also be present when the anchoring material element is introduced in the elongate cavity before the guiding tube is mounted.

The aiming device is preferably affixed to a distance holding device—such as a handle device—at a distance to the entry of the elongate cavity (for example at a distance to the interbody spacer). The aiming device and the structure to which the distal end of the guiding tube is coupled together fully define the direction of the guiding tube and thus the insertion direction.

Preferably, there are means for causing the axis of the elongate cavity to coincide with the axis of the guiding tube. For example, the tube element that defines the elongate cavity may be guided by an appropriate angle defining guidance, for example as explained elsewhere in this text. In addition or as an alternative, a pre-made bore in the tissue may have the same axis, for example by the aiming device or an analog aiming device being used during drilling of the bore.

Preferably, the housing, the guiding tube and the elongate cavity (and potentially other protecting elements) in the coupled state together form an assembly that completely shields the outside from the mechanical vibrations or other mechanical movements so that no moving parts can come into contact with tissue. In all aspects of the invention, embodiments include introducing the fixation device(s) and where applicable also the anchoring material elements and/or the anchoring device essentially in a direction parallel to the median plane of the interbody spacer (and for example deviating not more than 20°, 15° or 10° from it; this includes 'negative' angles, configurations in which the fasteners point towards each other instead of pointing away from each other or being parallel to each other). This may allow a comparably easy access of instruments. This is advantageous not only for implantation from the anterior but also from the lateral and anterio-lateral direction, as well as more dorsal directions.

Mechanical vibration or oscillation suitable for the method according to embodiments of the invention that include liquefaction of a polymer by friction heat created through the mechanical vibration has preferably a frequency between 2 and 200 kHz (even more preferably between 10 and 100 kHz, or between 20 and 40 kHz) and a vibration energy of 0.2 to 40 W, especially 0.2 to 20 W or 10 W to 35 W for special applications (for example if the fastener comprises a tube element and a thermoplastic anchoring material element) per square millimeter of active surface.

The vibrating element is e.g. designed such that its contact face oscillates predominantly in the direction of the element axis (longitudinal vibration) and with an amplitude of between 1 and 100 µm, preferably around 10 to 30 µm or around 20 to 40 µm for applications with a tube element. Rotative or radial oscillation is possible also.

For specific embodiments of the spine stabilization device it is possible also to use, instead of mechanical vibration, a rotational movement for creating the named friction heat needed for the liquefaction of the anchoring material. Such rotational movement has preferably a speed in the range of 10'000 to 100'000 rpm. A further way for producing the thermal energy for the desired liquefaction comprises coupling electromagnetic radiation into one of the device parts to be implanted and designing one of the device parts to be capable of absorbing the electromagnetic radiation, wherein such absorption preferably takes place within the anchoring material to be liquefied or in the immediate vicinity thereof. Preferably electromagnetic radiation in the visible or infrared frequency range is used, wherein the preferred radiation source is a corresponding laser. Electric heating of one of the device parts may also be possible.

While the principles of the aspects 1 through 6 of the invention are primarily described referring to a spine stabilization device with an interbody spacer and a fixation device, where the interbody spacer is assumed to be dimensionally stable, the approach of the first, third, fifth and sixth aspects as well as advantageous features and embodiments thereof can also be used for other configurations.

A first group of such alternative configuration are configurations where the fixation device or fixation devices are used to hold in place an intervertebral disc prosthesis. Such an intervertebral disc prosthesis is distinct from a dimensionally stiff intervertebral spacer in that it forms an articular joint between the vertebral bodies. By this, transverse forces may cause a relative movement and additional loads compared to the stiff interbody spacer. In such alternative configurations of the first group, the fixation device should not comprise a plate-like fixation device body that connects the upper and lower vertebral bodies by being a dimensionally stiff body attached to both vertebral bodies. Rather, the fixation device may comprise two fixation device portions, one to be attached to the upper vertebral body and equipped for holding an upper end element (such as an endplate) of the prosthesis, and the other one to be attached to the lower vertebral body and equipped for holding a lower end element of the prosthesis. The fixation device portions in this may optionally belong respective end elements of the prosthesis.

In the first group of such alternative configurations, the teaching relating to an 'interbody spacer' in the above-discussed and hereinafter further described embodiments is to be replaced by a different kind of implant, namely an intervertebral disc prosthesis.

A second group of such alternative configurations are configurations with an interspineous spacer. Such an interspineous spacer is inserted between the posterior spineous processes. Interspinous spacers are known in the art. The concept of the second group of alternative configurations proposes to use the fastening technology with one or more fixation devices to the spinal column, especially the spinal processi.

In the second group of such alternative configurations, the teaching relating to an 'interbody spacer' in the above-discussed and hereinafter further described embodiments is to be replaced by yet an other kind of implant, namely an interspineous spacer, and instead of in the vertebral bodies, anchoring occurs preferably in the spinal processi.

In a third group of alternative configurations, the teaching of the first or third aspect of the invention and possibly advantageous features and embodiments thereof is used for attaching a plate or a plate system to bone tissue. For example, a plate may stabilize two vertebrae with respect to each other (for example similar to a configuration with an interbody spacer, but without replacing the natural intervertebral disc by the interbody spacer, or while the intervertebral disc is by loose bone graft or the like). Alternatively, such a plate may stabilize other bone elements with respect to each other, including a fracture.

In the third group of such alternative configurations, the teaching relating to a 'fixation device' in the above-discussed and hereinafter further described embodiments is to be replaced by a fixation device that is not used to fix an interbody spacer but that itself is stabilizing, and instead of in the vertebral bodies, anchoring may occur at an other part of the skeleton.

In a fourth group of alternative configurations, the teaching of the first or third aspect of the invention and possibly advantageous features and embodiments thereof is used for holding in place, instead of an interbody spacer, an other prosthetic load transmitting element, such as a defect bridging, an arthrodesis element, an interpositional prosthesis, a joint prosthesis etc.

In the fourth group of such alternative configurations, the teaching relating to an 'interbody spacer' in the above-discussed and hereinafter further described embodiments is to be replaced by yet an other kind of implant, namely the prosthetic load transmitting element, and instead of in the vertebral bodies, according other elements of the skeleton are used for anchoring.

In embodiments of the first aspect of the invention as well as in alternative configurations of the above-discussed kind, a surgical device is provided comprising a fixation device, the fixation device comprising:
- a fixation device body with a rigid portion and at least one receiving opening, and
- at least one fastener for being inserted in the receiving opening, the fastener comprising an anchoring material portion that is configured to be inserted, in a liquid state, into bone tissue to which the fixation device is to be fixed, to thereby infiltrate the bone tissue, and to harden thereafter so as to fix the fastener to the bone tissue,
- wherein the at least one fastener co-operates with the fixation device body to hold the fixation device body to the bone tissue when the fastener is fixed to the bone tissue.

In this, the fixation device body may constitute an implant such as a fixation plate or an intervertebral disc implant or an arthordetic device or any other device, for example of the hereinbefore discussed kind. The fixation device body may, as in other discussed examples be an auxiliary device for holding an implant, such as an interbody spacer, in place.

In embodiments of the surgical device, the receiving openings comprise an inner guiding surface that co-operates with an outer guiding surface of the fastener to define an angle stabilizing guidance. Especially, the angle stabilizing guidance may be an angle defining fit of as discussed hereinbefore.

The at least one fastener may be a fastener that comprises a tube element with one or more openings through which the anchoring material exits during the anchoring process, and/or it may be of any (other) kind of a fastener based on liquefied and re-solidified anchoring material that interpenetrates structures of the bone tissue, based on principles described hereinbefore or as described hereinafter.

Embodiment of the surgical device comprise the features of the fixation devices and/or of the fasteners described referring to any spine stabilization device in accordance with aspects 1, 2, 3, 5, and 6 of the invention.

In this text the expression "thermoplastic material being liquefiable e.g. by mechanical vibration" or in short "liquefiable thermoplastic material" or "liquefiable material" is used for describing a material comprising at least one thermoplastic component, which material becomes liquid or flowable when heated, in particular when heated through friction i.e. when arranged at one of a pair of surfaces (contact faces) being in contact with each other and vibrationally or rotationally moved relative to each other, wherein the frequency of the vibration is between 2 kHz and 200 kHz, preferably 20 to 40 kHz and the amplitude between 1 μm and 100 μm, preferably around 10 to 30 μm (or around 20 to 40 μm). Such vibrations are e.g. produced by ultrasonic devices as e.g. known for dental applications. For being able to constitute a load-bearing connection to the tissue, the material has an elasticity coefficient of more than 0.5 GPa, preferably more than 1 GPa and a plastification temperature of up to 200° C., of between 200° C. and 300° C. or of even more than 300° C. In applications where the anchoring material is provided in a supporting, load bearing structure, especially a tube element of the hereinbefore-discussed kind, the elasticity coefficient (especially Young's Modulus) may also be lower than 0.5 GPa, for example 0.08 GPa or more, especially at least 0.1 GPa, for example between 0.1 GPa and 2 GPa. In such applications, the where the anchoring material is provided in a supporting, load bearing structure, the anchoring material may optionally be entirely liquefied during the anchoring process (and not only in regions close to the surface) and thus does not necessarily have to transmit vibrations to the periphery. An example of an anchoring material suitable for such applications are thermoplastic elastomers. A specific example is a thermoplastic polyurethane elastomers, for example Pellethane® by Dow Chemicals.

Depending on the application, the liquefiable thermoplastic material may or may not be resorbable. Suitable resorbable polymers are e.g. based on lactic acid and/or glycolic acid (PLA, PLLA, PGA, PLGA etc.) or polyhydroxyalkanoates (PHA), polycaprolactones (PCL), polysaccharides, polydioxanones (PD), polyanhydrides, polypeptides or corresponding copolymers or blended polymers or composite materials containing the mentioned polymers as components are suitable as resorbable liquefiable materials. Thermoplastics such as for example polyolefins, polyacrylates, polymetacrylates, polycarbonates, polyamides, polyesters, polyurethanes, polysulphones, polyaryl ketones, polyimides, polyphenyl sulphides or liquid crystal polymers (LCPS), polyacetals, halogenated polymers, in particular halogenated polyoelefins, polyphenylene sulphides, polysulphones, polyethers, polypropylene (PP), or corresponding copolymers or blended polymers or composite materials containing the mentioned polymers as components are suitable as non-resorbable polymers.

Specific embodiments of degradable materials are Polylactides like LR706 PLDLLA 70/30, R208 PLDLA 50/50, L210S, and PLLA 100% L, all of Böhringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in CA Bailey et al., J Hand Surg [Br] 2006 April; 31(2):208-12.

Specific embodiments of non-degradable materials are: Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene. An overview table of polymers and applications is listed in Wintermantel, page 150; specific examples can be found in Wintermantel page 161 ff. (PE, Hostalen Gur 812, Höchst AG), pages 164 ff. (PET) 169ff. (PA, namely PA 6 and PA 66), 171 ff. (PTFE), 173 ff. (PMMA), 180 (PUR, see table), 186 ff. (PEEK), 189 ff. (PSU), 191 ff. (POM—Polyacetal, tradenames Delrin, Tenac, has also been used in endoprostheses by Protec).

Examples of suited thermoplastic material include polylactides such as any one of the products LR708 (amorphous Poly-L-DL lactide 70/30), L209 or L210S by Böhringer Ingelheim or polycarbonates.

The liquefiable material having thermoplastic properties may contain foreign phases or compounds serving further functions. In particular, the thermoplastic material may be strengthened by admixed fillers, for example particulate fillers that may have a therapeutic or other desired effect. The thermoplastic material may also contain components which expand or dissolve (create pores) in situ (e.g. polyesters, polysaccharides, hydrogels, sodium phosphates) or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed.

If the liquefiable material is to be liquefied not with the aid of vibrational energy but with the aid of electromagnetic radiation, it may locally contain compounds (particulate or molecular) which are capable of absorbing such radiation of a specific frequency range (in particular of the visible or infrared frequency range), e.g. calcium phosphates, calcium carbonates, sodium phosphates, titanium oxide, mica, saturated fatty acids, polysaccharides, glucose or mixtures thereof.

Fillers used may include degradable, osseostimulative fillers to be used in degradable polymers, including: β-Tricalciumphosphate (TCP), Hydroxyapatite (HA, <90% crystallinity; or mixtures of TCP, HA, DHCP, Bioglasses (see Wintermantel). Osseo-integration stimulating fillers that are only partially or hardly degradable, for non degradable polymers include: Bioglasses, Hydroxyapatite (>90% cristallinity), HAPEX®, see SM Rea et al., J Mater Sci Mater Med. 2004 September; 15(9):997-1005; for hydroxyapatite see also L. Fang et al., Biomaterials 2006 July; 27(20):3701-7, M. Huang et al., J Mater Sci Mater Med 2003 July; 14(7):655-60, and W. Bonfield and E. Tanner, Materials World 1997 January; 5 no. 1:18-20. Embodiments of bioactive fillers and their discussion can for example be found in X. Huang and X. Miao, J Biomater App. 2007 April; 21(4):351-74), J A Juhasz et al. Biomaterials, 2004 March; 25(6):949-55. Particulate filler types include: coarse type: 5-20 μm (contents, preferentially 10-25% by volume), submicron (nanofillers as from precipitation, preferentially plate like aspect ratio >10, 10-50 nm, contents 0.5 to 5% by volume).

More generally liquefaction in these embodiments is achieved by using materials with thermoplastic properties having a melting temperature of up to about 350° C. If a liquefaction interface or one of a plurality of liquefaction interfaces is situated between a device part comprising the liquefiable material and a counter element, the modulus of elasticity of the liquefiable material should be at least 0.5 GPa so that the liquefiable material is capable of transmitting the ultrasonic oscillation with such little damping that inner liquefaction and thus destabilization of the named device part does not occur, i.e. liquefaction occurs only where the liquefiable material is at the liquefaction interface. If only the interface to the oscillation tool serves as the liquefaction interface, the material may in principle also have a lower modulus of elasticity. However, for some applications, due to the load bearing function the material has, also in this situation, a preferred modulus of elasticity of at least 0.5 GPa. As discussed hereinbefore, the modulus of elasticity may be lower than 0.5 GPa if the applications where the anchoring material is provided with an additional supporting, load bearing structure, such as a tube structure.

The invention also concerns method of implanting a spine stabilization device, and kits of parts that include a spine stabilization device and further includes instruments for their implantation, as described in more detail referring to some of the drawings.

BRIEF DESCRIPTION OF THE DRAWINGS

In the following, embodiments of the invention are described with reference to drawings. The drawings are all schematic and not to scale. In the drawings, same reference numerals denote same or analogous elements. The drawings show:

FIGS. 10-29 further embodiments of the invention incorporating at least the first aspect of the invention and partly also incorporating the second aspect of the invention;

FIGS. 38 and 39 a further embodiment of a spine stabilization device;

FIGS. 40 and 41 an embodiment of a spine stabilization device that is in accordance with the fourth aspect of the invention;

FIGS. 60-66 tools and steps for performing the anchoring process in accordance with the first aspect of the invention;

DESCRIPTION OF THE PREFERRED EMBODIMENTS

Figure 1:
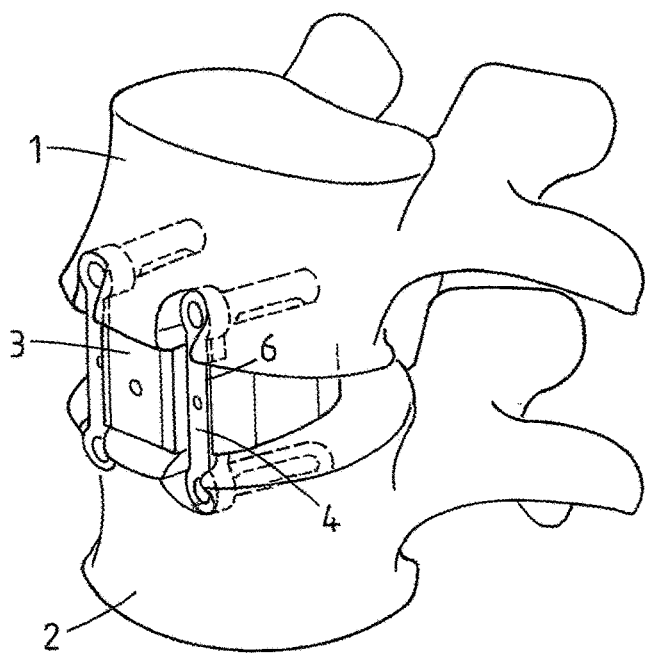
FIGS. 1-7 elements of a first embodiment of the invention incorporating both, the first aspect and the second aspect of the invention.

FIG. 1 depicts an embodiment of a spine stabilization device inserted in a human spine. More concretely, the figure shows an upper vertebra 1 and a lower vertebra 2, between which the intervertebral disc has been at least partly removed. The device comprises an interbody spacer 3 between the vertebral body of the upper vertebra and the lower vertebra. The interbody spacer serves as a distance holder between the upper and the lower vertebral body. The interbody spacer after the surgical insertion between the vertebral bodies is held in place by two fixation devices 4. The fixation devices 4 each comprise two anchors anchoring them in the upper and the lower vertebral body respectively. Further, they each comprise a support portion 6 securing the interbody spacer 3 against movement towards the ventral direction.

Figure 2:
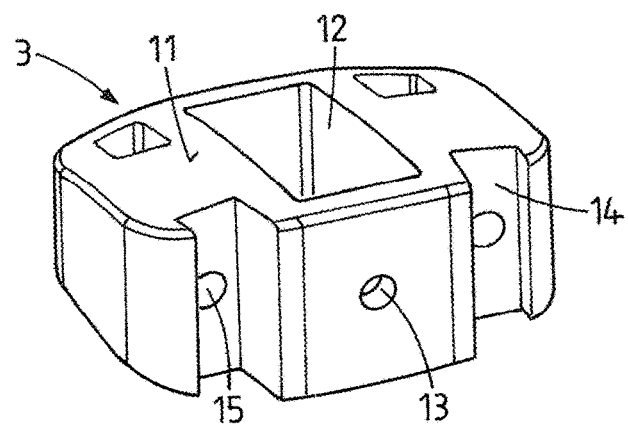
Figure 3:
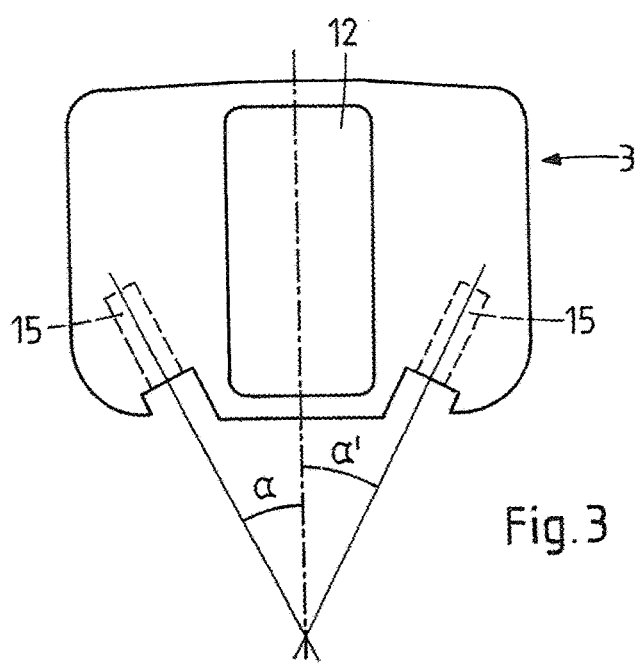

FIGS. 2 and 3 depict the interbody spacer 3 in somewhat more detail. The interbody spacer may be made of any suitable material including PEEK, potentially coated by Hydroxylapatite (HA) for better bone ongrowth and long-term stability. It may alternatively be made of a different biocompatible material suitable for an intervertebral implant, such as an other plastics, a ceramics, or Titanium, also potentially coated.

The interbody spacer 3 comprises a top surface 11 and an opposite bottom surface for being in contact with the lower endplate of the upper vertebral body and the upper endplate of the lower vertebral body, respectively. The interbody spacer further comprises longitudinal (relating to the spine axis) through openings 12 permitting bone growth between the upper and lower vertebral bodies. When the interbody spacer 3 is inserted surgically, the openings may be filled by bone graft and/or bone growth promoting material (for example Bone Morphogenetic Proteins (BMP)). In the depicted configuration, the interbody spacer comprises one through opening that is centrally located with respect to the sagittal plane, however, the approach according to aspects of the invention is not restricted to a particular number and arrangement of the longitudinal through openings. For example, it would also be possible to have a plurality of (for example two) through openings, or one opening or a plurality of openings more on a lateral (with respect to the sagittal plane) position, etc. The aspects of the invention also work if no through opening is present at all, and if for example no interbody fusion by bonegrowth is desired or if the interbody fusion by bonegrowth is only to take place along portions of the circumferential surface of the interbody spacer (for promoting such circumferential bonegrowth, the interbody spacer may in all embodiments of the invention have a reduced transverse extension).

Further, the interbody spacer 3 may be shaped according to the surgeon's needs and comprise retention structures and/or bone ingrowth macroscopic and/or microscopic structures (such as the holes 13 perpendicular to the longitudinal axis depicted in the figure), channels etc. (not shown). In addition, the interbody spacer 3 may be shaped to accommodate corresponding structures of the fixation device(s), such as channel-like recesses 14 that accommodate the support portion of the fixation device. In addition, the interbody spacer 3 in the depicted embodiment comprises holes 15 for the guiding protrusions of the fixation devices, as explained further below.

The fixation devices of the first embodiment comprise a fixation device body 21 and two anchoring material elements 31.

Figure 4:
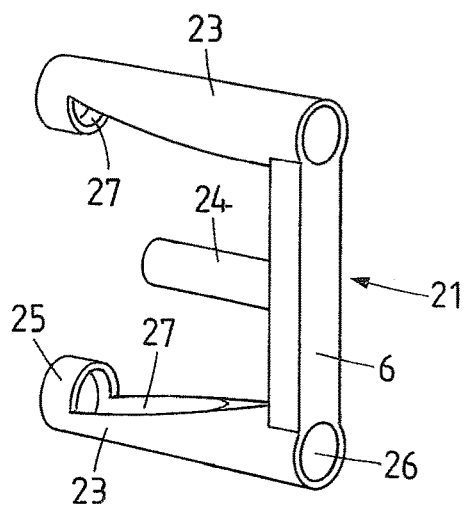
Figure 5:
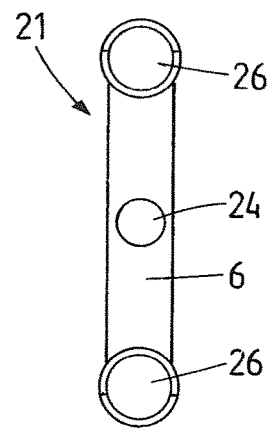
Figure 6:
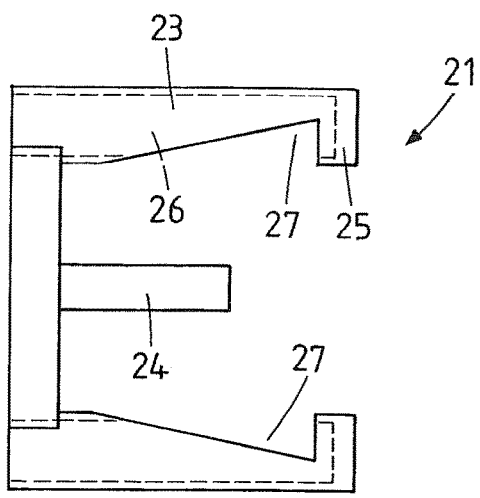

A specimen of a fixation device body 21 is depicted in FIGS. 4-6 showing a perspective view, a front view, and a side view, respectively. The fixation device body in the depicted embodiment has the shape of a staple with an additional guiding protrusion 24 and thus is approximately E-shaped in a side view. The fixation device body comprises the support portion 6 (or crosspiece) and two tube portions 23 that together with the anchoring material elements form the anchors. The tube portions define an elongate cavity. The elongate cavity opens at its first end towards the anterior side so that the anchoring material elements may be inserted into the cavity from the anterior side. Towards the opposite, posterior end the cavity is delimited by the tube portion's base 25. The tube portion further comprises at least one opening 27 that allows a radial (with respect to the axis of the elongate cavity) outflow of the anchoring material in a liquid state. In the depicted embodiment, the only opening of each tube portion 23 is arranged so as to face the respective other tube portion, so that the material may flow downward and upward, respectively, towards the respective vertebral body's endplate.

The tube portions 23 and the guiding protrusion 24 are parallel to each other, i.e. they are insertable into openings with translational symmetry (cylindrical symmetry, for example but not necessarily circular in cross section) with parallel axes. The cylindrical symmetry is optional, instead a conical configuration could be used as well.

While the depicted configuration with the holes 15 diverging is preferred, the same mechanism would also work for converging holes. Further, the approach does not only work for one guiding protrusion 24 (and corresponding hole) per fixation device, but equally well would work with two or even more guiding protrusions, including unequal numbers of guiding protrusions of the fixation devices. Also, using of more than two fixation devices is not excluded.

Figure 7:
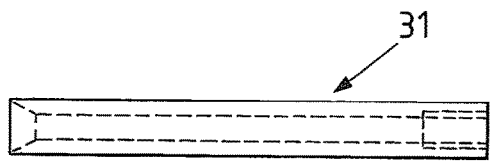
Figure 8:
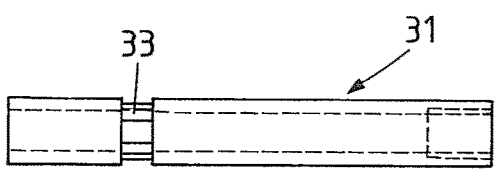
FIG. 8 a variant of an anchoring material element.

FIGS. 7 and 8 depict two versions of an anchoring material element 31. The anchoring material element 31 of FIG. 7 is essentially tube shaped. It for example consists entirely of thermoplastic material, such as a polylactic acid (PLA).

Fixation of the interbody spacer 3 works as follows: After insertion of the interbody spacer, for example by a surgical procedure as such known from the insertion of intervertebral implants such as cages, the fixation devices are fastened to the vertebral bodies. To that end, the tube portions are inserted in pre-drilled bores in the vertebral bodies, which have been made prior to or after the insertion of the interbody spacer 3 (see detailed description further below). The pre-drilled bores and consequently the tube portions after insertion are positioned to go through the cortical bone of the anterior vertebral body circumferential surface portion and into the vertebral body's cancellous bone without any damage done to the cortical bone forming an endplate of the vertebral body. The endplates of the vertebral bodies may thus, without being weakened, entirely contribute to the stability of the configuration after the surgical procedure.

After positioning of the fixation device bodies, the anchoring material elements are inserted and fixed. To that end, the anchoring material elements are pressed against the bases 25 while mechanical vibrations are coupled into them. By the effect of the joint action of the pressing force and the mechanical vibrations, the thermoplastic material at the interface between the anchoring material element 31 and the base 25 is liquefied and pressed radially outward into structures of the (cancellous) bone material surrounding the pre-drilled bore. In this process, the base 25 of the respective tube portion serves as counter element in a process as described and claimed in PCT/CH2008/000452 and U.S. patent application Ser. No. 12/260,698, both incorporated herein by reference in their entirety.

Instead of applying mechanical vibration to the anchoring material element 31, this element may be coupled to a rotation device and rotated while being pressed against base 25 of the tube portion 23, which again results in friction between the distal face of the anchoring material element 31 and the base 25 and provides the heat for the desired liquefaction. Alternatively, laser light preferably of the visible or infrared frequency range may be coupled into the anchoring material element 31, which for absorbing the laser light contains an absorbing agent or a scattering agent which scatters the laser light into the tube portion 23 being designed (e.g. coated on the inside with a metal) to absorb the laser light and to transmit the absorption heat to the anchoring material element 31 for achieving the desired liquefaction. Alternatively, the tube portion 23 may be electrically heated.

Figure 9:
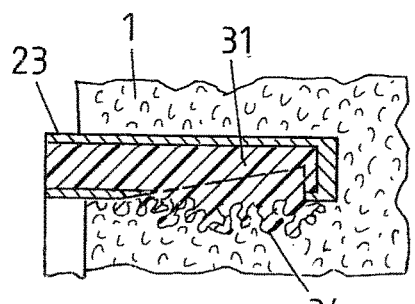
FIG. 9 an embodiment of the anchoring principle.

After re-solidification, the anchoring material pressed radially outward together with the structure of the tube portions forms an anchor of the fixation device 4. This is schematically depicted in FIG. 9, where the liquefied and re-solidified thermoplastic material portions 34 are depicted interpenetrating bone tissue of the vertebra 1.

According to an aspect of the invention, the pre-drilled bores for insertion of the tube portions of the first fixation device 4 and the pre-drilled bores for insertion of the tube of the second fixation device 4 are not parallel but at an angle with respect to each other. This implies that also the holes 15 for the guiding protrusion 24 of the first and of the second fixation device are not parallel but at approximately the same angle with respect to each other as the pre-drilled holes.

FIG. 3 shows a possible arrangement where both holes 15 are at an angle $\alpha$, $\alpha'$ to the sagittal plane (illustrated by the dash-dotted line in the Figure). Whereas the angles $\alpha$, $\alpha'$ are equal in the depicted configuration, this is not a necessity. In the depicted configuration, for clear visibility, the angles $\alpha$, $\alpha'$ are comparably large, and so is the angle $\beta$ between holes 15 (amounting to $\beta=\alpha+\alpha'$). However, in practice the angle between the holes 15 (or their axes) needs not be as high. Preferably, $5°<\beta<150°$, especially preferred $10°<\beta<90°$. As mentioned, the holes need not diverge, as depicted, but may also converge.

Because of the diverging guiding protrusions 24 co-operating with the respective holes 15, the fixation devices not only secure the interbody spacer against movements into a ventral direction (by means of the support portions 6) and into transverse directions (by the guiding protrusions), but also against movements into a dorsal direction. Therefore, the diverging directions of the at least two holes 15 may supersede means for coupling the fixation devices to the interbody spacer, such as screws. This may be an advantage, because screws may loosen, with potentially disastrous consequences. The concept according to the aspect of the invention discussed here makes possible that the entire fixation works without any screws (if the anchoring of the fixation elements is done as discussed above), or at least without any screws that are not in contact with tissue and thus cannot be subject to ingrowth (in case the anchoring of the fixation elements in the intervertebral bodies is achieved by surgical screws).

In addition or as an alternative to the above-discussed fixation mechanism, it is, in different embodiments, also possible to join structures of the fixation device(s) with structures of the interbody spacer by joining matched joining location by the approach disclosed in WO 2008/034 276 or for example by welding.

Figure 22:
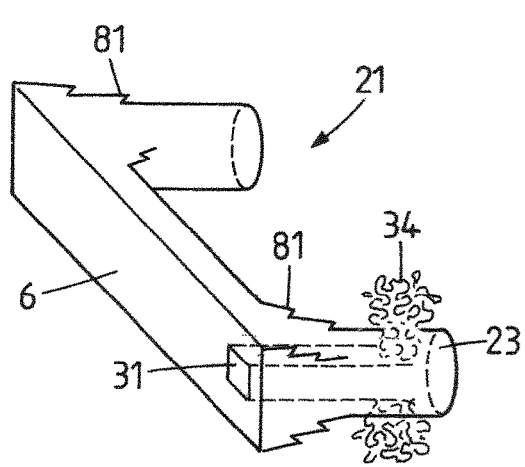
Figure 25:
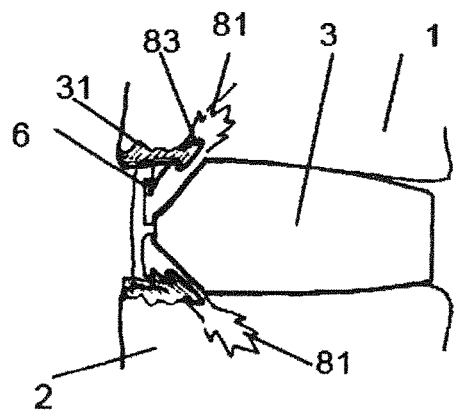

Next, further embodiments being variants of the concept described hereinabove are discussed. The deviations from the above-described first embodiments may be combined with each other to constitute even further embodiments. For example, the shapes of the tube portions of FIG. 12 and/or the bridge portion of the embodiment of FIG. 17 may be used for any one of the other embodiments, the self-reaming structures of the embodiment of FIG. 22 may also be present for other shapes, etc.

Figure 10:
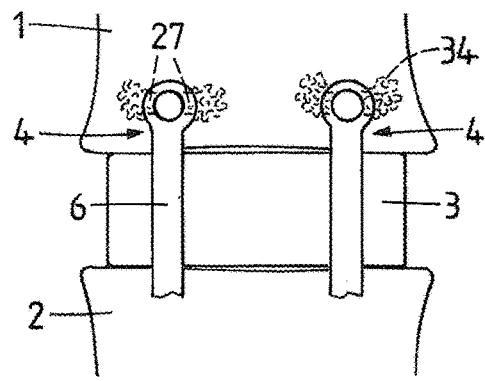

In a first category of alternative embodiments, the tube portion 23 may in addition or as an alternative to the opening facing towards the respective other opening comprise at least one opening facing towards a lateral (transverse) side. An example of such a configuration is depicted in FIG. 10. The tube portion of the fixation device body in the illustrated embodiment comprises two lateral openings 27, through which the anchoring material may exit. The anchoring material portions that interpenetrate bone material after the anchoring process are referenced by number 34 in the drawings. The embodiments that comprise material portions that exit in lateral (transverse) directions have a potential advantage especially in case of brittle bone tissue. The strongest forces upon the connection may be expected to act in the longitudinal direction (with respect to the spine axis). In embodiments with lateral anchoring material flow result in configurations with a higher cross section perpendicular to the longitudinal direction taken up by the anchoring material. Thus, the longitudinal forces are potentially coupled into a larger portion of the bone tissue.

Anchoring material flow in the longitudinal direction may, in contrast, result in an improved support by the respective endplate. Depending on the properties of the actual vertebrae of the patient, lateral flow, longitudinal flow, or a combination of lateral and longitudinal flow may be advantageous, and according arrangements of the openings may be used.

Figure 11:
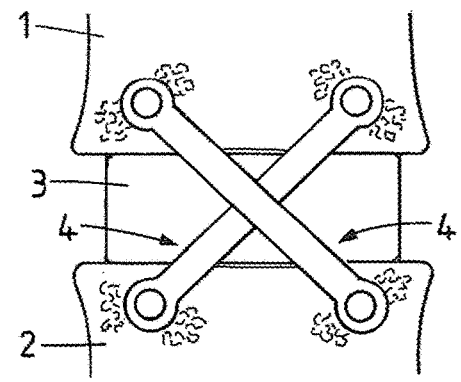

While in the so far discussed embodiments, the support portion is a bridge like portion that is arranged essentially longitudinally, this is not necessary. FIG. 11 illustrates a configuration with support portions 6 that are at an angle to the longitudinal axis, and that furthermore cross each other.

Figure 12:
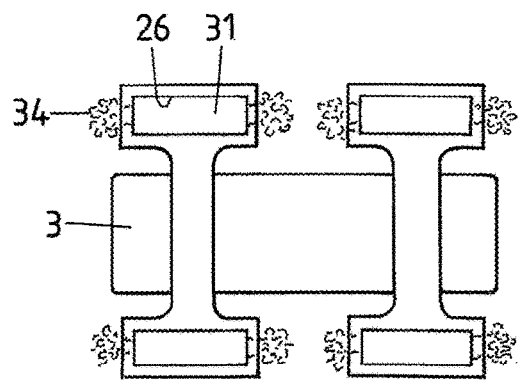

The variant of FIG. 12 is distinct from the one of the previous figures in that the cavity 26 and the anchoring material element 31 are not circular in cross section but, for example, rectangular. Also in the embodiment of FIG. 12, the openings through which the anchoring material exits are arranged laterally.

In the various embodiments, the position of the fixation devices may be defined by according structures (such as a channel like structure and/or the hole for the guiding portion if present) in the interbody spacer 3 and/or by the dimension and shape of the fixation devices themselves.

Figure 13:
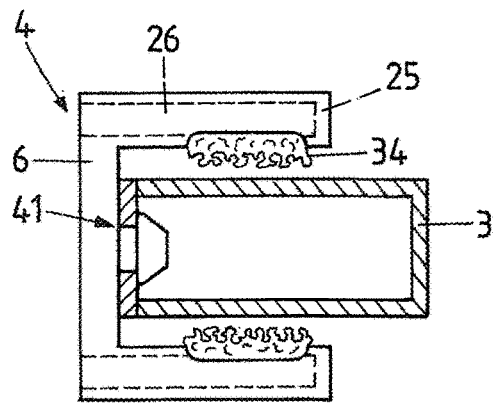
Figure 14:
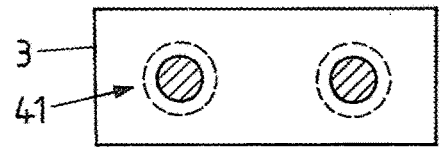

The embodiment of FIGS. 13 and 14, showing a cross section of the spine stabilization device and a front view of its interbody spacer 3, respectively, comprises a coupling means for coupling the interbody spacer 3 to the fixation device. More concretely, the interbody spacer 3 and the fixation devices 4 comprise a snap fit means 41 for securing the interbody spacer and the fixation device with respect to each other. In embodiments with a separate coupling means (as well as if the coupling is not necessary), the guiding pins and the respective holes need not be present.

Also other coupling means, including coupling means that as such are known from the state of the art, may be used, including screws, positive-fit connections etc.

Figure 15:
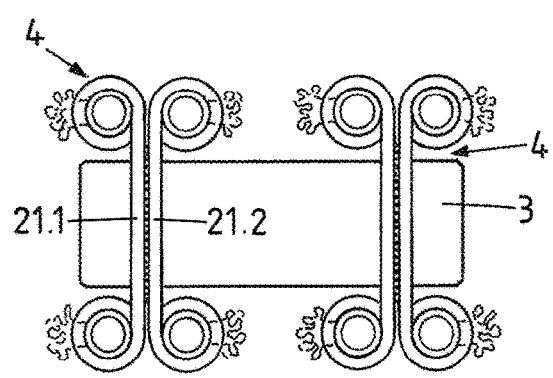

A further embodiment of the spine stabilization device is depicted in FIG. 15. The fixation device bodies are built as comprising two brass pieces 21.1, 21.2 that are bent to form the tube portions at their upper and lower ends and to form approximately straight support portions in an intermediate region. The two brass pieces 21.1, 21.2 are tacked together in the intermediate region. The straight support portions, because of being extended in the direction perpendicular to the drawing plane, also form the guiding portions and cooperate with corresponding slits in the interbody spacer 3.

The embodiment illustrated in FIGS. 16a and 16b is distinct from the one of FIGS. 1-9 in that the tube portions are elements that are initially separate from the fixation device body 21, which includes the support portion 6. To that end, the fixation device body 21 comprises receiving openings 63 for receiving the tube portions or tube elements 51. The tube elements comprise, at their proximal end, a circumferential collar 52 that in the inserted position abuts against a proximal surface of the fixation device body 21 and thereby secures it to the bone tissue. The fixation device body may further comprise a guiding portion and/or coupling means (not shown). FIG. 16a shows the spine stabilization device illustrated in an exploded manner, and FIG. 16b shows the device after insertion and anchoring. In FIG. 16a, also the pre-drilled holes 61 are visible.

FIG. 16a further illustrates an oscillation transmitting device for coupling the mechanical oscillation into the anchoring material element, namely a sonotrode 67. While such a sonotrode is not illustrated in most of the other figures, it goes without saying that a sonotrode may be used to couple mechanical vibrations into the element that comprises the thermoplastic material (if any) during anchoring. In the case of using a rotational movement instead of mechanical vibration, the anchoring material element is coupled to a rotation drive instead of a vibration drive (sonotrode 67). In the case of using electromagnetic radiation and absorption thereof instead of mechanical vibration, the corresponding tool is equipped for transmitting the radiation into the anchoring material element (e.g. comprises a light guide with a distal end at the distal face of the tool) and for pushing the anchoring material element into the tube element. For this purpose the anchoring material element is preferably coupled to the tool which therewith is capable also of positioning the anchoring material element in the tube element.

In the embodiments of FIGS. 16a and 16b, the tube elements 51 and the anchoring material elements 31 together function as anchoring element of the kind comprising an outer sleeve of a non-liquefiable material, and liquefiable material suitable of being liquefied and pressed towards an outside through lateral openings in the sleeve, as for example described in U.S. Pat. Nos. 7,335,205, 6,921,264, U.S. application Ser. No. 12/260,698, and U.S. application Ser. No. 61/049,587. In a first step, preceding the insertion of the tube elements 51, optionally the tissue of the vertebral bodies may be subject to an augmentation treatment. Such treatment may comprise augmenting the tissue by pressing thermoplastic material, in a liquid state, into pores of a wall of the opening of the bone tissue to strengthen the bone tissue. Especially, a method and devices as taught in PCT/CH 2009/000339 or U.S. patent application 61/259,383 may be used, or as an alternative, a thermoplastic augmentation element during the augmentation treatment may also be pressed, by a vibrating ring sonotrode, towards the distal side and against a distal end of the opening in the bone tissue. The augmentation treatments according to these teachings feature introducing instrumentation into the opening of the tissue, and the receiving openings 63 help to guide and position both, the instruments used for augmentation (such as the sonotrode and a counter element or the like), and if necessary, tools for making the opening in the tissue, such as drills etc.

In the embodiment of FIGS. 16a and 16b, the directions of the tube elements (or more generally the anchoring elements) and of the guiding portions (if present) need not necessarily be parallel. For example, the pre-drilled holes for the first and second fixation devices may be parallel, while the guiding portions are still arranged in a non-parallel fashion.

The variant of FIG. 17 comprises a single fixation device with four (instead of two as in the previous figures) anchoring locations. Because of geometric reasons, the variant of FIG. 17 is not suited for the above-described concept that includes guiding portions that diverge (or converge) relative to each other if the tube portions are fixedly attached to the fixation device body 6. However, in embodiments without diverging guiding portions, the spine stabilization device may comprise coupling means (not shown), such as a screw, an other positive-fit connector, or a friction-type connector etc. for coupling the fixation device and the interbody spacer 3 to each other. It would also be possible to fixedly fasten the interbody spacer and the fixation device to one another prior to the insertion of the interbody spacer; this includes making the interbody spacer and the fixation device body of one piece. As an alternative, the guiding portions may diverge also in embodiments like the one in FIG. 17 if the tube portions are not fixedly attached to the fixation device body but introduced in situ as illustrated for the embodiment of FIGS. 16a and 16b.

FIGS. 18 and 19 show yet another embodiment of a spine stabilization device. In contrast to the embodiment of FIGS. 1-9, the fixation devices 4 each comprise two anchoring locations for anchoring the fixation device body in a same vertebral body. The upper fixation device is anchored by means of two tube portions 23 and two anchoring material elements 31 in the upper vertebral body spaced laterally from each other, and the lower fixation device is anchored by means of two tube portions 23 and two anchoring material elements 31 in the lower vertebral body. The pre-drilled holes as well as the holes for the guiding portions 24 of the two fixation devices may, similarly to the embodiment of FIGS. 1-9, have axes that are non-parallel with respect to each other, so that a relative movement of the fixation devices and the interbody spacer in dorsoventral directions are prevented. The diverging directions of the pre-drilled holes and the tube portions are schematically illustrated in FIG. 20, where "o" denotes the directions of the pre-drilled holes in the upper vertebral body, and "u" the directions of the pre-drilled holes in the lower vertebral body.

Fixation devices with two (or more) anchoring locations in the same vertebral body, like the one illustrated in FIGS. 18 and 19, or even with only one anchoring location, may be used also in conjunction with different embodiments, including but not limited to the ones of any one of FIGS. 10, 12-16, and 22.

Figure 21:
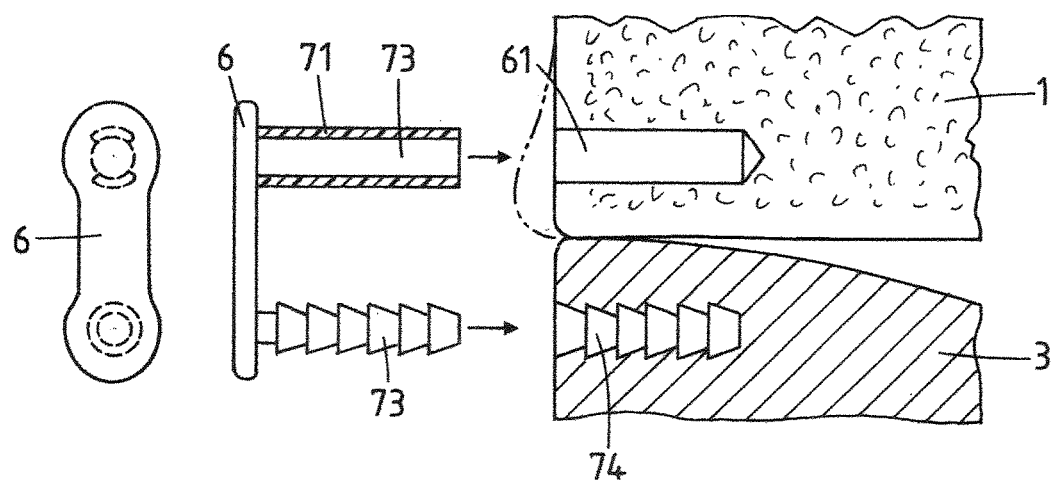

FIG. 21 shows a variant where the fixation device comprises one anchoring location only. More concretely, the fixation device 4 is staple-like and comprises a support portion 6 and two protrusions 73, a first protrusion being coated by a liquefiable material 71, and serving as the anchoring location, and a second protrusion being coupling protrusion suitable of coupling the fixation device to the interbody spacer 3. The anchoring of the anchoring protrusion in the bone tissue is achieved e.g. by the principle or example described in U.S. Pat. Nos. 7,335,205, 6,921,264, US 2006/0 105 295. As an alternative, the anchoring could also be achieved by the principle described referring to FIGS. 16a and 16b, with the tube portions and the support portion being of one piece or being different elements. The coupling protrusion comprises retaining structures (or barb structures) that co-operate with according optional retaining structures of a retaining hole 74 in the interbody spacer. For a reliable fixation, a plurality of staple-like fixation devices 4 as the one in FIG. 21 with at least one anchoring portion anchoring in the upper vertebral body 1 and at least one anchoring portion anchoring in the lower vertebral body. For example, a total of four staple-like fixation devices may be used. The fixation device 4 of FIG. 22 has tube portions with cavities that are rectangular in cross section and that accommodate anchoring material elements 31 that are rectangular in cross section. Further, the fixation device 4 has self-reaming structures 81 that create or widen the openings in the bone tissue while the fixation device is inserted. The rectangular-type cross section supports the action of the self-reaming structures because it brings about an enhanced mechanical strength of the connection between the support portion 6 and the tube portions 23, however, the self-reaming structures may also be present for other cross sections of the tube portions.

Figure 23:
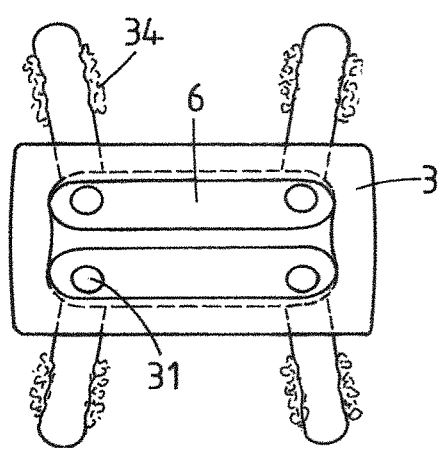
Figure 24:
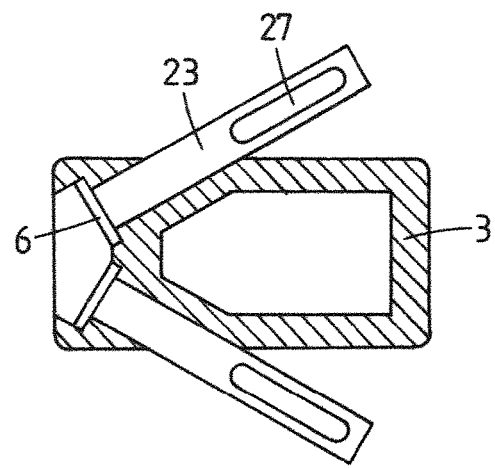

In the embodiment of FIGS. 23 and 24, in contrast to the embodiment of FIGS. 18 and 19 the tube portions are arranged so as to be inserted through the corticular bone of the lower and upper endplate of the upper and lower vertebral body, respectively, instead of through the portion facing to the ventral direction. Such a configuration necessitates the insertion of the fixation devices and the coupling in of mechanical vibrations (or other energy types) from angles that strongly diverge from the horizontal plane and that further strongly diverge between the anchoring of the upper and of the lower fixation device respectively. While both, the damaging of the lower and upper endplates and the diverging angles may be disadvantageous for surgical reasons, there may be situations where nevertheless the embodiments of FIGS. 23 and 24 is the embodiment of choice.

The embodiment of FIGS. 23 and 24 would also be suitable for configurations with only one tube portion (and anchoring material element) per vertebral body, thus only one upper and one lower anchoring location. This is especially the case for adjuvant fixation in addition to other fixation means, such as pedicle screws.

Figure 42:
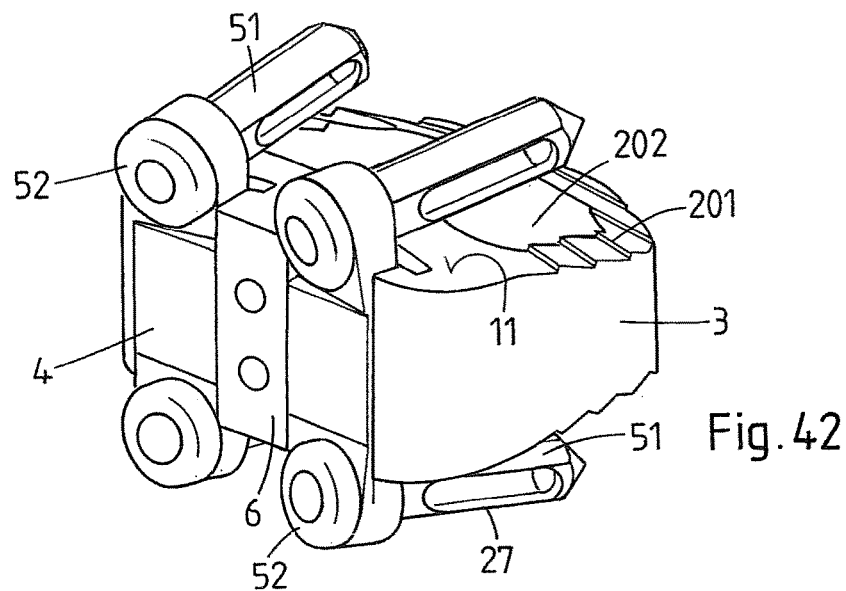
FIGS. 42 and 43 an embodiment of the invention incorporating the first and fifth aspect.
Figure 43:
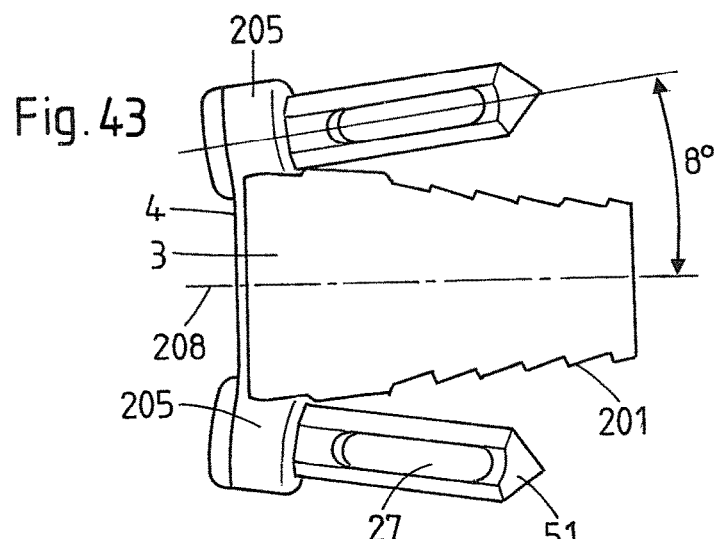

The spine stabilization device depicted in FIGS. 42 and 43 is distinct from the spine stabilization device of FIGS. 1-9 in that:

Instead of one central longitudinal through opening 12, the interbody spacer 3 comprises two lateral through openings 202 separated by a central bridge (not visible in the figure).

The interbody spacer's top surface 11 and the bottom surface comprise retention structures 201 that may comprise a plurality of ridges with, in cross section, a sawtooth-like or barb-like geometry.

The support portions 6 of the fixation devices 4 are not countersunk in the channel-like recesses but have a thickness such as to be flush with the anterior surface of the interbody spacer 3 or even slightly protrude above it.

The fixation devices are based on the principle illustrated with respect to FIGS. 16a and 16b, i.e. they comprise tube elements 51 that are initially separate from the fixation device bodies and that, together with the (not shown) anchoring material elements form fasteners for the fixation device bodies;

The tube portions (being tube elements 51) are not circular in cross section but hexagonal, and that comprise lateral openings 27 arranged as in the embodiments of FIG. 10;

The fastener receiving openings (tube element receiving openings) of the fixation device are such arranged immediately above and below the top surface and the bottom surface, respectively, so that the circumferential collar 52 (or a corresponding screw head if a surgical screw would be used instead of the described anchoring method) reaches to the plane defined by said to top or bottom surface or even further than it; the axis of the fastener, however, at the place of intersection with the anterior end of the interbody spacer, is above or below said plane, respectively.

The fastener openings are such as to guide the fasteners not only at an angle with respect to the sagittal plane, but also at an angle to the median plane 208 of the interbody spacer. In the depicted embodiment both, the upper (first) fasteners and the lower (second) fasteners are at an angle of 8° to the median plane; More in general nonzero angles of up to 20° to the median plane are possible, for example between 4° and 18° to the median plane, or between 6° and 16° to the median plane; preferably the angle of the upper and lower fasteners, projected onto the sagittal plane, with respect to each other is between 8° and 36°, where also an asymmetric arrangement (for example with the angle of the lower fasteners to the median plane being 0° and the angle of the upper fasteners to the median plane being 8° or more) is possible.

The loops 205 in which the receiving openings are arranged are slightly outwardly angled with respect to the support portions, the angle for example corresponding to the angle of the axis to the median plane.

The fixation devices 4 are coupled to the interbody spacer 3 by way of a positive-fit connection, i.e. the channel-like recesses for the fixation devices are undercut; and the diverging guiding protrusions, therefore, are not required for securing the interbody spacer against movements in a dorsal direction (and are not present).

These features that distinguish the embodiment of FIGS. 42-43) from the one of FIGS. 1-9 may be implemented all together (as in FIG. 42) or individually, provided that a substantial nonzero angle of the upper and lower fasteners with respect to each other can only be used if, in contrast to FIGS. 1-9 and like in FIGS. 42-43, no part of the fasteners (namely tube portions) are contiguous in one piece with the support portions.

Figure 44:
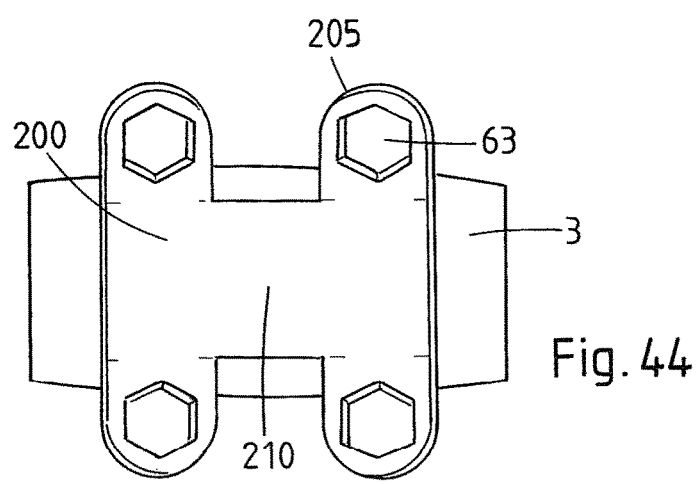
FIG. 44 an other embodiment of the invention incorporating the first and fifth aspect.

The embodiment of FIG. 44 is has the following distinct characteristics:

The receiving openings 63 for the tube elements 51 are not circular and hence not rotationally symmetric; and a portion of the tube elements' outer countour is accordingly adapted.

In contrast to the embodiments of FIGS. 42 and 43, the two fixation device portions are connected by a bridge portion 210, so that the spine stabilization device comprises only one fixation device comprising the support portion 6 and four anchoring portions.

Each of these two characteristics may be implemented separately, i.e., it the fixation device as shown in FIG. 44 may comprise circular receiving openings, or two separate support portions 6 with the non-circular receiving openings may be present.

Figure 45:
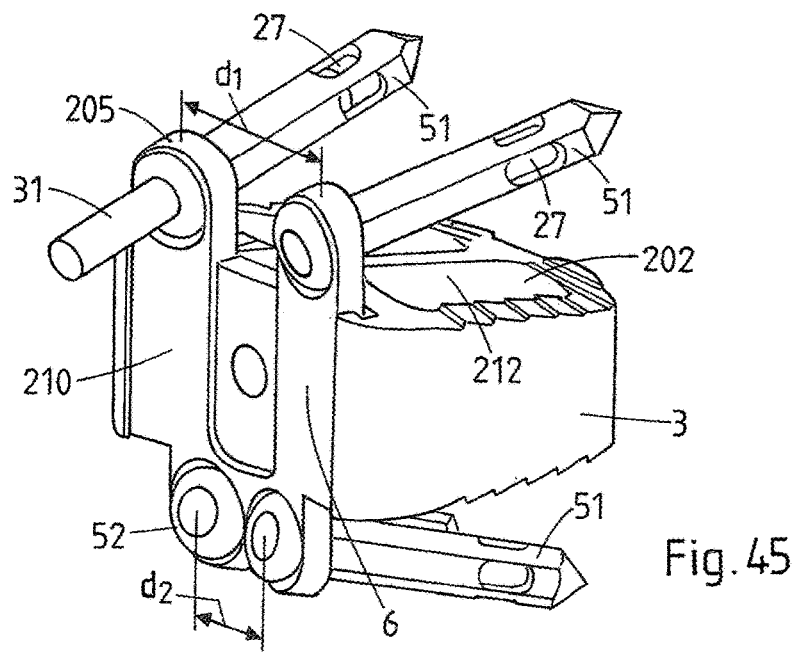
FIG. 45 an embodiment of the invention incorporating the first, fifth and sixth aspect.

The spine stabilization device depicted in FIG. 45 also comprises only one fixation device that has a support portion 6 with fastener receiving openings for four fasteners. The fastener receiving openings are arranged immediately above and below the top and bottom surface, respectively, of the interbody spacer 3. The fastener receiving openings are formed by loops adjacent the upper and lower side of the plate-like support portion 6. The upper fastener receiving openings are at a distance di from each other that differs from the distance di of the lower fastener receiving openings. For this reason, the fasteners of two spine stabilization devices affixed above and below to a certain vertebral body will not interfere with each other, even if the fasteners are comparably long. For this reason, the fasteners may be chosen to be long and the angle projected onto the sagittal plane ("the sagittal angle") between the upper and lower fasteners may be comparably long, so that the fasteners may anchor deep in the vertebral body.

As an other feature of the embodiment depicted in FIG. 45, the tube elements 51 comprise not only two but four transversal openings 27, the openings being comparably smaller. By this measure, the anchoring takes place into four spatial directions. In other configurations, also three, five, six, etc. lateral (transversal) openings would be possible, and in addition or as an alternative a distal axial opening as discussed above.

The fixation device portions with the loop in the embodiment of FIG. 45 are not at an angle to the support portion, but they guide the fastener at an angle due to the fact that the receiving opening axes are at an angle different from 90° to the support portion plane.

In FIG. 45, also the central bridge 212 separating the two through openings 202 is visible.

In addition to the features shown in the figure and explained hereinabove, the spine stabilization device may comprise:
- a positive-fit structure securing the interbody spacer 3 and the fixation device with respect to sliding relative movements in cranial-caudal directions. Such a positive-fit structure may for example comprise an posteriorly protruding peg cooperating with an according indentation of the interbody spacer, or a peg of the interbody spacer cooperating with an opening in the fixation device, etc.
- an—optional—angle stabilizing means for stabilizing/fixing the angle of the fastener with respect to the fixation device body (and thus with respect to the support portion), in addition to the guiding action of the receiving openings. Such means for stabilizing an angle with respect to a plane are known in medical technology; they may comprise an additional element such as a ring, a small plate to put over the fastener head, a pre-tensioning means, etc.

Figure 84:
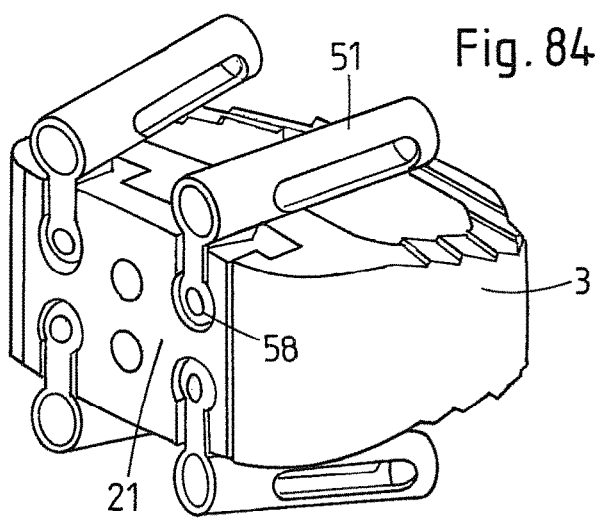
FIGS. 84 and 85 yet an other embodiment of a spine stabilization device.
Figure 85:
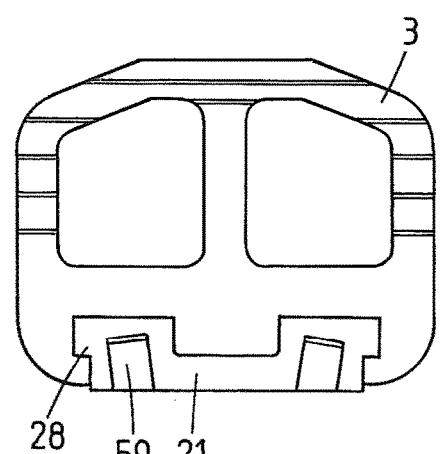

The variant shown in FIGS. 84 and 85 also comprises a plate-like fixation device body 21. It is distinct from the embodiments of FIGS. 44 and 45 in that the tube elements 81 are not guided by receiving openings formed by loops but that the tube 51 elements comprise retaining projections 58 that in the assembled state protrude from the tube element axis towards the median plane and cooperate with retaining indentations 59 of the fixation device body 21 to retain the latter.

As a further feature, that may be implemented independently of the other features of the embodiment of FIGS. 84 and 85 concern an undercut structure of the interbody spacer 3 that cooperates with a corresponding lateral projecting edge 28 of the fixation device body 21 to form a positive-fit connection securing the two parts relative to one another with respect to anterior or posterior movements.

As a further variant, that can be combined with principles of other embodiments, the interbody spacer 3 and the fixation device body 21 of devices like the ones in FIGS. 84 and 85 could be one-piece. In such variants, the device does not comprise any separate fixation device body, and the fixation device just comprises the four fasteners, the retaining projections 58 forming the support portion. Such a variant is comparable in its functionality to the embodiment of FIG. 21 for example.

Figure 67:
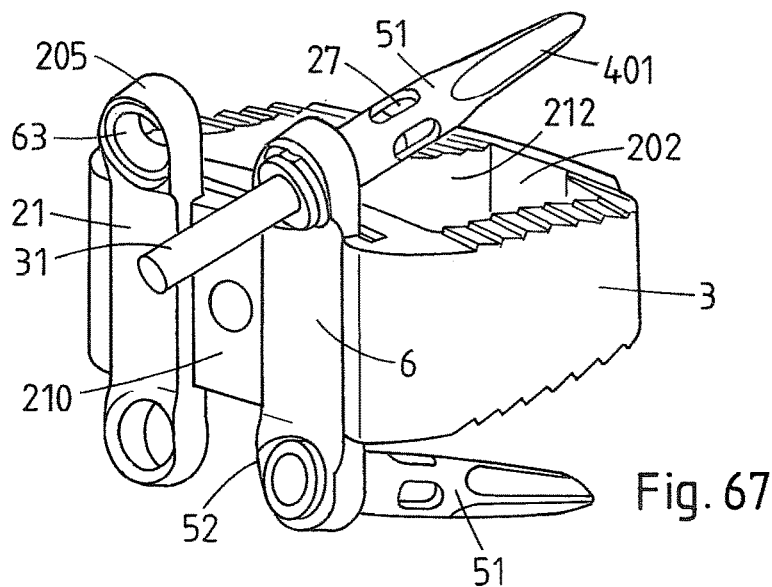
FIGS. 67-69 yet another embodiment of the first and fifth aspect of the invention.

A further embodiment of a spine stabilization device according to the first and fifth aspect of the invention is depicted in FIG. 67. The interbody spacer 3 may be of the kind described referring to FIG. 2, or 42-45. Like in these embodiments, the interbody spacer may be shaped in accordance with the surgeon's needs, and may for example be essentially wedge-shaped tapering towards the posterior side. Different sizes of interbody spacers may be available. In addition or as an alternative to providing different sizes of interbody spacers, one may also provide distance defining means that keep the interbody spacer at a defined distance from the support portion, such distance defining means may comprise a separate connection element or a protrusion of the fixation device body 21 and/or the interbody spacer 3, etc.

The fixation device comprises a single fixation device body 21 with a bridge portion 210. The receiving openings for the tube elements are formed by loops 205 that are arranged, like in FIG. 44, in an essentially symmetrical manner with respect to the median plane, i.e. the upper and lower tube elements are at about equal distances from each other. Therefore, after anchoring, the anchoring portions may be distributed to be spaced from each other as far sensibly possible, and this distribution provides good stability during torsional and sidewards bending movements of the spinal column.

In contrast to the embodiment of FIG. 44, the shape of the receiving openings in the depicted version is not such as to prevent rotational movement of the tube elements 51, but such a shape is not excluded for alternative embodiments. The support portion comprises a central hole 205.

Figure 68:
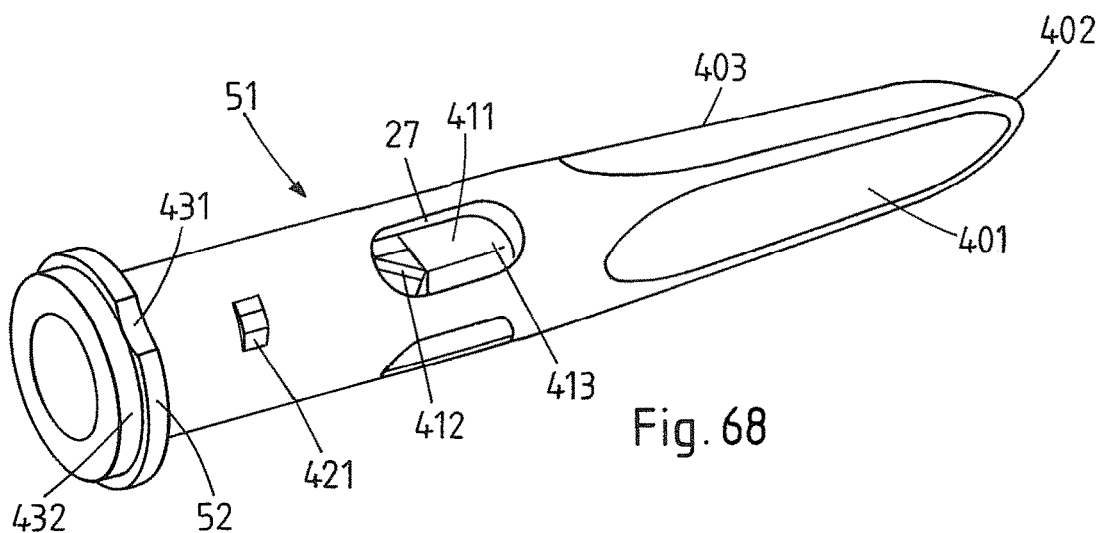
Figure 69:
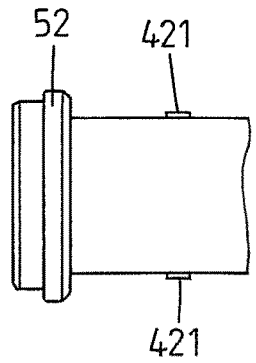

The tube elements are distinct from the tube elements of the previously described embodiments in that they have a plurality of features mentioned in the following. These features can be realized in combination (as illustrated in FIGS. 67-69), as well as individually or in any sub-combination. For example, the self-reaming structure may be combined with the directing structure and/or the gripping slot, but without the locking ramp and/or the centering step, etc; all sub-combinations are possible.

Self-reaming structure: The tube elements 51—as can also be seen in more detail in FIG. 68—comprise in a distal region thereof a self-reaming structure 401 with a pronounced tip 402 and a plurality of cutting blades 403 radially protruding from a central portion. The cutting blades may be azimuthally aligned with the openings 27, through which the liquefied material of the anchoring material elements 31 exits, and which are arranged more proximally. In the depicted embodiment, four cutting blades arranged in a cross-like manner and a corresponding number of openings 27 are depicted.

In alternatives to the embodiment depicted in FIG. 68, the lateral openings 27 could be at azimuthal positions corresponding to the azimuthal positions of the grooves between the blades, and/or the openings 27 could be so as to drive the anchoring material pushed out of the openings into a radial-distal direction and partially into the grooves between the blades. Configurations of lateral openings that are at an angle to the radial direction are schematically sketched further below.

More proximal arrangement of the openings 27 for the anchoring material: In contrast to the previously disclosed embodiments, the openings 27 for the liquefied anchoring material are not arranged towards the distal end of the tube elements, but in a central region. This may have one or both of the following advantages:

- the arrangement of tipped, slim self-reaming structure(s) becomes possible, which self-reaming structures help to avoid a surgical step of making a bore in the vertebral body, for example by means of an awl;
- the anchoring locations where the anchoring material interpenetrates structures of the bone tissue in vicinity of the circumferential surface of the vertebral body is more dense and stronger than in the middle thereof. By the measure of providing the openings 27 subcortically, i.e. close to the place where the cortical bone is penetrated by the tube elements, therefore, the anchoring strength can be increased.

Locking ramps: As also illustrated in FIG. 69, the tube element may comprise at least one ramp-like feature—two ramp-like features 421 in the illustrated embodiment—that lock the tube element behind the fixation device body 21. This may be useful prior for a provisional fixation prior to the anchoring process. In embodiments, where a guiding fit is tight fitting, for example even a transition fit or an interference fit, this locking feature may provide redundancy in addition to the locking by frictional forces.

Gripping slot: The circumferential collar 52 that secures the fixation device body comprises a feature deviant from a rotationally symmetric shape, such as a slot 431. Such a feature may be used to hold the tube element 51 when, for a removal process, a removal tool is screwed into the proximal opening, whereby a torsional momentum acts on the tube element 52.

Centering step: The tube element comprises a step-like proximal feature that may co-operate with an according tool during insertion of the anchoring material element to center the tool.

Directing structure: The tube element also comprises a directing structure that is arranged towards the distal and of the longitudinal bore through which the anchoring material element is inserted. The directing structure is structured angularly with respect to a longitudinal axis of the longitudinal opening. It is capable of directing different portions of the liquefiable material to different ones of the openings 27.

'Structured angularly'—or azimuthally—means that the structure is not constant along the circumference but varies as a function of the azimuthal angle. In this, the directing structure is a structure within the cross section of the longitudinal bore, i.e. if, for example, the longitudinal bore has a circular cross section, the directing struture's radial position is at least partly within the radius of the bore.

In a tube element, the liquefaction, when mechanical oscillations impinge on the anchoring material element, takes place by the impinging mechanical energy being absorbed in a vicinity of the distal end of the liquefiable element and in a vicinity of the holes. For example, material of the liquefiable element may be liquefied at an interface between the liquefiable element and the directing structure.

The directing structure is then formed by a stop face, against which the distal end of the liquefiable element is pressed during liquefaction. The distal stop face for the liquefiable element may for example close off the longitudinal opening towards the distal side, as illustrated in FIG. 68. As an alternative, it would also be possible that the distal stop face formed by the directing structure does not completely close off the longitudinal opening but only substantially reduces (by for example at least 50%) a distal portion of the longitudinal opening's the cross section compared to the proximal portion. An optional, remaining cross section of the longitudinal opening distal portion extending distally from the directing structure could then for example serve as a central guiding portion or as distal hole through which liquefied material portions may be pressed out in addition to the openings 27 in wall of the tube element.

The directing structure angularly structures the volume proximally of the distal end of the liquefiable element so that different portions of the liquefied material are directed to a determined one of the openings 27.

It has been found that by this approach, a potential problem encountered with prior art medical devices is solved. If the tissue adjacent to different holes was significantly different in terms of porosity and/or hardness, it could happen that a large part of the liquefied material exited through the one hole where the least resistance for the hydrostatic pressure on the liquefied material is encountered. This could result in an anchoring that is undesiredly anisotropic. Due to the directing structure approach, there is a more homogeneous distribution of liquefiable material between the openings.

In embodiments of tube elements having a directing structure, the directing structure comprises at least one wall 411 protruding proximally from the directing structure body. The wall separates sub-volumes of a distal region of the longitudinal opening where the liquefaction takes place. In this, the wall does not need to have a homogeneous thickness but merely makes an angular separation between different volume sections of the longitudinal opening that each communicate with the different holes, so that portions of the liquefiable material in these volume portions will have a strong tendency or even be forced to exit the longitudinal portions through the particular attributed hole.

In the depicted embodiment, the tube element comprises four walls 411, each in an axial, radial plane so that a cross-like cross section is obtained.

In addition to making this angular separation, the wall also serves as energy director where vibration energy tends to be absorbed and where there liquefaction sets in. Due to this, the liquefaction may set in proximally of the holes or at least proximal of their distal end, so that a blocking of the holes by remaining solid parts may be reduced or prevented. Especially, the proximal edges 412 formed by the walls may serve as energy directors.

In the depicted embodiment, the directing structure (optionally) further comprises a ramp portion 413 that slopes away from the longitudinal axis towards a distal end of the according hole, so that there is no pronounced edge between the wall and the stop face. The ramp portion may be curved. It may comprise a radius geometry that guides the liquefiable material from an axial to a radial direction within the sheath element.

While in the depicted embodiment, the walls protrude less into the proximal direction than the openings' most proximal extension, the wall could also protrude further to the proximal direction than holes' most proximal extension, so that every material that reaches the hole is confined to the volume segment by the wall and is thus prevented from getting to an other wall by the hydrostatic pressure acting on the liquefiable material and by its movement. These embodiments are especially suited for cases where a large difference between the resistances encountered for material flowing out of the different holes is to be expected. In other embodiments, like in FIG. 68, the wall protrudes less far the to proximal side than the holes most proximal portion, but nevertheless the directing effect is there. Preferably, the wall protrudes to at least $\frac{1}{3}$ or to at least $\frac{1}{2}$ of the proximal extension of the hole or of at least one hole that is adjacent (measured from the most distal side of the holes).

The directing structure at a distal end of the (elongate) cavity may also be present in embodiments without any separate tube elements where the elongate cavity is formed by the fixation device body (such as embodiments like the ones of FIG. 4-6, FIG. 13, FIG. 22, FIG. 28, etc.).

As a variant of the embodiment of FIG. 67, the tube elements may lack the portions distal of the openings 27 (that are still arranged relatively closely to the stabilization device body so that sub-cortical anchoring is obtained). Thus, in this variant, the self-reaming structures would be omitted. Such a shortened tube element is interesting from the point of view of imaging processes such as MM (magnetic resonance imaging) processes where it is desirable to have as large regions as possible that are free of any metal. The variant features the special advantage that no metallic parts are close to the spinal canal. The advantages of sub-cortical anchoring are preserved. In embodiments of this variant, there are more degrees of freedom concerning the angle to the median plane and/or the angle to the sagittal plane. Especially, either angle or both angles may be smaller than for other embodiments, so that the surgeon can access in a more straight manner.

In further embodiments of this variant, especially with the said angles being approximately 0°, the tube elements are not separate, but they may be one-piece with the fixation device body. In other words, in these embodiments the elongate cavities are a cavities defined by the fixation device body. In such embodiments, there is no need for a separate insertion of the tube elements.

Figure 81:
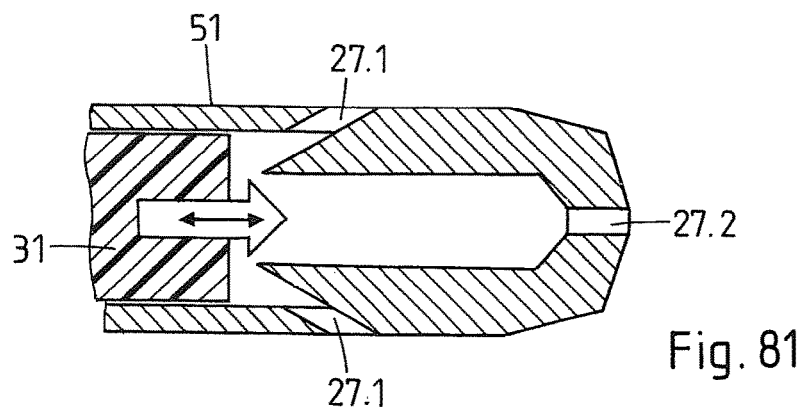

Further optional features of tube elements 51 of the kind described referring to FIG. 68 or also referred to in other hereinbefore described embodiments are depicted in FIG. 81. FIG. 81 schematically shows a section of a distal portion of a tube element 51 with a partially inserted anchoring material element 31. A first optional feature concerns the direction of the channel formed by the lateral tube element openings 27.1. The lateral openings are not radial but at an angle to the radial direction. In the depicted configuration, the lateral openings 27.1 are at an angle to the distal side, i.e. the outflow of anchoring material is in a radial-distal direction. Such a configuration may provide additional stability against shear forces.

A second optional feature, that may but need not be combined with the first optional feature is a central distal opening 27.2 or cannulation of the tube element. Such a central distal opening is substantially smaller in cross section than the proximal opening into which the anchoring material element 31 is introduced. The central distal opening may be combined with self-reaming structures of the tube element also, in which case the self-reaming structure may comprise a blade, but the distal section of the tube element is not as a whole blade shaped but comprises a tube-like central channel. The central opening may be used for guiding purposes in minimally invasive surgery (for example guidance by a K wire) and/or is used to distally press out liquefied anchoring material.

A central distal opening (but for example combined with longer lateral openings 27.1 than depicted in FIG. 81, and possibly with the lateral openings not necessarily being at an angle to the radial direction) may be advantageous in variants that comprise sub-cortical anchoring but without a tube element portion substantially distal of the lateral openings—so that the anchoring material flown out in the distal direction provides additional stability against tilting forces.

Figure 82:
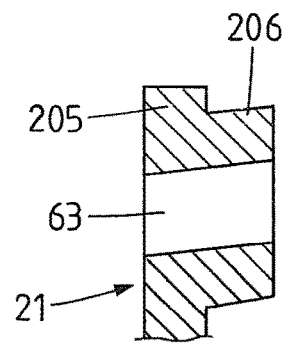
FIGS. 81 and 82 variants of features for the embodiments of FIGS. 44, 45, 67-69.

A further optional feature of the fixation device body 21 is shown in FIG. 82. The receiving openings 63 comprise a collar portion 206 that protrudes distally from the plate-like support portion and ensures that the guiding portion is longer than the thickness of the plate. Thereby, an improved guidance and anchoring of the tube element in the fixation device body is ensured. The collar portion 206 (or sheath portion) may be driven into the cancellous bone after local removal of the cortical bone tissue, for example by hammering.

As mentioned previously, in all embodiments that comprise receiving openings, the guiding portion formed by the inner surface of the receiving openings and a section of the outer surface of the tube element may cooperate to form an angle defining fit, such as a clearance fit, a line-to-line-fit, a transition fit or a press fit (interference fit). This also holds for embodiments where the fastener does not comprise a tube element but an other shaft portion, for example of a core of a non-liquefiable material. Configurations with a tube element are especially suited for angle guiding fits, because the tube element firstly does not have to be rotated for introduction, and secondly the energy used for the liquefaction (for example the mechanical vibration) does not act on the tube element directly but on the anchoring material element. Thus, the energy will not be easily transmitted to the fixation device body in an undesired manner.

A further category of embodiments of spine stabilization devices is described referring to FIGS. 26-29. While the embodiments concern a spine stabilization device with a dimensionally stiff interbody spacer, the embodiment is also advantageous for completely different applications, especially applications where it is not desired to have device components outside of the gap to be bridged by the surgical device. One category of such applications is arthrodetic implants.

Figure 26:
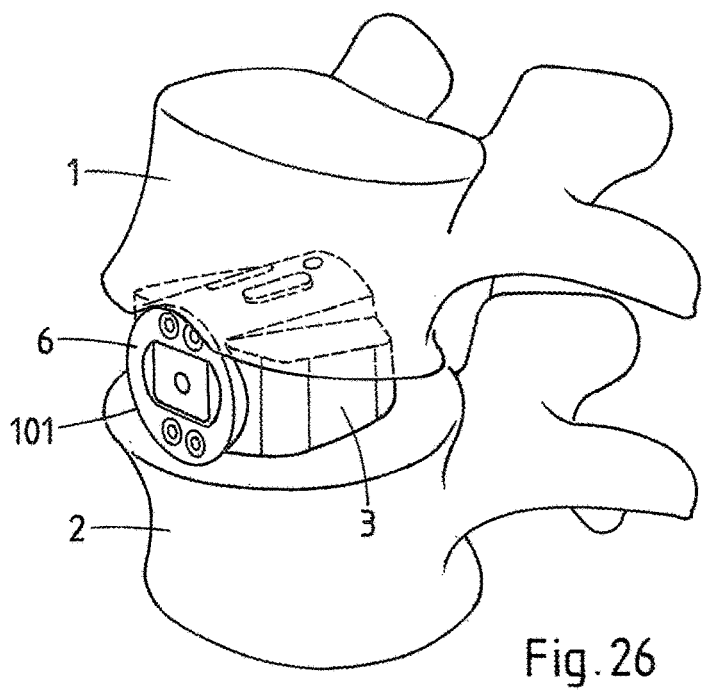

FIG. 26 depicts an embodiment of a spine stabilization device according to this category inserted in a human spine. The figure shows an upper vertebra 1 and a lower vertebra 2, between which the intervertebral disc has been at least partly removed. The device comprises an interbody spacer 3, serving as a distance holder, between the vertebral body of the upper vertebra and the lower vertebra. The interbody spacer after the surgical insertion between the vertebral bodies is held in place by a fixation device 101. The fixation device 101 comprises a plurality of anchors anchoring it in the upper and the lower vertebral body. Further, it comprises a support portion 6 securing the interbody spacer 3 against movement towards the ventral direction.

Figure 27:
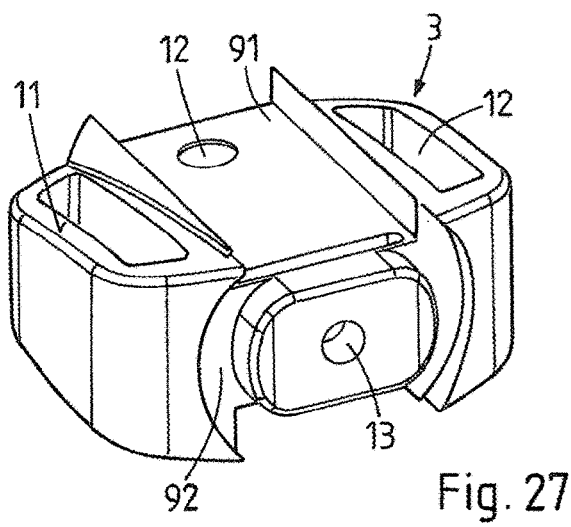

FIG. 27 shows the interbody spacer 3 in somewhat more detail. The interbody spacer may again be made of any suitable material including PEEK, potentially coated by Hydroxylapatite (HA). It may alternatively be made of a different biocompatible material suitable for an intervertebral, such as an other plastics, a ceramics, or Titanium, also potentially coated.

The interbody spacer 3 comprises a top surface 11 and an opposite bottom surface for being in contact with the lower endplate of the upper vertebral body and the upper endplate of the lower vertebral body, respectively. The interbody spacer further comprises a longitudinal (relating to the spine axis) through opening 12 permitting bone growth between the upper and lower vertebral bodies and optionally being filled, when inserted surgically, by bone graft and/or bone growth promoting material. In the depicted configuration, the interbody spacer comprises one through opening that both is centrally and symmetrically located with respect to the sagittal plane, and aligned with a corresponding opening in the fixation device, however, other arrangements of longitudinal through openings are possible. For example, it would also be possible to have one or two or more than two peripheral openings, no opening, or one or more central openings (see below).

Further, the interbody spacer 3 may be shaped according to the surgeon's needs and comprise retention structures and/or bone ingrowth macroscopic and/or microscopic structures (such as the holes 13 perpendicular to the longitudinal axis depicted in the figure), channels etc. (not shown). In addition, the interbody spacer 3 may be shaped to accommodate corresponding structures of the fixation device(s), such as channel-like recesses 91, 92 that accommodate portions of the fixation device.

Figure 28:
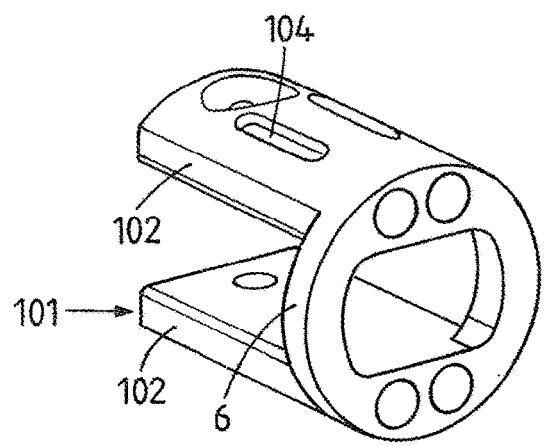

The fixation device body 101 shown in FIG. 28 comprises the support portion—here constituted by two arch shaped bridges connecting an upper and a lower anchoring portion 102. The anchoring portions 102 each are shaped to project in a dorsal direction into a space between the interbody spacer and the respective vertebral body. Each anchoring portion comprises at least one—two in the depicted embodiment—cavity that is open to the ventral side for insertion of an anchoring material element 31. Further, the cavities comprise at least one opening 104 that allows a radial (with respect to the axis of the elongate cavity) outflow of the anchoring material in a liquid state. During the anchoring process the anchoring material in its liquid state flows out through the opening and into structures of the bone tissue surrounding the respective anchoring portion 102. After re-solidification it forms together with the anchoring portions 102 of the fixation device body an anchor for the fixation device.

For applications in fixation of an implant that, in contrast to the illustrated interbody spacer device, does not rigidly connect the upper and lower bone tissue portions—such as an intervertebral disc prosthesis, instead of the anterior ring that constitutes the support portion, the upper and lower anchoring portions 101, 102 would be integrated in the respective upper and lower plate elements (retaining elements) of the implant.

Figure 29:
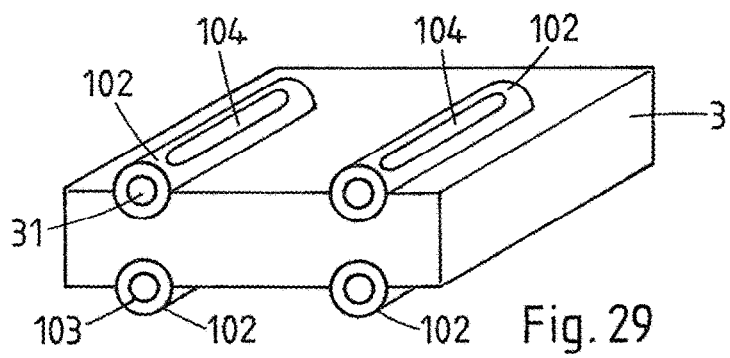

Further, the fixation device may comprise means (not shown) coupling the fixation device to the interbody spacer and thereby securing the interbody spacer against movements in the dorsal direction. Such coupling means may be constituted by a screw or a latching connector, a barb engaging in a recess, etc. FIG. 29 depicts a variant of the embodiment of FIGS. 27 and 28 where the fixation device comprises, instead of one upper and one lower, centrally located, anchoring portions two upper and two lower peripheral anchoring portions. The anchoring portions or at least two pairs of anchoring portions may be connected by (not shown) bridge elements, as the previously described embodiment. The variant of FIG. 29 is advantageous in cases in which a central longitudinal opening (not shown) for bone growth therethrough is desired, instead of the peripheral longitudinal openings 12 shown in FIG. 27.

Figure 30:
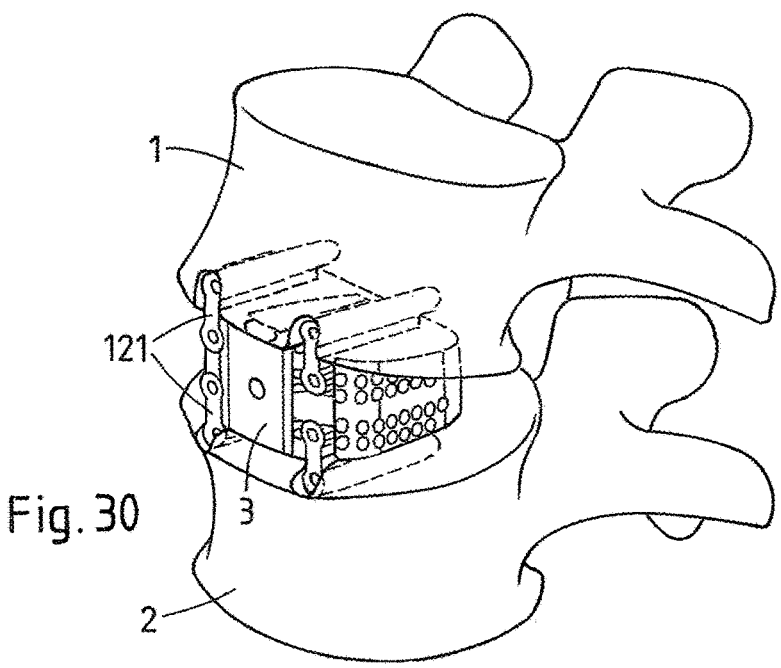
FIGS. 30-32 an embodiment of the third aspect of the invention.
Figure 31:
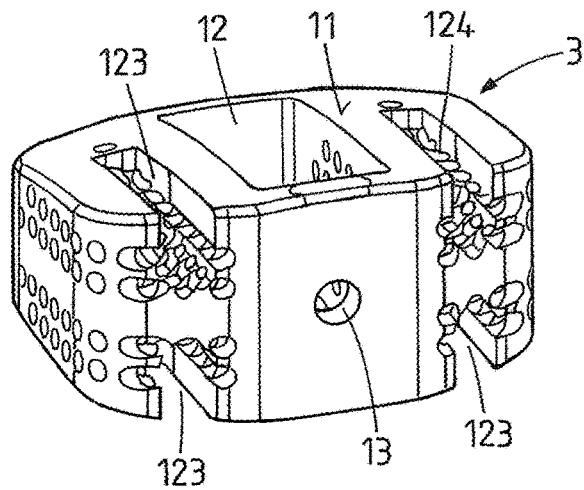
Figure 32:
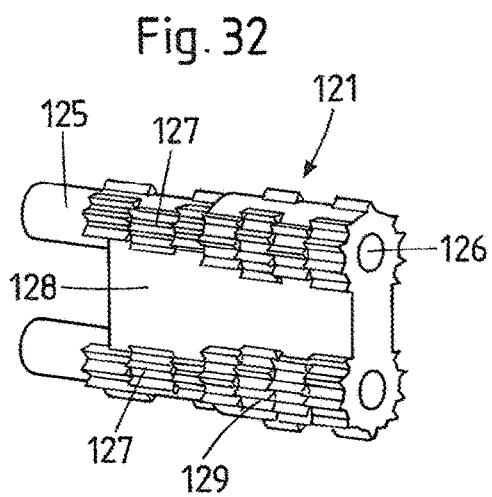

FIGS. 30-32 show yet another category of spine stabilization devices. In contrast to the previously described categories and embodiments, the spine stabilization device according to FIGS. 30-32 does not rely on a support portion to be anchored by (separate) elements comprising the anchoring material that during the anchoring process is in a liquid state. Rather, the embodiments of FIGS. 30-32 include anchoring devices e.g. of the kind described in WO 2008/034 276. In addition to the embodiments described in WO 2008/034 276, the anchoring devices of this aspect of the invention, however, comprises a first and a second securing portion each approximately pin-shaped in the depicted embodiment, and the two securing portions connected by a bridge portion that protrudes, on the distal side, less far than the securing portions.

Also the teaching that holds for devices of the kind illustrated in FIGS. 30-32 may be used for example for fixing respective upper and lower plate elements (retaining elements) of an intervertebral disc prosthesis.

FIG. 30 depicts an embodiment of a spine stabilization device according this aspect inserted in a human spine. FIG. 30 shows an upper vertebra 1 and a lower vertebra 2, between which the intervertebral disc has been at least partly removed. The device of the embodiment described here also comprises an interbody spacer 3, serving as a distance holder, between the vertebral body of the upper vertebra and the lower vertebra. The interbody spacer after the surgical insertion between the vertebral bodies is held in place by a plurality of anchoring devices 121.

FIG. 31 shows the interbody spacer 3. The interbody spacer 3 may again be made of any suitable material including PEEK, potentially coated by Hydroxylapatite (HA). It may alternatively be made of a different biocompatible material suitable for an intervertebral, such as an other plastics, a ceramics, or Titanium, also potentially coated.

The interbody spacer 3 comprises a top surface 11 and an opposite bottom surface for being in contact with the lower endplate of the upper vertebral body and the upper endplate of the lower vertebral body, respectively. The interbody spacer further comprises a longitudinal (relating to the spine axis) through opening 12 permitting bone growth between the upper and lower vertebral bodies and optionally being filled, when inserted surgically, by bone graft and/or bone growth promoting material.

In the depicted configuration, the interbody spacer comprises one through opening that is centrally located with respect to the sagittal plane. However, other numbers and arrangements of openings are possible. For example, it would also be possible to have two or more, possibly smaller, central through openings, or one opening or a plurality of openings more on a lateral position, or no opening at all etc.

Further, the interbody spacer 3 may be shaped according to the surgeon's needs and comprise retention structures and/or bone ingrowth macroscopic and/or microscopic structures such as the holes 13 perpendicular to the longitudinal axis depicted in the figure, channels etc.

The interbody spacer comprises four channel-like recesses 123 that are open both, to the ventral side, as well as to the upper or lower side. At least in vicinity to the recesses, the interbody spacer further comprises an open porous structure, with preferably macroscopic pores, that may be interpenetrated by anchoring material in a liquid state. This results in a macro form fit connection. Instead of an open porous structure, also a structure with a single cavity (or very few cavities) with an undercut may be present, so that the resulting macro form fit connection is a rivet-kind connection.

The anchoring device as depicted in FIG. 32 consists of a thermoplastic material liquefiable e.g. by the joint action of mechanical oscillation and a pressing force, such as a polylactic acid (PLA). It comprises an upper and a lower securing portion 127 as well as a bridge portion 128 between the anchoring portions. The securing portions 127 are pin-shaped with energy directors 129. Each securing portion has a tip piece 125 protruding, on the distal side, preferably further than the bridge portion.

In the anchoring process, one of the securing portions 127 is inserted into a recess 123 of the interbody spacer 3, while the other securing portion is inserted into a pre-drilled recess in the vertebral body adjacent to the recess 123. To that end, both, the recess 123 in the interbody spacer 3 and the recess in the bone tissue are configured to have a diameter that is smaller than an outer diameter of the respective securing portion 127. When being inserted into the space comprising the recesses 123 in the interbody spacer and in the vertebral body, the thermoplastic material of the securing portions due to the effect of e.g. the mechanical vibrations coupled into the anchoring device starts being liquefied and interpenetrates the open porous structure of the interbody spacer and the tissue of the vertebral body, respectively. The bridge portion after the anchoring process couples, due to the arising positive-fit connections of the securing portions with the open porous structure and with the bone tissue, the interbody spacer and the vertebral body to each other. If the anchoring devices 121 are chosen to be of a resorbable material, after resorption there will be ingrowth of bone tissue into the recess 123 in the interbody spacer and into the open porous structure 124.

As previously mentioned for other embodiments of the spinal stabilization device according to the invention it is possible for the embodiment as illustrated in FIGS. 30 to 32 also to achieve liquefaction of the anchoring material comprised by the securing portions 127 by coupling electromagnetic radiation preferably of the visible or infrared frequency range into the securing portions 127 and to absorb the radiation in the vicinity of surfaces of the securing portions which are in contact with the bone tissue of the vertebral body or with the interbody spacer to there produce the thermal energy needed for the desired liquefaction.

Figure 37:
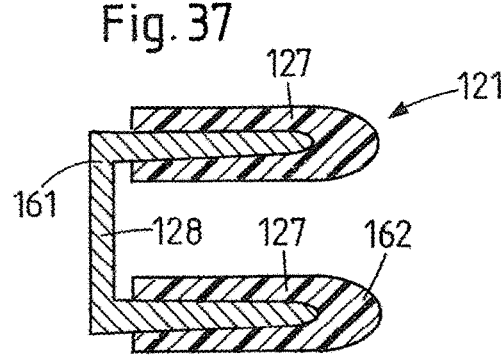
FIG. 37 an alternative embodiment of an anchoring device for a device according to the third aspect of the invention.

FIG. 37 shows an embodiment of an anchoring device that is of a hybrid kind, i.e. that comprises, in addition to the portions of liquefiable material, also portions of non-liquefiable material. More concretely, the anchoring device 121 comprises a metallic core 161 constituting the bridge portion 128 and a core of the two securing portions 127, and, for each securing portion, an outer part 162 consisting of liquefiable material.

Figure 33A:
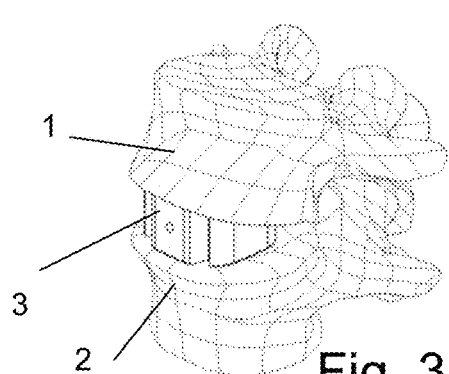
FIGS. 33*a*-33*l* a method of preparing a spine for anchoring a spine stabilization device according to the embodiment depicted in FIGS. 1-9.
Figure 33B:
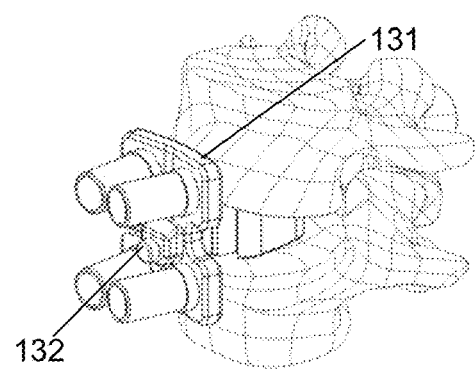
Figure 33C:
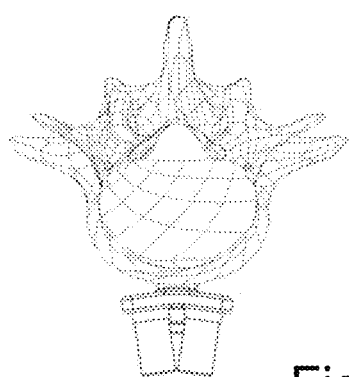
Figure 33D:
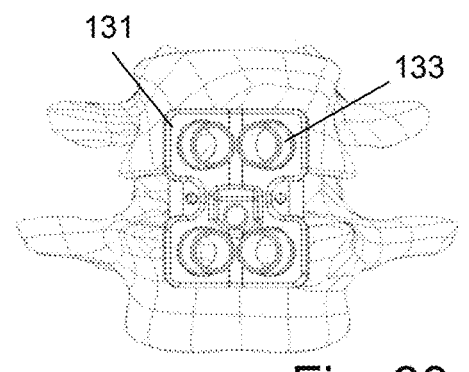

FIGS. 33a-33l illustrate method steps of a method of preparing anchoring of a spine stabilization device of the kind described referring to FIGS. 1-22, using an insertion kit. After the intervertebral disc (or remains thereof) has partly been removed, if necessary, the interbody spacer 3 is inserted in the space between the vertebral bodies (FIG. 33a). Then, a drill guide 131 is placed in a defined positional relationship with the intervertebral body. In the depicted embodiment, the drill guide is temporarily secured to the interbody spacer by means of a fastening screw 132 or the like (FIGS. 33b-33d). The drill guide comprises four drill guiding portions, the axes of which are essentially parallel to the median plane of the interbody spacer, but with the axes of the guiding portions on the left, and their projections onto the transversal plane, being at a small angle to the axes of the guiding portions on the right, as can be seen in FIGS. 33b-33d. Instead of a drill guide with four drill guiding portions, a drill guide with two drill guiding portions could be used, the drill guide being turned around after drilling the first two holes. This variant would feature the advantage that the drill guide is less bulky.

Figure 33E:
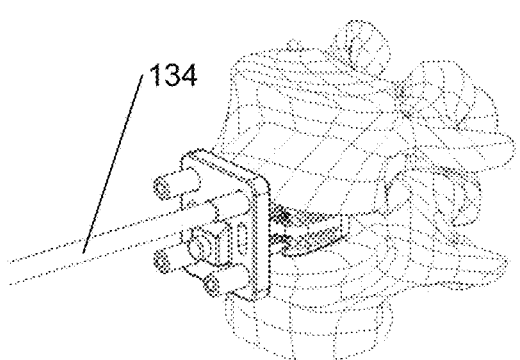
Figure 33F:
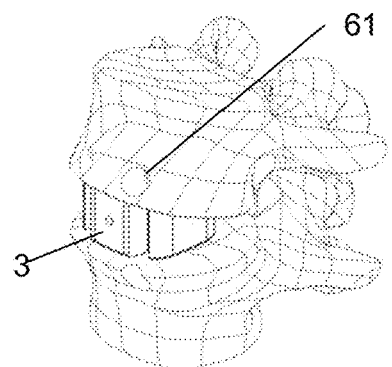
Figure 33G:
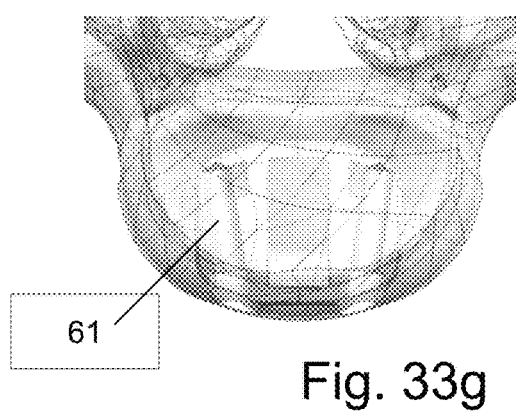
Figure 33H:
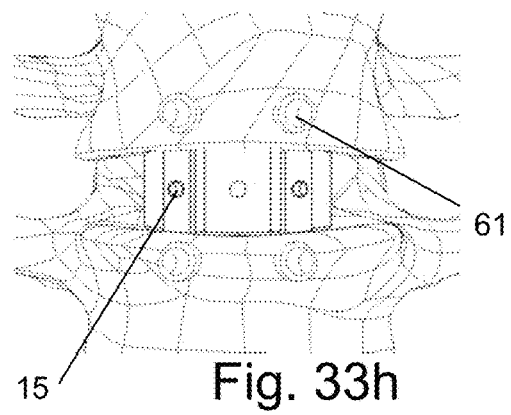
Figure 33I:
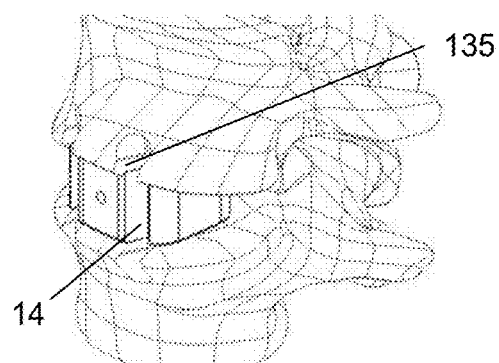
Figure 33J:
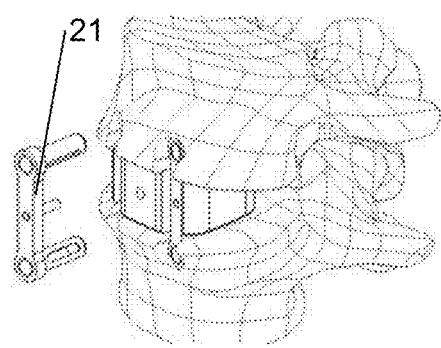
Figure 33K:
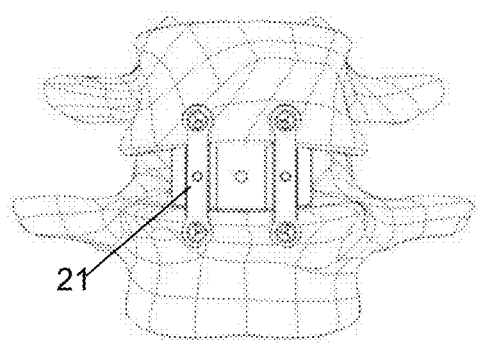
Figure 33L:
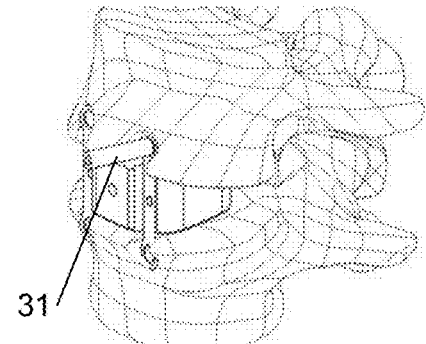

Thereafter, the pre-drilled holes 61 (or positioning holes) in the bone tissue are made. FIG. 33e illustrates a drill bit 134 of an according drill, the drill bit 134 being guided by the drill guiding portions. FIGS. 33f-33h illustrate the result after removal of the drill and of the drill guide. Parts of the vertebral body endplate underneath the pre-drilled holes 61 are thereafter removed down to the anterior surface of the interbody spacer 3 at least to a depth in the dorsal direction corresponding to the thickness of the support portion of the fixation devices to extend in the recess 14 in the interbody spacer for the support portion into the vertebral body to yield a countersink 135 (FIG. 33i). This is for example accomplished by a cutting caliper. Then, the two fixation device bodies 21 are inserted, with their support portions fitting into the channel-like recesses 14 of the interbody spacer 3 (FIG. 33j, 33k). Finally, the anchoring material elements 31 are inserted, and the anchoring process, as for example described in U.S. Ser. No. 12/260,698 incorporated herein by reference in its entirety, is carried out. This procedure is repeated for all four of the anchoring material elements. Insertion of the anchoring material elements 31 may optionally be done in a state in which they are mounted on an anchoring instrument's guiding portion, as explained in more detail further below.

As a variant of the hereinabove described method, it would also be possible to use a drill guide before insertion of the interbody spacer. To this end, the drill guide may comprise a support portion for being inserted between the vertebral bodies and for at least roughly defining the relative position of the vertebral bodies. Such a support portion may for example have a shape essentially corresponding to the shape of the later introduced interbody spacer (with the potential absence of through holes and positioning structures etc.), but be rigidly connected to the guiding portions of the drill guide. After removal of the drill guide, the interbody spacer may be inserted, with the pre-drilled holes together with the fixation devices defining its exact position.

Figure 34A:
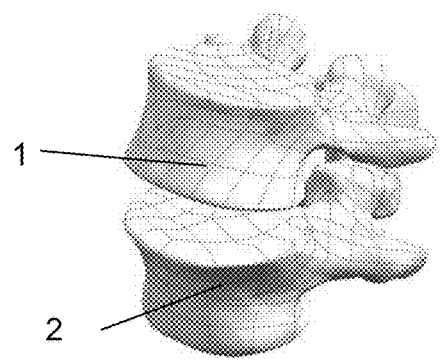
FIGS. 34*a*-34*l* a method of preparing a spine for anchoring a spine stabilization device according to the embodiments depicted in FIGS. 26-29.
Figure 34B:
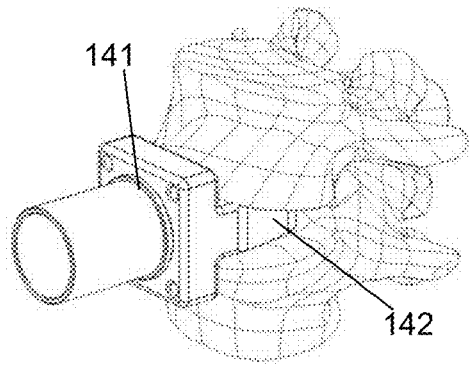
Figure 34C:
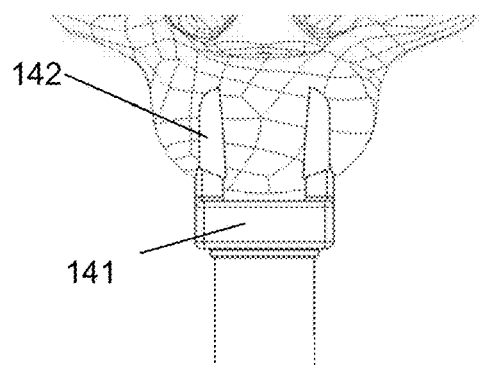
Figure 34D:
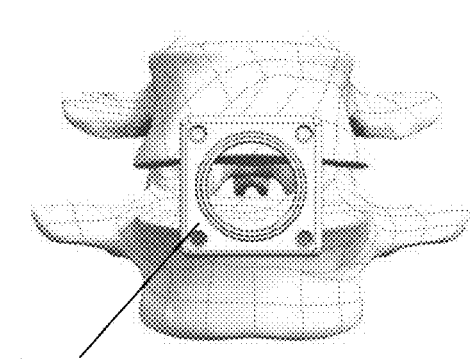
Figure 34E:
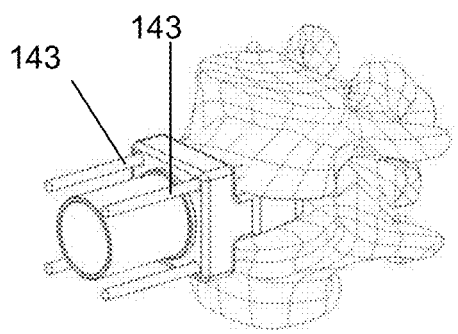
Figure 34F:
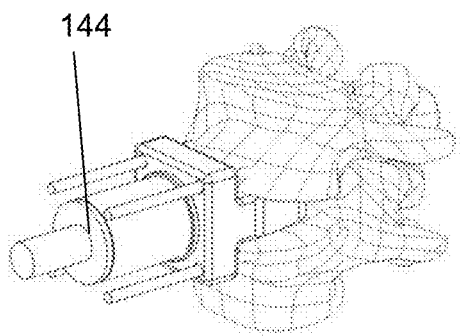
Figure 34G:
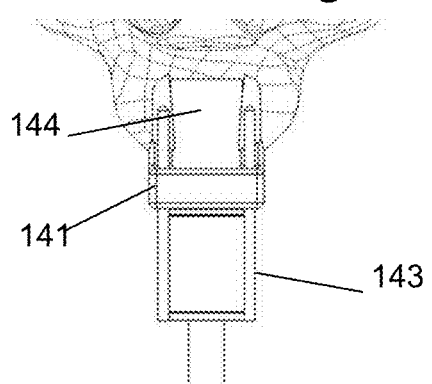
Figure 34H:
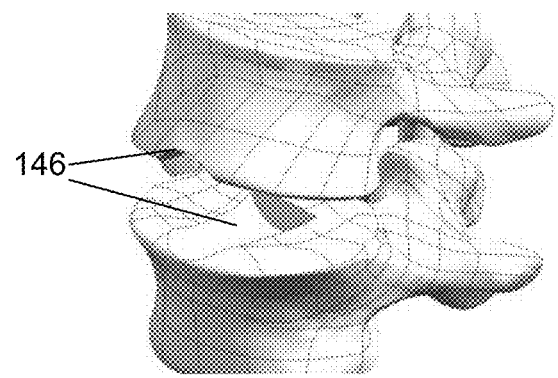
Figure 34I:
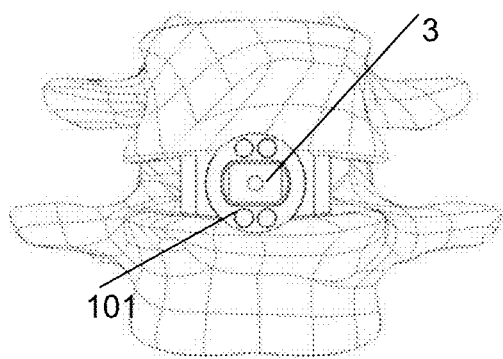
Figure 34J:
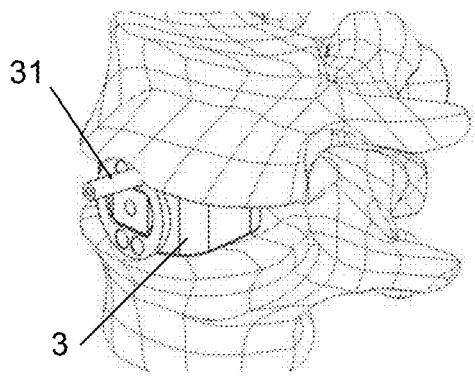
Figure 34K:
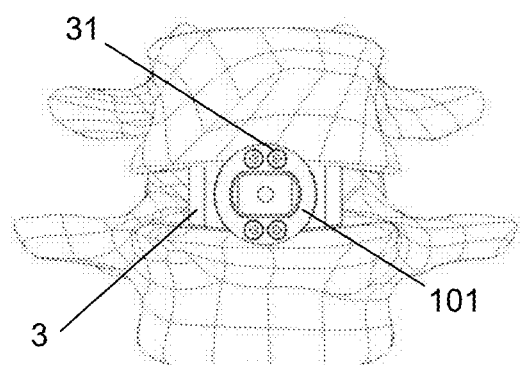
Figure 34L:
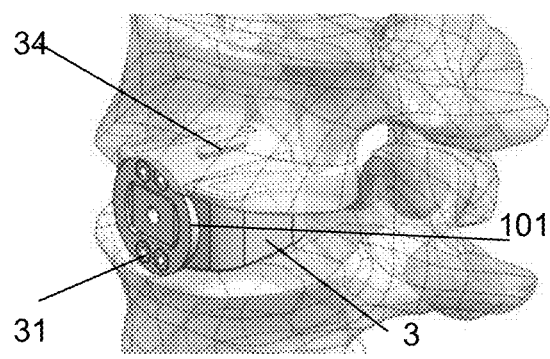

FIGS. 34a-34l illustrate yet the according process for a spine stabilization device as described referring to FIGS. 26-29, by means of an according insertion kit. A reaming guide 141 with a support portion 142—having the shape of two distally protruding wings in the depicted embodiment—is placed with the support portion 142 protruding into the reamed space between the vertebral bodies of the upper and lower vertebrae 1, 2 (FIGS. 34a-34d). Then, at least one auxiliary device, such as four Kirschner wire drill bits 143 as illustrated in FIG. 34e, are used to fix the reaming guide during the reaming operation. Next, grooves 146 in both, the upper and the lower vertebral body, are created with a reamer in one go (FIGS. 34f-34h). The radius of the grooves corresponds at least approximately to the radius of the fixation device's anchoring portions 102. After removal of the drill guide, the interbody spacer 3 and the fixation device 101 are placed (FIG. 34i), and the anchoring material elements are inserted in the respective cavities and anchored (FIGS. 34j-34l).

Figure 35A:
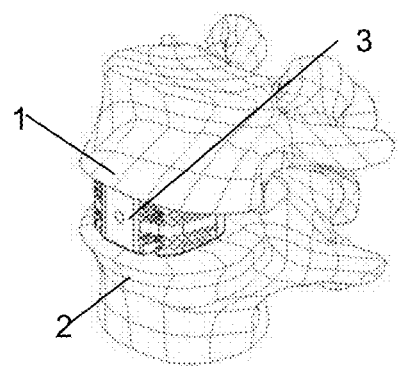
FIGS. 35*a*-35*k* a method of preparing a spine for anchoring a spine stabilization device according to the embodiments depicted in FIGS. 30-32.
Figure 35B:
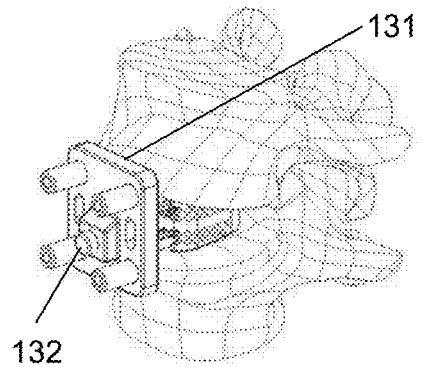
Figure 35C:
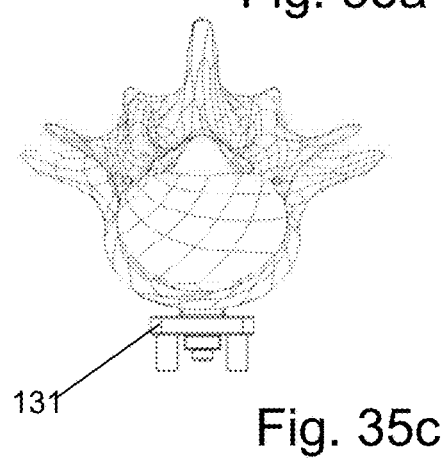
Figure 35D:
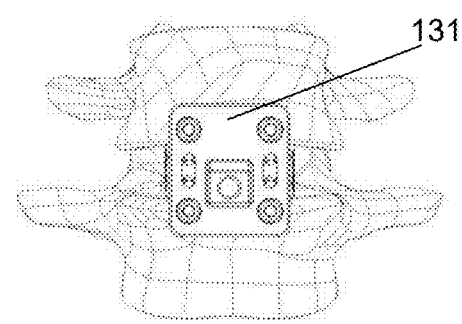

FIGS. 35a-35k, finally, illustrate method steps of a method of preparing anchoring of a spine stabilization device of the kind described referring to FIGS. 30-33, using an insertion kit. After the intervertebral disc (or remains thereof) has partly been removed, if necessary, the interbody spacer 3 is inserted in the space between the vertebral bodies (FIG. 35a). Then, a drill guide 131 is placed in a defined positional relationship with the intervertebral body. In the depicted embodiment, the drill guide is temporarily secured to the interbody spacer by means of a fastening screw 132 (FIGS. 35b-35d) or an other means. The drill guide comprises four drill guiding portions, the axes of which are essentially parallel to the median plane and to the sagittal plane, thus to the (local) dorsoventral axis (could also be at an angle to the axis and possibly to each other). Again, instead of a drill guide with four drill guiding portions, a drill guide with two drill guiding portions may be used twice.

Figure 35E:
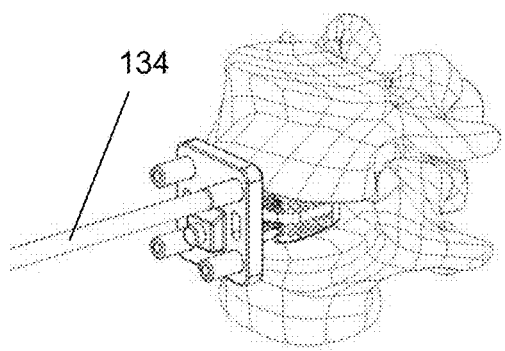
Figure 35F:
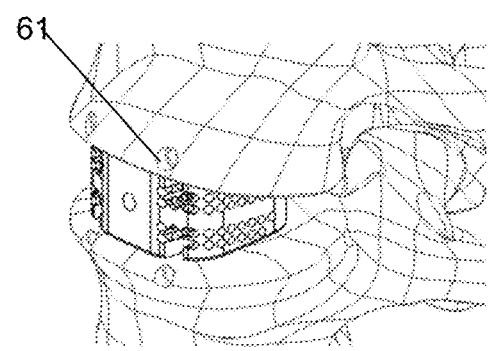
Figure 35G:
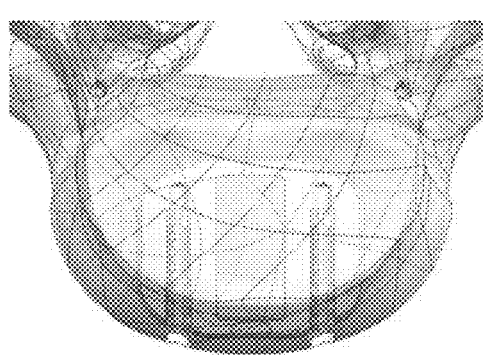
Figure 35H:
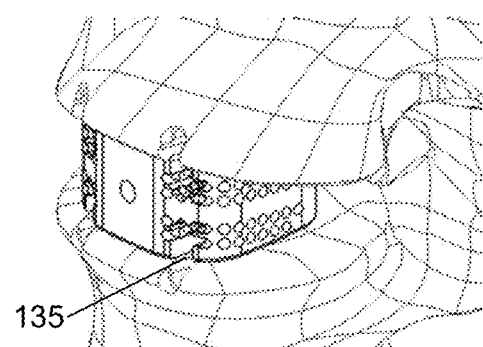
Figure 35I:
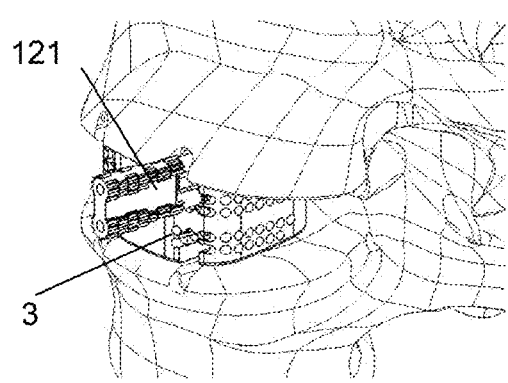
Figure 35J:
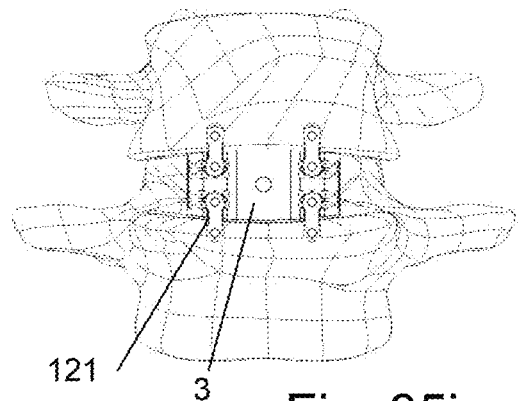
Figure 35K:
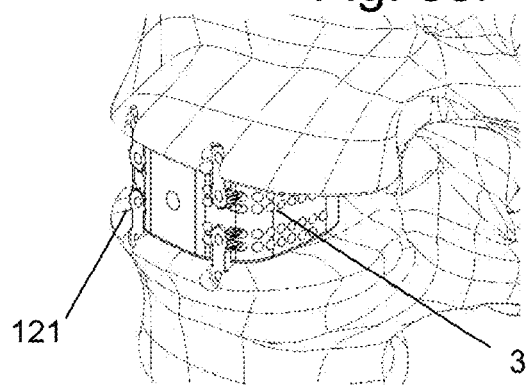

Thereafter, the pre-drilled holes 61 (or positioning holes) in the bone tissue are made. FIG. 35e illustrates a drill bit 134 of an according drill, the drill bit 134 being guided by the drill guiding portions. Parts of the vertebral body endplate underneath the pre-drilled holes 61 are thereafter removed down to the anterior surface of the interbody spacer 3 at least to a depth in the dorsal direction corresponding to the longitudinal extension of the bridge portion 128 of the anchoring devices to extend the recess 14 in the interbody spacer for the support portion into the vertebral body (FIG. 35h).

This is for example accomplished by a cutting caliper. Then, the anchoring devices are inserted and anchored e.g. with the aid of mechanical vibration, i.e. by a method as described in WO 2008/034 276, the disclosure of which is incorporated herein by reference in its entirety. In this anchoring process, the respective anchoring device is preferably firmly coupled, also using the guiding holes 126 (FIG. 32), to the sonotrode, or, if instead of vibrational energy, laser light is used, to a pushing tool which comprises a light guide ending at the distal tool face which is equipped for coupling the laser light into the anchoring device.

FIGS. 46-58 show tools and their application for implanting a spine stabilization device of the type described with respect to FIGS. 1-25 and 42-45, especially with nonzero sagittal angles to the median plane (thus like the embodiments of FIGS. 42-45). Especially, the differences to the approach illustrated in FIGS. 33a-33l are referred to.

Figure 46:
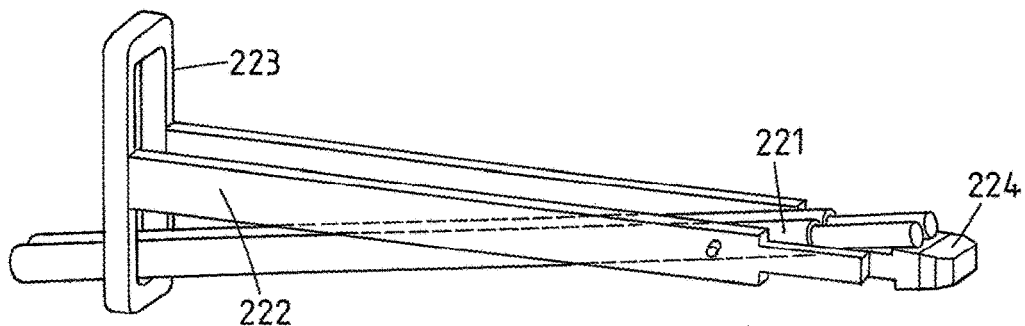
FIGS. 46-48 tools and steps for implanting a spine stabilization device according to the fifth aspect.

FIG. 46 shows a bone cutter 221 for the preparation of cavities for the loops 205. In contrast to the approach of 33a-33l, the cavities are in the vertebral body portion (in the anterior surface thereof) that is immediately adjacent the interbody spacer, and thus the removal of portions above and below the cavities (FIG. 33i) may not be necessary. A guide 222 defines both, the location of the cavities and—by means of a proximal guide frame 223—the angle. When the cavities are prepared, the drill guide is inserted with a spacer template 224 that has an approximate shape of the later inserted interbody spacer but no retention structures.

Figure 47:

FIG. 47 depicts a drill guide 231 that is used for the preparation of holes for the insertion of the tube portions or tube elements 51. The drill guide comprises a coupling portion 232 suitable for coupling the drill guide with the interbody spacer 3.

Figure 48:

As shown in FIG. 48, the interbody spacer 3 and the fixation device(s) (here of the kind shown in FIGS. 42 and 43) are inserted with the drill guide, and a drill guide guiding portion 233 guides the drill bit 235 at the chosen angle when the holes are prepared.

FIGS. 49-58 show a different instrumentation and its use. The embodiment depicted is suitable for the spine stabilization device of FIG. 45, however, the skilled person will be able to readily adapt the configuration (for example by re-arranging guiding portions of the tools) for other embodiments of the invention.

Figure 49:
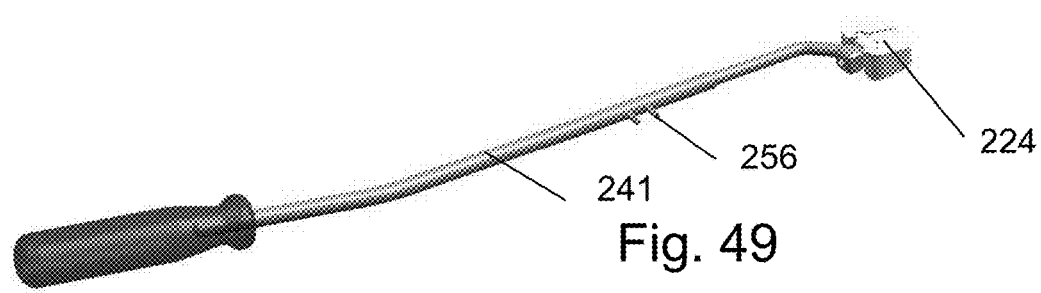
FIGS. 49-58 alternative tools and steps for implanting a spine stabilization device according to the fifth and/or sixth aspect.
Figure 50:
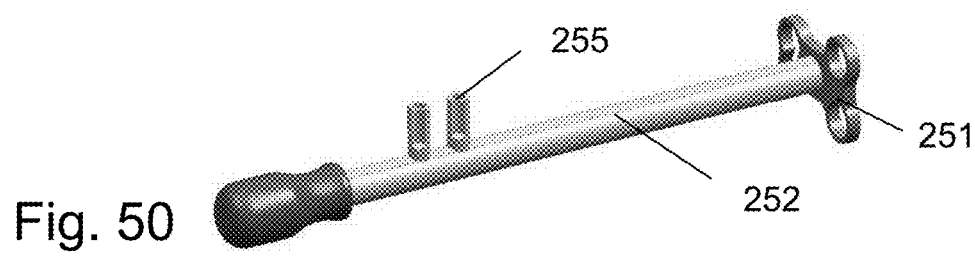
Figure 50A:
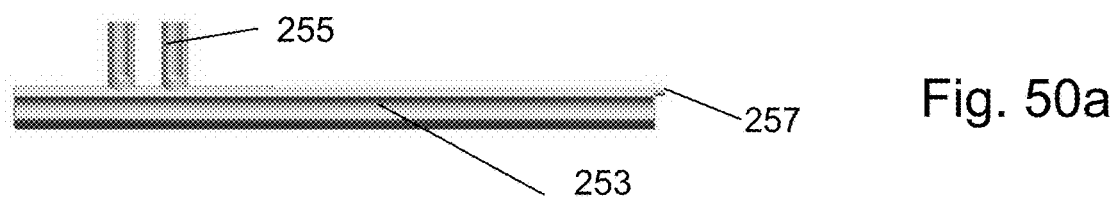
Figure 50B:

The handle device 241 shown in FIG. 49 is suitable holding an interbody spacer or a spacer template 224. In a first step, the spacer template is inserted in the prepared cavity between two vertebral bodies. To this end, a cutter template 251 affixed to a cutter template handle 252 as depicted in FIG. 50 is positioned. The cutter template handle 252 comprises a first handle part 253 (FIG. 50a) with a tube portion and a second handle part 254 (FIG. 50b) with a shaft portion. The shaft portion of the second handle part is guided within the tube portion of the first handle part. The second handle part comprises attachment means 255 for cooperating with corresponding attachment means 256 of the handle device 241.

The first handle part comprises a positioning peg 257 for defining a relative position of the cutter template handle 252 on the one hand and the handle device 241 and the spacer template 224 on the other hand.

Figure 51:
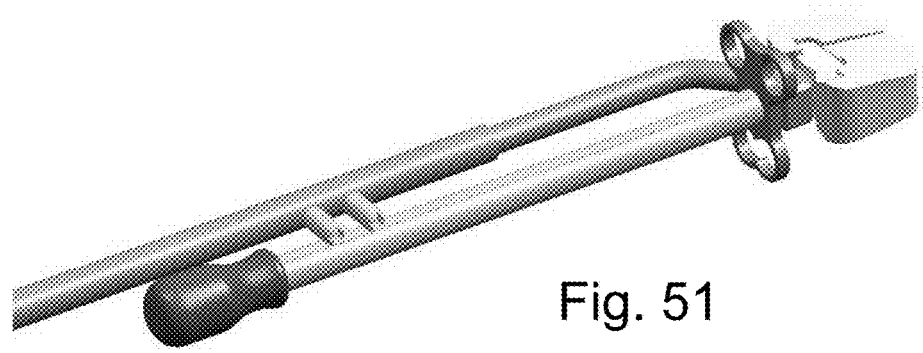

The handle device 241 with the spacer template 224 is assembled ex situ with the cutter template handle and the cutter template (FIG. 51). The thus resulting preparation assembly is inserted in the prepared cavity between the two vertebral bodies. If necessary, the surgeon may hammer onto the cutter template handle to apply enough force for the insertion.

Figure 52:
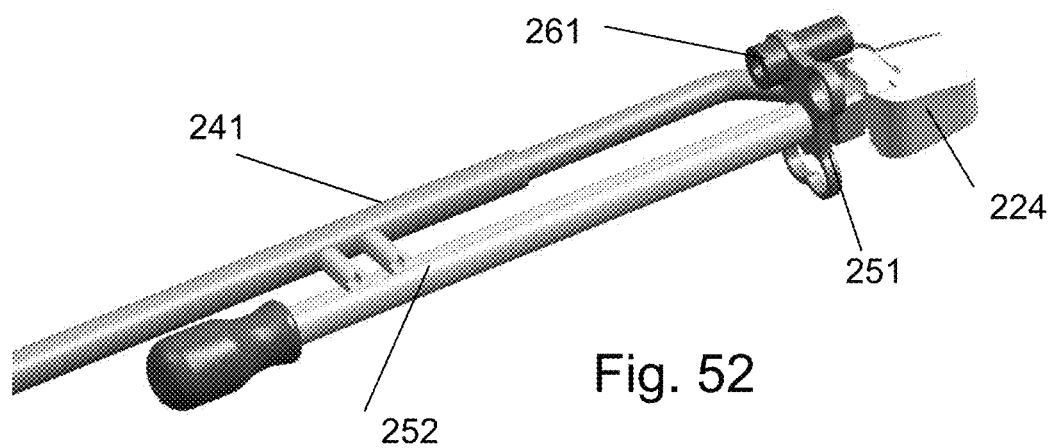

Then, as shown in FIG. 52, a punching tool 261 (that may comprise a—not shown) tool handle is used to prepare the cavities for the loops. The punching tool is guided by appropriately positioned guiding openings of the cutter template 251. The punching tool comprises a punching portion that is suitable for punching the shape of the cortical bone tissue to be removed into the cortical bone. In the punching step, the punching tool may be thrust forward manually by the surgeon, and if the punching tool has a circular symmetry (as is the case in the depicted embodiment), the surgeon may slightly twist the tool forth and back during punching.

Figure 53:
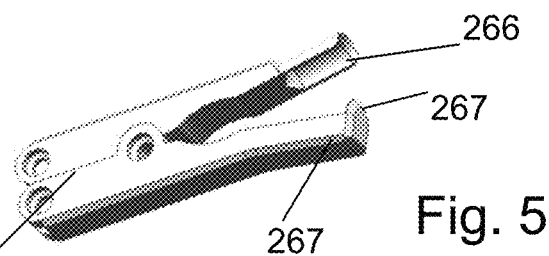

The bone tissue to be removed by punching may as a result of the punching hold within the punching tool. If this is not the case, it may be removed by an appropriate pincer tool 265 (FIG. 53). The pincer tool comprises a first pincher member 266 having the shape to be inserted into the groove created by the pinching tool, and a second pincher member 267 with an engagement-behind feature 267 that allows to reliably remove the tissue.

Figure 54:
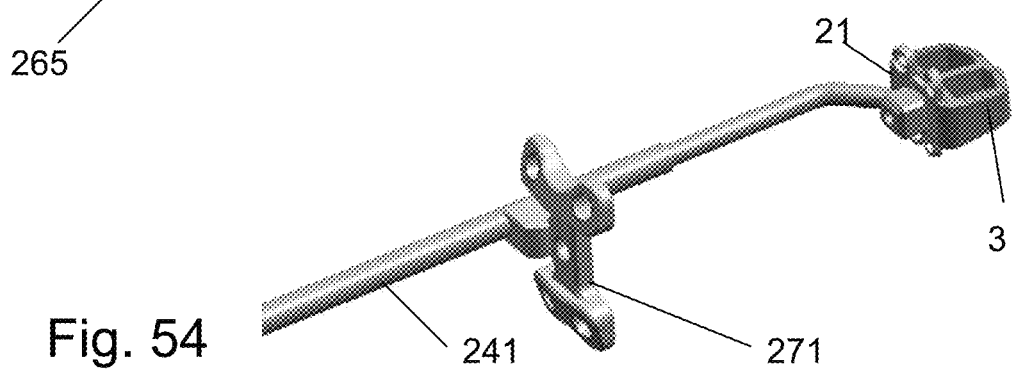

Thereafter, the preparation assembly is removed. The interbody spacer 3 and the fixation device body 21 are assembled with the handle device 241. Also an aiming device 271 is affixed to the handle device 241. The aiming device is at a substantial distance from the fixation device body 21 towards the proximal side. The resulting preanchoring assembly as shown in FIG. 54 is then inserted and positioned in the prepared cavity.

Figure 55:
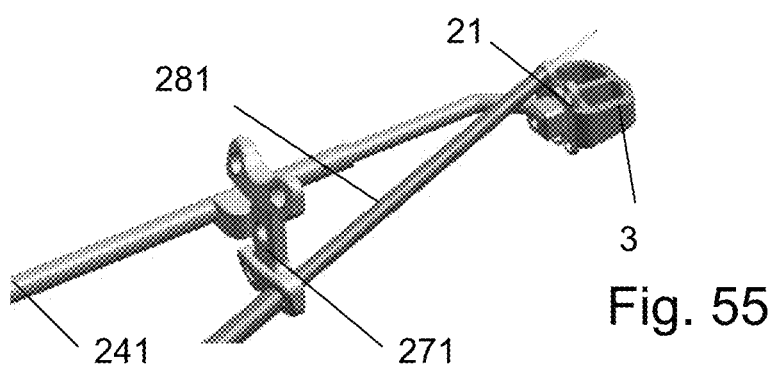

Then, an a awl 281 is used to extend the cavities created by the punching tool into the cancellous bone (FIG. 55). The awl may comprise a stop shoulder that causes a distal movement to stop when the stop shoulder abuts against the loops and prevents the awl from being inserted too far.

The aiming device comprises a four guiding holes thus a number of guiding holes that corresponds to the number of receiving openings of the fixation device. The awl (as well as the devices in the steps to follow) is placed in a crossed arrangement so that the angles to the median plane and to the sagittal plane are as desired. To make this possible, and also for better visibility, the handle device 241 has an eccentric shape.

Figure 56:
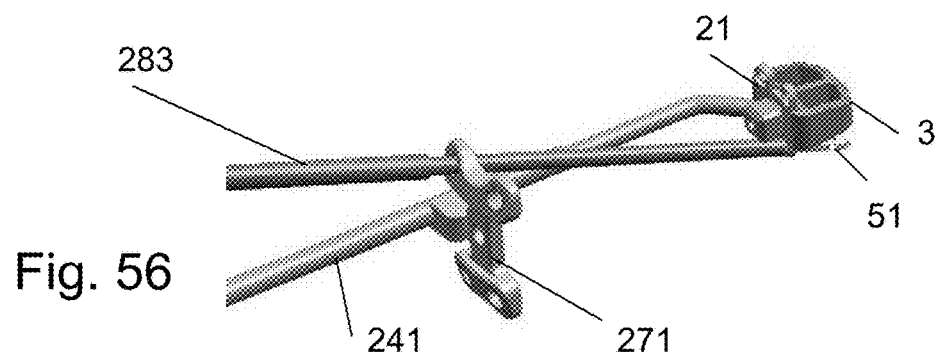

FIG. 56 illustrates the step of inserting the tube elements 51 (or sleeves) by means of a tube element insertion tool 283 that is shaped to hold the sleeve to be inserted at its distal end and to release it once it is held in place—for example by sufficient friction with the cancellous bone tissue.

After placement of all sleeves—one after the other—the anchoring process is carried out. To this end, a guiding tube 291 (FIG. 57) is placed guided by the same two-point guiding mechanism constituted by the aiming device and the fixation device body 21. The anchoring material element (not shown in the figure) and a sonotrode 292 are inserted from the proximal side into the tube. As alternatives, the anchoring material element may be partly introduced into the sleeve prior to placing the guiding tube, or the anchoring material element may be mounted to the sonotrode ex situ. Then, the mechanical oscillations impinge on the sonotrode, while the sonotrode is pressed towards the distal side, so that the thermoplastic material of the anchoring material element starts getting liquefied and penetrates into the cancellous bone tissue adjacent the lateral openings of the sleeve. This is repeated for all four tube elements 51.

This way to proceed and the tools described referring to FIGS. 49-58 feature the substantial advantage that tissue surrounding the operation site (except the bone of the vertebral bodies themselves) may not come into contact with power-driven rotation or other mechanical movement. The risk of damaging vital tissue—such as blood vessels—by the surgical operation is therefore substantially reduced. Nevertheless, the approach according to the invention makes possible that the operation site may be accessed straight, and no difficult-to-handle deflection tools—such as cardan joints—are needed.

A variant of the approach shown in FIGS. 49-58 is now described referring to FIGS. 70-81. The variant is described for the spine stabilization device shown in FIGS. 67-69, however, with slight modifications accounting for differences in the geometry, it also applies to other embodiments. The following description focuses on the difference to the previously described methods and tools.

Figure 70:
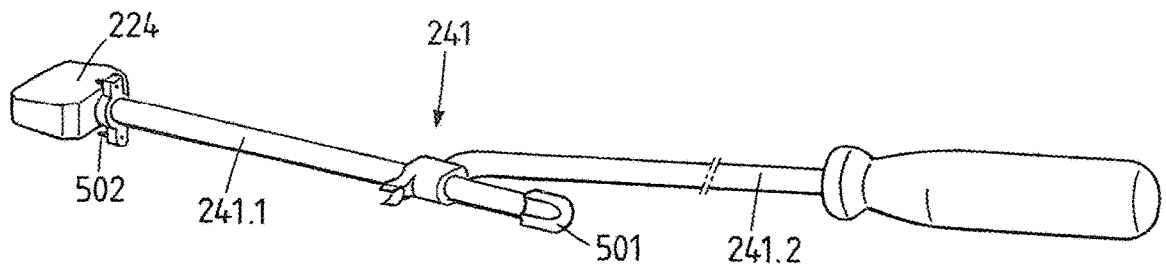
FIGS. 70-80 yet other alternative tools and steps for implanting a spine stabilization device according to the first and/or fifth aspect of the invention.

The handle device 241 shown in FIG. 70 is equipped for holding an interbody spacer template 224 that has approximately the size of the interbody spacer to be implanted later but that does not have retention structures and is thus easier to remove from between the vertebral bodies. The handle device 241 comprises a proximal piece 241.2 and distal piece 241.1. The distal piece 241.1 is straight and has a proximal knob 501 against which the surgeon may hammer to drive the spacer template between the vertebral bodies if the manual force does not suffice. The proximal piece 241.2 is angled to get an optimal view don the spacer template 224 during operation.

Figure 71:
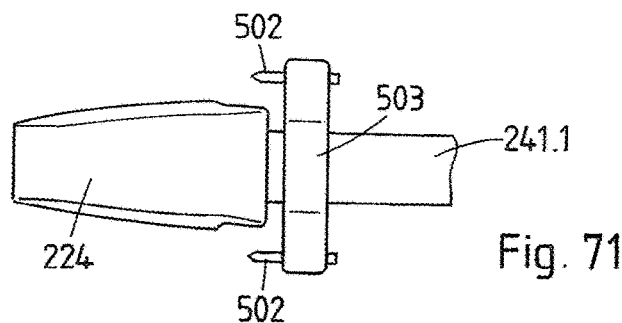

As can best be seen in FIG. 71, proximate to the distal end of the handle device 241 (thus close to the spacer template 224 when the same is affixed to the handle device) the handle device comprises a holding flange with a plurality of holding spikes 502. In the illustrated embodiment, two holding spikes 502 are present for engaging in the superior (cranial) and inferior (caudal) vertebral bodies, respectively. The holding flange constitutes a mechanical stop for the insertion of the spacer template at the optimal depth. The holding spikes 502 protrude distally from the holding flange and are suitable to engage into bone tissue of the upper and lower vertebral bodies (and/or other tissue) to prevent a movement of the construct during the subsequent steps. The spikes in the depicted embodiment also have a proximal portion protruding proximally from the holding flange body and being suitable of cooperating with a corresponding indentation of the cutter template 251 to orientationally fix the same to the spacer template.

Figure 72:
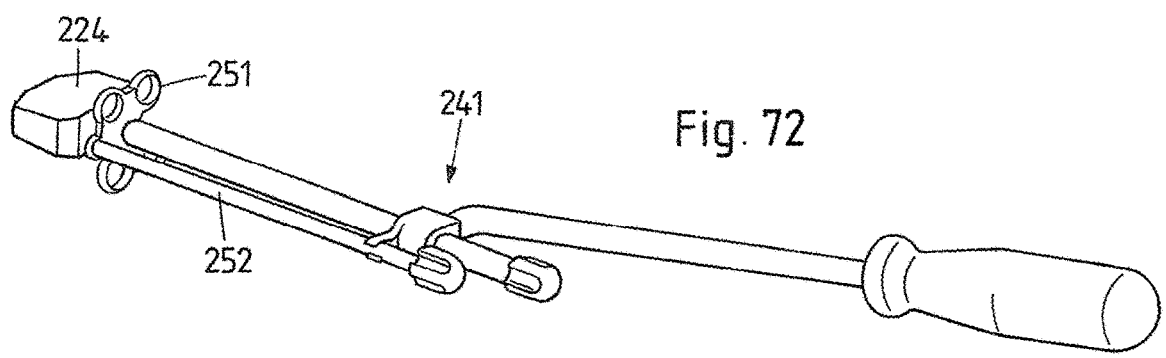

FIG. 72 shows the arrangement with the cutter template 251. The cutter template is introduced using the cutter template handle 252 to which it is affixed. The cutter template handle 252 with the cutter template 251 is introduced by the cutter template 251 first being clipped onto the distal piece of the handle device 241 (first clip mechanism 254), then being slidingly moved towards the distal direction, and then the proximal side of the cutter template handle 252 being clipped onto a second clip mechanism 255 that in the depicted embodiment is constituted by a feature of the proximal handle device piece 241.2.

Figure 73:
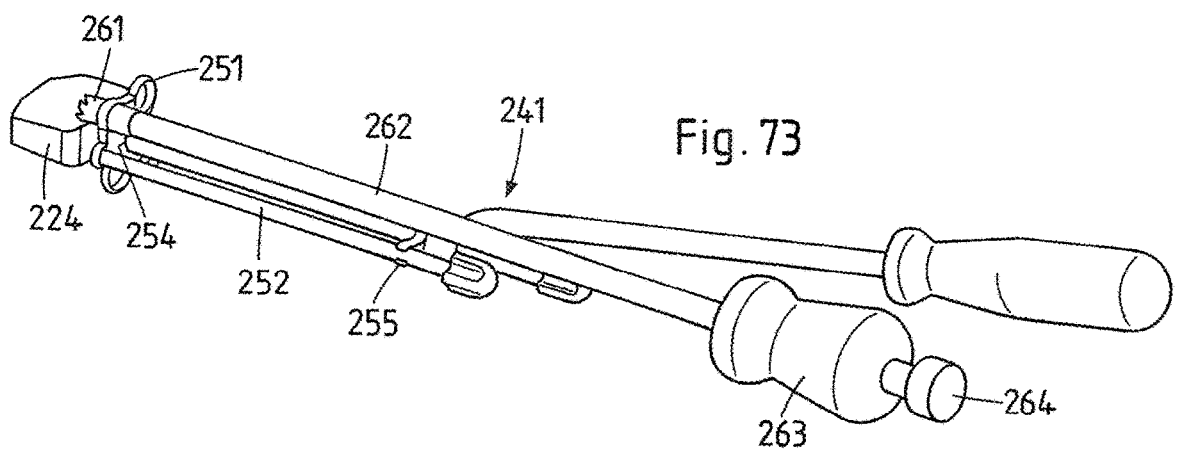
Figure 74:
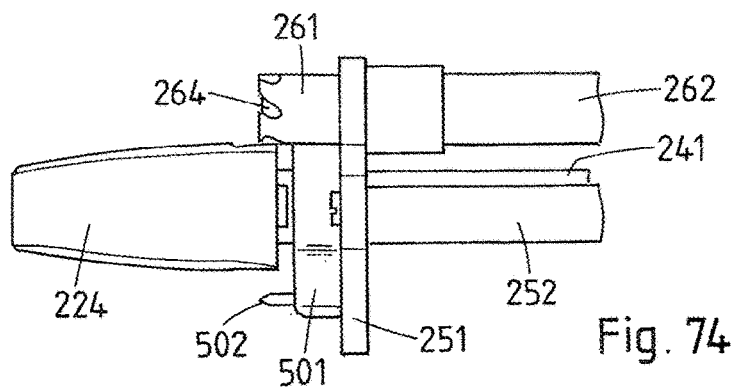

FIGS. 73 and 74 illustrate the cutting (or punching) step, by which the surgeon may remove the desired portions of the cortical bone at the circumferential surface of the vertebral body. The punching tool 261 is guided by the cutter template 251 and held by a punching tool handle 262 with a punching tool knob 263 that the surgeon may move circularly. Through a longitudinal bore of the punching tool handle 262, a pusher 264 may be introduced after the punching step. The pusher serves to remove the bone tissue from the inside of the cutter. If the bone tissue remains weakly attached to the vertebral body, a pincer tool 265 as illustrated in FIG. 53 may be used.

After completion of the punching, the spacer template 224 is removed.

Figure 75:
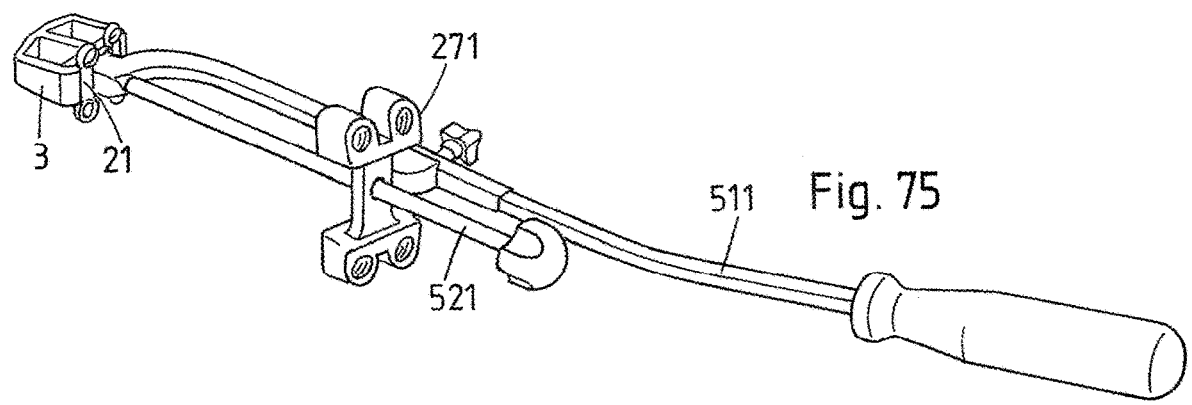

FIG. 75 depicts an assembly for introduction of the interbody spacer 3. In the here-illustrated embodiment, a spacer handle 511 different from the handle device 241 used to hold the spacer template is used. Also the spacer handle is angled to get an optimal view in the implant. Between the spacer handle 511, the interbody spacer 3 and the fixation device body 21 there is a screwed connection (hence the central hole 205), and a puncher 521 may be used both, as a screw driver and as a tool to hammer in the interbody spacer 3. The aiming device 271 may either comprise a proximodistal through hole through which the puncher reaches, or it may be affixed to the spacer handle 511 only after removal of the puncher 521.

Instead of a screwed connection, other fixation means may be used, such as a snap closing-like mechanism, a bayonet-like mechanism or any other fastening technique that has a high reliability.

Figure 76:
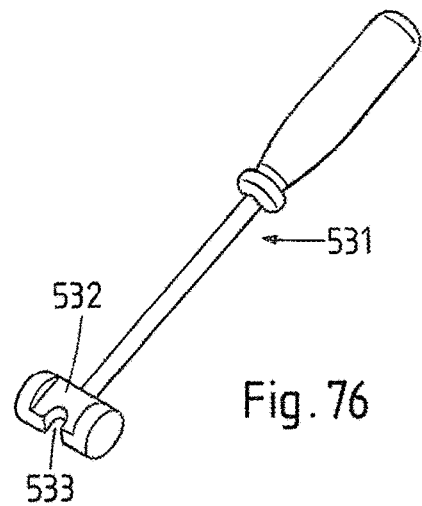

FIG. 76 shows an example of a specifically adapted hammer device 531 that may be used during the surgical operation and that may be comprised in the kit of parts for the surgeon.

Figure 77:
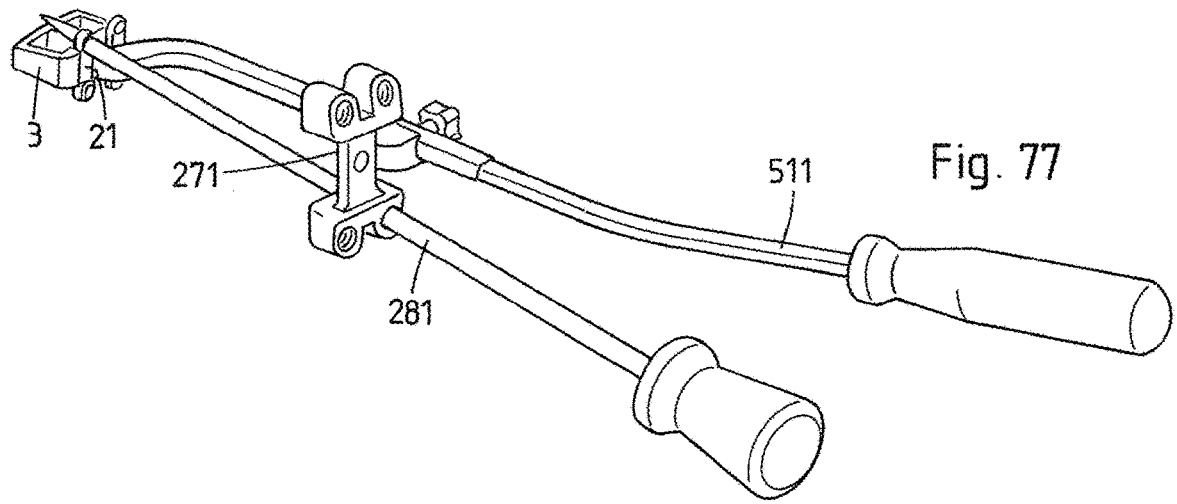

If desired or necessary, an awl 281 guided by the aiming device 271 can be used to extend the cavities created by the punching tool into the cancellous bone tissue (FIG. 77). The awl reaches through the appropriate guiding opening of the aiming device and through the receiving openings of the fixation device body.

Figure 78:
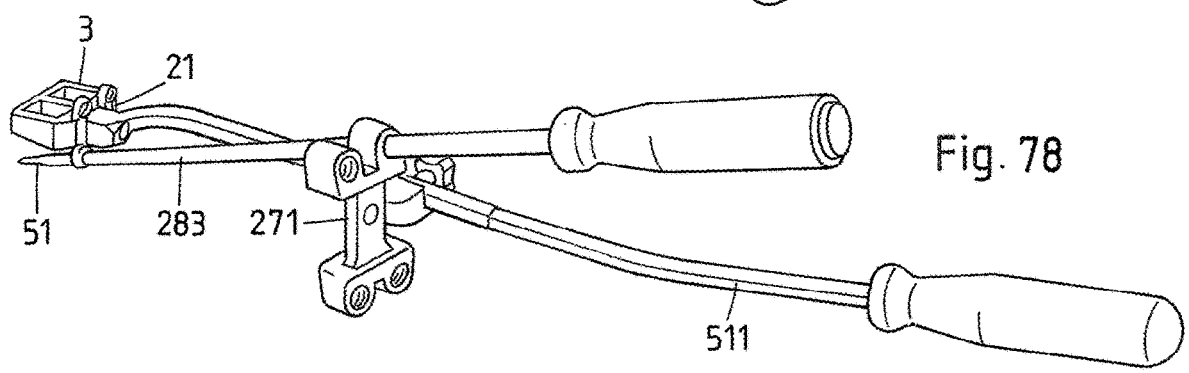

The insertion of the tube elements 51 is shown in FIG. 78. The tube element insertion tool 283 comprises a distal portion adapted to cooperate with the centering step (or centering shoulder) of the respective tube element 51 to provide a self-holding mechanism during insertion. If the tube element 51 comprises the self-reaming structure, it is advantageously inserted by a straight distal movement without any twisting, through the respective opening of the insertion device and the receiving opening of the fixation device body 21. If the surgeon's manual force is not sufficient to fully insert the sleeve element, the hammer device 531 may be used. To that end, also the tube element insertion tool 283 has a handle that is suitable of being hammered. After the tube element 51 has reached its position, it snaps in locked to the fixation device body 21 due to the ramp portion.

Figure 57:
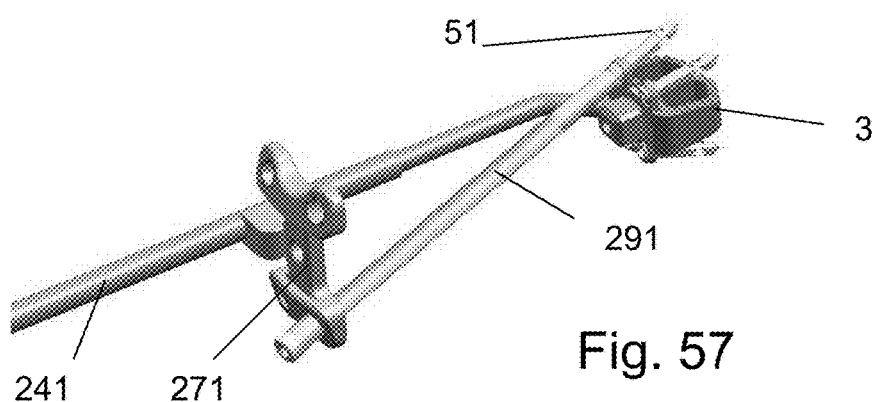
Figure 58:
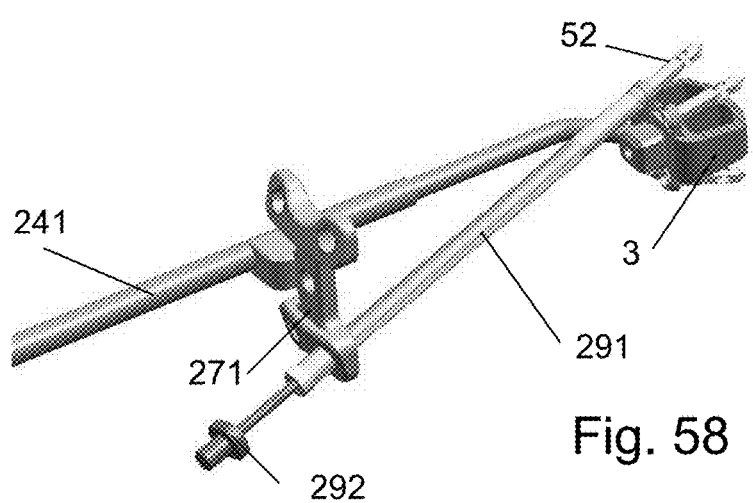
Figure 59:
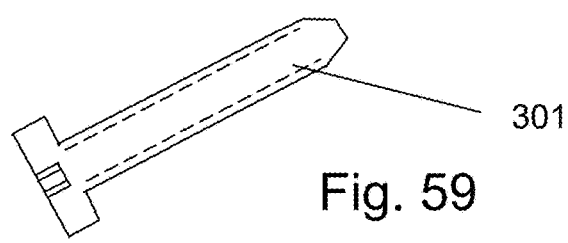
FIG. 59, schematically, an alternative fastener.
Figure 79:
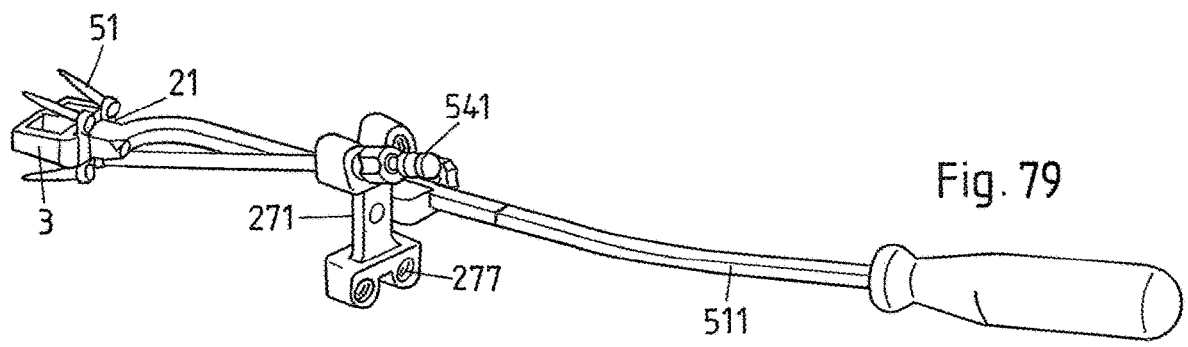
Figure 80:
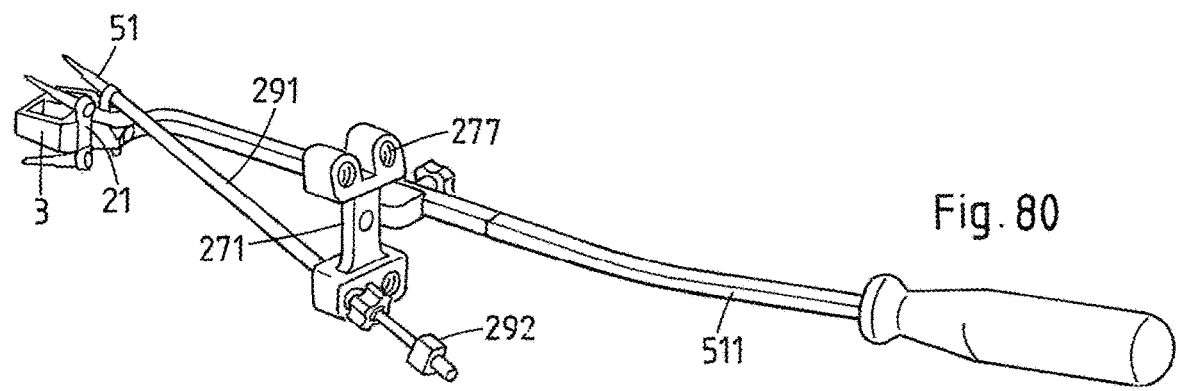

The aiming openings of the aiming device 271 comprise a threaded portion 277 to co-operate with an according outer thread of the guiding tube 291 that otherwise has the same function as in the embodiment of FIG. 57. The thread serves to connect the guiding tube 291 and the aiming device so as to ensure a reliable fixation during the subsequent application of mechanical energy and also to make sure that any force acting into the distal direction acts onto the anchoring material element. As illustrated in FIG. 79, optionally a control instrument 541 may be used to check the alignment between the guiding tube 291 and the respective tube element 51: if the control instrument—being basically a rod with a grip—is not easily inserted to a sufficient depth, alignment is not satisfactory and correction is required. Thereafter, the anchoring material element is inserted through the guiding tube, and the sonotrode 292 is inserted into the guiding tube 291 (FIG. 80). It is also possible to pre-assemble the sonotrode 292 and the anchoring material element. Then, the mechanical oscillations impinge on the sonotrode, while the sonotrode is pressed towards the distal side, so that the thermoplastic material of the anchoring material element starts getting liquefied and penetrates into the cancellous bone tissue adjacent the lateral openings of the sleeve. This is repeated for all four tube elements 51.

An automated insertion and anchoring apparatus may be used for causing the vibrations of the sonotrode. A coupling between the guiding tube 291 and the housing 311 of the may be done by a quick connector or a similar coupling means. In some situations, it may be necessary that a spine stabilization device is removed. Removal of a fastener constituted by the anchored tube elements with the liquefied and re-solidified anchoring material may be done as follows: for each tube element, in a first step, a threaded removal tool is screwed in in the elongate cavity formed by the tube element. The removal tool may comprise, proximal to the threaded section, a shaft portion and a grip.

If necessary, an instrument engages the gripping slot to prevent a rotation of the tube element due to the torsion it is subject to because of the screwing. Then, the removal tool is pushed towards the proximal side to extract the tube element. If necessary, hammering may be used to support the pushing. To that end, the hammer 531 comprises a flat section 532 and a slit 533. The slit serves for guiding the hammer along the shaft portion, and the flat section may hammer against the distal end face of the grip.

Instead of screwing a removal tool into the anchoring material in the elongate cavity of the anchored tube element as described above, it is possible to achieve a better grip between the removal tool and the anchored tube element by gripping the tube element itself at the openings through which the anchoring material was initially pressed into the vertebral bone tissue. For this purpose, the anchoring material in the anchored tube element is first removed from the elongate cavity with the aid of a drill or rotating cutter to reach at least a proximal portion of the named openings. Then a removal tool comprising a plurality of distal members which can be spread radially is introduced into the elongate cavity, the distal members being aligned with the openings of the tube element. The distal members are then spread into the openings where they dig into the anchoring material which still fills these openings, wherein the spreading is advantageously limited to an extent which corresponds substantially with the thickness of the tube wall. With the distal members such spread, the removal tool cannot be removed from the vertebral bone without also removing the tube member. For ensuring safe operation of the distal members during removal it is advantageous to provide an active spreading mechanism, e.g. a spreading body (e.g. head of a spreading screw) which is moved proximally between the distal members when the removal tool is positioned in the elongate cavity, instead of relying on resilient distal members which are supposed to automatically spread and dig into the anchoring material due to the smaller resistance to the elastic force exerted by the anchoring material than by the tube element. For removing the tube element from the vertebral bone, the removal tool with the distal members spread and therewith dug into the anchoring material in the openings is then pulled away from the vertebral bone and the interbody spacer e.g. in the same way as described further above for the alternative removal method.

In both approaches, the one of FIGS. 46-48, and the one of FIGS. 49-58, as well as in the variant of FIGS. 70-80, it is possible to use a combined sleeve insertion and anchoring tool, as depicted in FIGS. 60-66. The combined sleeve insertion and anchoring tool may be used also for purposes different from anchoring tube elements for spine stabilization devices of the herein described kind but may also be suitable for anchoring tube elements for anchoring other implants.

FIG. 60 depicts the insertion and anchoring tool 310 with a handgrip/housing 311 that houses an ultrasound converter, and with a guiding and protecting tube 291. The housing 311 together with the ultrasonic converter and other elements (such as a spring or similar for automatically excerpting the necessary force into the distal direction on the sonotrode) together form the apparatus for automated insertion. The coupling between the apparatus housing 311 and the guiding tube 291 is such as to completely shield the sonotrode in the mounted, assembled state. The coupling may be a screw-type coupling, a quick connector, or any other suitable coupling.

FIG. 60 also shows the sleeve (the tube element). FIGS. 61-66 show a possibility of a coupling between the guiding tube 291 and the tube element 51.

The detail depicted in FIGS. 61-63 shows that in vicinity of the distal end of the tube 291, the tool 310 comprises a grasper 312 for holding the sleeve. For the anchoring process, the grasper 312 is pulled back into the retracted position (FIGS. 63, 64), in which the tube element 51 is firmly held by the grasper, and the sonotrode 292 couples mechanical vibrations into the anchoring material element 31 while pressing the same towards the distal side, until liquefied portions 34 exit from the lateral openings. After completion of the anchoring process, the grasper releases the anchored tube element 51 (FIGS. 64, 66).

Instead of the coupling mechanism of FIGS. 61-66, also other coupling mechanisms between the tube elements (or other element with the elongate cavity) and the guiding tube may be used, including screw connections and including mechanisms that may couple the guiding tube 291 with the tube element (or other element with the elongate cavity) prior to coupling the apparatus (handpiece) with the guiding tube.

Instead of mechanical vibration, also a rotational movement may be used to liquefy the anchoring material element, or, as discussed hereinbefore, other kinds of energy, for example electromagnetic radiation guided through a waveguide that goes through the guiding tube, may impinge on the anchoring material element.

As a further alternative, an initially liquid material such as a curable material may be pressed through the guiding tube and into the sleeves and into the cancellous bone tissue, whereafter the material is hardened.

As yet another alternative, a for example conventional fastener may be used instead of the sleeves (tube elements) with the anchoring material portions, such as an other fastener of a kind discussed in this text that comprises liquefiable material, or a surgical screw 301 that for example may comprise an osseointegration supporting surface structure and/or a suitable coating, such as a HA coating.

Figure 36:
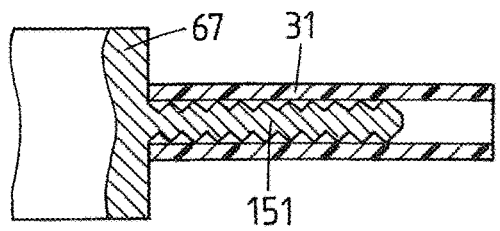
FIG. 36 the principle of guiding the anchoring material element by means of e.g. a sonotrode.

FIG. 36 illustrates an anchoring material element 31 for embodiments of the first or second aspect of the invention, mounted a sonotrode 67 having a sonotrode tip 151. The sonotrode tip is provided with retaining structures (such as a thread) for a fixed coupling with the anchoring material element; it is also possible that the anchoring material element is held just by frictional force. In embodiments where the anchoring structure includes an elongate cavity accessible from anterior, the length of the sonotrode tip 151 is preferably less than the length of the elongate cavity, so that the proximal end of the sonotrode tip also defines a stop for the anchoring process.

The sonotrode tip 151 has a guiding effect on the anchoring material element, and this has shown to provide advantageous results in many configurations.

An analog guiding mechanism with a double sonotrode tip (not shown) may be used for embodiments of the third aspect of the invention.

The embodiment of FIGS. 38 and 39 is a further example of a spine stabilization device according to the first and second aspect of the invention. FIG. 38 shows an upper part of the interbody spacer 3 inserted in the space between two vertebral bodies (the upper vertebral body 1 being shown in the figure), with two fixation devices 4, and FIG. 39 depicts a top view of the interbody spacer 3. The interbody spacer 3 comprises two channel-like recesses 74 at the top surface and two channel-like recesses at the bottom surface. Each recess is shaped to accommodate a guiding portion 161 of a fixation device 4. The guiding portion of the fixation device may have a dovetail shaped or otherwise undercut (in section) shape so as to secure the vertebral body 1 and the interbody spacer against a movement away from each other. The fixation devices further each comprise an anchor 162 for anchoring the fixation devices in cancellous bone tissue of the vertebral body. The anchor may for example be configured like the anchors described referring to FIGS. 4-8 and include a tube portion in physical continuity with the guiding portion 161 and an anchoring material element to be inserted into the elongate cavity defined by the tube portion. It may alternatively be configured like anchors of other embodiments described hereinabove.

As shown in FIG. 39, the recesses 74 (and thus, if present, also of the pre-drilled holes in the vertebral bodies, are non-parallel with respect to each other, in accordance with the second aspect of the invention, and securing the interbody spacer against escaping to the dorsal direction, and to the ventral direction, whereas the support portion 6 may additionally contribute to the securing against escaping to the ventral direction.

The above-described embodiments with the exception of the embodiment of FIGS. 30-32 and 37 may be modified for an anchoring process that includes anchoring by a cement or other not thermoplastic material that is in an initial state liquid. To this end, the liquid anchoring material is introduced, from an anterior side (or potentially any other side, thus anterior, anteriolateral, lateral, posterolateral or posterior side if different configurations are used) in an elongate cavity like the one of FIG. 4-6, 10-19, 22, or 28 and pressed out through the lateral openings.

FIGS. 40 and 41 yet depict an embodiment of the fourth aspect of the invention. The spine stabilization device comprises an interbody spacer 3 and two fixation devices 4. The fixation devices' fasteners for fastening the devices to the vertebral bodies 1, 2 are surgical screws 171. As alternatives, other fasteners according to the state of the art could be used. As yet further alternatives, the fasteners could be configured in accordance with the anchors of embodiments of the first aspect of the invention; then the spine stabilization device in addition to the fourth aspect also corresponds to the first aspect of the invention. In addition or as an alternative, the fixation devices may comprise guiding protrusions like the ones of the embodiments of FIG. 4 and cooperate with corresponding indentations for the spine stabilization device to also correspond to the second aspect of the invention.

The fourth aspect of the invention is especially suited for vertebrae the vertebral bodies of which comprise, towards the lower respectively upper endplates, bulges 173 towards the ventral side. A method of implanting a spine stabilization device according to the fourth aspect includes the step of anteriorly removing cortical bone of the vertebral body in the region of the bulge 173 to provide a countersink for the support portion 6 but to leave the cortical bone intact in a central region of the anterior wall of the respective vertebral body. The fastening is then achieved in the central region (for example position along the spine axis is in the middle two quarters or in the middle third of the vertebral body extension). This features the advantage that the fixation devices are countersunk so as not to harm vessels and other organs arranged ventrally of the vertebral bodies, and nevertheless anchoring is at least partially in the cortical bone.

Nevertheless, devices and methods according to aspects of the invention are especially suited for an anchoring process that includes liquefying, by means of thermal energy locally provided through at least one of friction due to mechanical oscillation or rotation, local absorption of laser light, and local electric heating, initially solid elements comprising thermoplastic material at least partly. Such anchoring processes are specifically advantageous not only for application in at least partly cancellous bone tissue but also regarding the configurations (insertion angles etc.) of the devices as herein described.

Various further embodiments may be envisaged without departing form the scope and spirit of the invention. For example, while the figures for illustration purposes generally show lumbar vertebrae, the invention may also be applied to all other vertebrae, especially including cervical, and thoracic vertebrae.

The anchoring process in the embodiments in which liquefaction of polymeric material is included may be done manually, or at least partially automated. For the latter, the skilled person is for example referred to the teaching of US2009 018471 or U.S. application Ser. No. 61/259,383 (the teaching referring to an automated anchoring tool), both incorporated herein by reference in their entirety.

While all figures that show the spine stabilization device in a state inserted in the spine relate to a spinal fusion implant replacing an intervertebral disc, the teaching of all figures may also be used for the situation where an entire vertebra and the adjacent vertebral disc is replaced. Further, embodiments of the invention that do not require a dimensionally stiff interbody spacer—they include but are not limited to the embodiments of FIG. 18, Fig. (without the guiding portions 24), FIG. 21, and FIGS. 30-32—may be used also for intervertebral disc prostheses.

While all methods described above as examples comprise the insertion of the interbody spacer being prior to the insertion of the fixation device(s), this need not always be the case. Especially, in the case of insertion of the interbody spacer from dorsal directions, the fixation devices may be introduced, for example from anteriorly, prior to the insertion of the interbody spacer. While this is not compatible with the teaching of FIG. 3, as an alternative a securing means may be provided in these embodiments, such as a snap fit connection.

While many hereinbefore described embodiments comprise tube elements and anchoring material elements that are liquefied at least partially inside the tube elements, and the material is pressed out therefrom, these embodiments may be realized with other fasteners of kinds described in the present text also.

Figure 83:
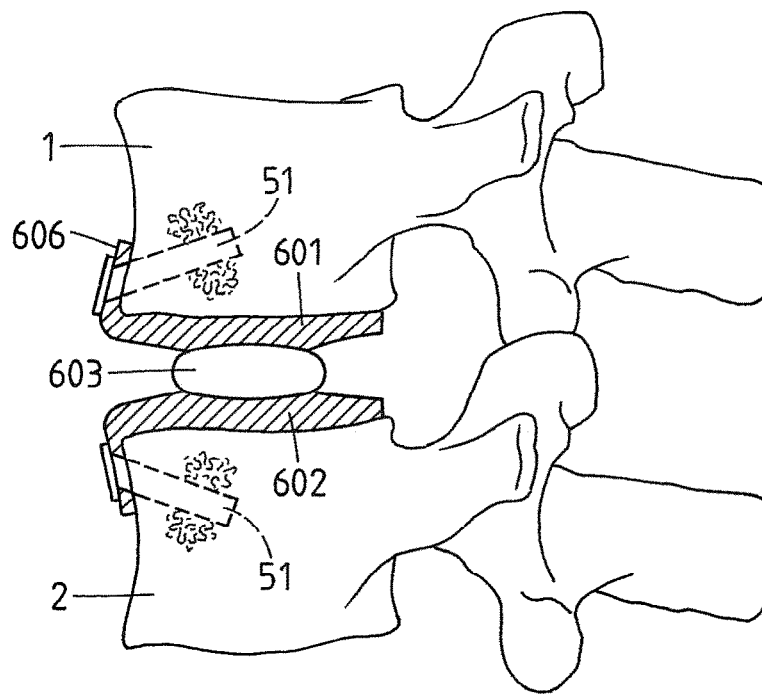
FIG. 83 schematically the application of the principle of embodiments of the invention to an intervertebral disc implant.

The principles of the aspects of the invention in this text and figures have been described referring to a spine stabilization device comprising a dimensionally stiff interbody spacer. An example of a surgical device for a different configuration is shown in FIG. 83. FIG. 83 illustrates an intervertebral disc implant inserted between two vertebral bodies 1, 2. The intervertebral disc implant comprises a disc element 603 held by an upper retaining element 601 and a lower retaining element 602. The retaining elements 601, 602 are movable to some extent relative to one another by the articulating function of the disc element 603.

Each of the retaining elements in the depicted configuration comprises a dimensionally stiff support portion 606 with at least one receiving openings through which a fastener of the kind discussed hereinbefore can be inserted. In the depicted configuration, the fastener comprises a tube element 51 with lateral openings through which anchoring material of an anchoring material element may exit to interpenetrate cancellous bone tissue of the respective vertebral bodies 1, 2. In the illustrated embodiment, the support portion 606 comprises a rim along the anterior surface of the vertebral body 1, 2 so that the fasteners may be introduced, as in above-discussed embodiments of the stabilization device, from the circumferential surface. However, it is not excluded to provide the receiving openings so that an introduction at least partially through the endplates is possible.

What is claimed is:

1. A spine stabilization device, comprising:
   an interbody spacer shaped to be inserted between a vertebral body of an upper vertebra and a vertebral body of a lower vertebra, and comprising a top surface oriented towards a lower endplate of the vertebral body of the upper vertebra and a bottom surface oriented towards an upper endplate of the vertebral body of the lower vertebra;
   a plurality of anchoring material elements including a thermoplastic material in a solid state,
   a plurality of cavities, each cavity having a proximal entrance into the cavity and a distal exit out of the cavity, wherein a respective anchoring material element of the plurality of anchoring material elements is insertable through the proximal entrance while the respective anchoring material element remains accessible for energy to impinge upon the respective anchoring material element,
   wherein at least a first cavity of the plurality of cavities is arranged adjacent to the upper vertebra and comprises at least a first distal exit, when the interbody spacer is inserted between the vertebral body of the upper vertebra and the vertebral body of the lower vertebra, the first distal exit faces bone tissue of the upper vertebra, whereby during an anchoring process with energy impinging on a first anchoring material element inserted in the first cavity, anchoring material of the first anchoring material element is capable of liquefying within the first cavity in direct contact with a wall of the first cavity, flowing out of the first cavity through the first distal exit, and flowing into structures of the bone tissue of the upper vertebra,
   and wherein at least a second cavity of the plurality of cavities is arranged adjacent to the lower vertebra and comprises at least a second distal exit, when the interbody spacer is inserted between the vertebral body of the upper vertebra and the vertebral body of the lower vertebra, the second distal exit faces bone tissue of the lower vertebra, whereby during an anchoring process with energy impinging on a second anchoring material element inserted in the second cavity, anchoring material of the second anchoring material element is capable of liquefying within the second cavity in direct contact with a wall of the second cavity, flowing out of the second cavity through the second distal exit, and flowing into structures of the bone tissue of the lower vertebra.

2. The spine stabilization device according to claim 1, wherein the anchoring material is capable of being liquefied and pressed into structures at least of cancellous bone tissue after liquefaction, by a joint action of a pressing force and at least one of mechanical vibration, absorption of electromagnetic radiation of the visible or infrared frequency range, electric heating, and of hardening thereafter to form a positive fit connection with the cancellous bone tissue.

3. The spine stabilization device according to claim 1, wherein the first and second distal exits each are shaped to allow, referring to an axis of each of the first and second cavities, a radial outflow of the anchoring material.

4. The spine stabilization device according to claim 1, wherein the plurality of cavities belongs to the interbody spacer.

5. The spine stabilization device according to claim 1, further comprising a fixation device shaped to be mounted relative to the interbody spacer to hold the interbody spacer in place, the fixation device comprising at least one of the plurality of cavities.

6. The spine stabilization device according to claim 5, wherein the fixation device comprises an upper anchoring portion comprising at least the first cavity and a lower anchoring portion comprising at least the second cavity, and a bridge connecting the upper and the lower anchoring portion.

7. The spine stabilization device according to claim 6, wherein the upper anchoring portion protrudes above the top surface of the interbody spacer and the lower anchoring portion protrudes below the bottom surface of the interbody spacer.

8. The spine stabilization device according to claim 1, wherein the interbody spacer further has at least one through opening extending through the interbody spacer from the top surface to the bottom surface.

9. The spine stabilization device according to claim 1, comprising,
   in addition to the first cavity, a third cavity of the plurality of cavities, the third cavity having a third distal exit out of the third cavity, the third distal exit facing the bone tissue of the upper vertebra when the interbody spacer is inserted between the vertebral body of the upper vertebra and the vertebral body of the lower vertebra, and,
   in additional to the second cavity, a fourth cavity of the plurality of cavities, the fourth cavity having a fourth distal exit out of the fourth cavity, the fourth distal exit facing the bone tissue of the lower vertebra when the interbody spacer is inserted between the vertebral body of the upper vertebra and the vertebral body of the lower vertebra.

10. The spine stabilization device according to claim 1 having an essentially plane surface oriented towards the vertebral body of the upper vertebra and an essentially plane surface oriented towards the vertebral body of the lower vertebra.

11. The spine stabilization device according to claim 1 being an arthrodetic implant.

12. The spine stabilization device according to claim 11 being free of any components outside a space between the vertebral bodies of the upper and lower vertebra.

13. The spine stabilization device according to claim 1, wherein the interbody spacer further comprises retention structures.

14. The spine stabilization device according to claim 1, wherein the interbody spacer further comprises macroscopic bone ingrowth structures.

15. The spine stabilization device according to claim 1, wherein the interbody spacer further comprises microscopic bone ingrowth structures.

16. The spine stabilization device according to claim 1, wherein the interbody spacer is stiff and configured to rigidly connect the upper and lower vertebrae.

17. The spine stabilization device according to claim 1 being an intervertebral disc prosthesis, wherein the interbody spacer has a flexible portion.

18. The spine stabilization device according to claim 1, wherein an axis of each of the first and second cavities is approximately parallel to a median plane of the interbody spacer.

* * * * *